US009327035B2

(12) United States Patent
Fuh et al.

(10) Patent No.: US 9,327,035 B2
(45) Date of Patent: May 3, 2016

(54) ANTI-HER ANTIBODIES

(71) Applicant: Genentech, Inc., South San Francisco, CA (US)

(72) Inventors: Germaine Fuh, Pacifica, CA (US); Lauric Haber, San Carlos, CA (US); Gabriele Schaefer, San Mateo, CA (US); Mark X. Sliwkowski, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/066,258

(22) Filed: Oct. 29, 2013

(65) Prior Publication Data

US 2014/0056899 A1 Feb. 27, 2014

Related U.S. Application Data

(62) Division of application No. 12/728,052, filed on Mar. 19, 2010, now Pat. No. 8,597,652.

(60) Provisional application No. 61/210,562, filed on Mar. 20, 2009.

(51) Int. Cl.
C07K 16/32 (2006.01)
A61K 47/48 (2006.01)
C07K 16/28 (2006.01)
A61K 39/00 (2006.01)

(52) U.S. Cl.
CPC ........... *A61K 47/48569* (2013.01); *C07K 16/28* (2013.01); *C07K 16/2863* (2013.01); *C07K 16/32* (2013.01); *A61K 2039/505* (2013.01); *A61K 2039/507* (2013.01); *C07K 2317/31* (2013.01); *C07K 2317/56* (2013.01); *C07K 2317/565* (2013.01); *C07K 2317/73* (2013.01); *C07K 2317/732* (2013.01); *C07K 2317/92* (2013.01)

(58) Field of Classification Search
CPC ................... A61K 47/48569; C07K 2317/31; C07K 2317/732; C07K 16/32
USPC ..................................... 424/136.1; 530/387.3
See application file for complete search history.

(56) References Cited

U.S. PATENT DOCUMENTS

| | | | |
|---|---|---|---|
| 4,943,533 A | 7/1990 | Mendelsohn et al. |
| 5,480,968 A | 1/1996 | Kraus et al. |
| 5,770,195 A | 6/1998 | Hudziak et al. |
| 5,824,311 A | 10/1998 | Greene et al. |
| 5,916,755 A | 6/1999 | Kraus et al. |
| 5,968,511 A | 10/1999 | Akita et al. |
| 6,054,561 A | 4/2000 | Ring |
| 6,217,866 B1 | 4/2001 | Schlessinger et al. |
| 6,524,832 B1 | 2/2003 | Kufe et al. |
| 6,713,485 B2 | 3/2004 | Carter et al. |
| 6,719,971 B1 | 4/2004 | Carter et al. |
| 6,949,245 B1 | 9/2005 | Sliwkowski |
| 7,226,592 B2 | 6/2007 | Kreysch et al. |
| 7,332,579 B2 | 2/2008 | Gerritsen et al. |
| 7,332,580 B2 | 2/2008 | Adams et al. |
| 7,332,585 B2 | 2/2008 | Adams et al. |
| 7,449,184 B2 | 11/2008 | Allison et al. |
| 7,662,374 B2 | 2/2010 | Greene et al. |
| 7,704,498 B2 | 4/2010 | Gerristsen et al. |
| 7,705,130 B2 | 4/2010 | Rothe et al. |
| 7,846,440 B2 | 12/2010 | Schoeberl et al. |
| 8,124,085 B2 | 2/2012 | Nielsen et al. |
| 8,163,287 B2 | 4/2012 | Sliwkowski et al. |
| 2003/0086924 A1 | 5/2003 | Sliwkowski |
| 2003/0157104 A1 | 8/2003 | Waksal |
| 2004/0197332 A1 | 10/2004 | Ullrich et al. |
| 2005/0119288 A1 | 6/2005 | Bhattacharya et al. |
| 2006/0099205 A1 | 5/2006 | Adams et al. |
| 2008/0069820 A1 | 3/2008 | Fuh et al. |
| 2008/0299120 A1 | 12/2008 | Miller et al. |
| 2009/0246206 A1 | 10/2009 | Nielsen et al. |
| 2010/0196265 A1 | 8/2010 | Adams et al. |
| 2011/0033482 A1 | 2/2011 | Ullrich et al. |
| 2011/0229406 A1 | 9/2011 | Hettmann et al. |
| 2012/0121596 A1 | 5/2012 | Fuh et al. |
| 2013/0259867 A1* | 10/2013 | Amler et al. ............... 424/136.1 |
| 2014/0193414 A1* | 7/2014 | Fuh et al. .................. 424/136.1 |
| 2014/0314747 A1* | 10/2014 | Strasser et al. ............ 424/133.1 |

FOREIGN PATENT DOCUMENTS

| | | |
|---|---|---|
| EP | 1889631 | 2/2008 |
| EP | 1414494 B1 | 3/2009 |
| EP | 1355658 B1 | 3/2011 |
| WO | 99/60023 | 11/1999 |
| WO | 00/78347 | 12/2000 |
| WO | 02/11677 A2 | 2/2002 |

(Continued)

OTHER PUBLICATIONS

Arevalo et al., "Molecular basis of crossreactivity and the limits of antibody-antigen complementarity" Nature 365:859-863 (Oct. 1993).
Arteaga, "ErbB-targeted therapeutic approaches in human cancer" Exp Cell Res 284:122-130 (Mar. 2003).
Baselga et al., "Receptor blockade with monoclonal antibodies as anti-cancer therapy" Pharmac Ther 64:127-154 ( 1994).
Bispecific Antibodies Kontermann, Germany:Springer, ( 2011).
Bostrom et al., "Design and construction of synthetic phage-displayed Fab libraries," Methods Mol Biol 562:17-35 ( 2009).
Bostrom et al., "High affinity antigen recognition of the dual specific variants of Herceptin is entropy-driven in spite of structural plasticity" PloS one 6:e17887 ( 2011).
Bostrom et al., "High affinity antigen recognition of the dual specific variants of Herceptin is entropy-driven in spite of structural plasticity" PLoS One 6:e17887.
Bostrom et al., "Improving antibody binding affinity and specificity for therapeutic development," Methods Mol Biol 525:353-376 (2009).
Bostrom et al., "Variants of the antibody herceptin that interact with HER2 and VEGF at the antigen binding site," Science 323:1610-1614 (Mar. 2009).
Breuleux, "Role of heregulin in human cancer" Cell Mol Life Sci 64:2358-2377 ( 2007).
Brorson et al., "Mutational analysis of avidity and fine specificity of anti-levan antibodies," J Immunol (added article title info), 163:6694-6701 (Dec. 1999).

(Continued)

Primary Examiner — Lynn Bristol

(57) ABSTRACT

The invention provides anti-HER antibodies, including multispecific anti-HER antibodies, compositions comprising and methods of using these antibodies. Also provided herein are EGFR/HER3 multispecific antibodies that are less toxic than traditional EGFR antagonists.

13 Claims, 29 Drawing Sheets

(56) References Cited

FOREIGN PATENT DOCUMENTS

| WO | 02/060470 | A1 | 8/2002 |
|---|---|---|---|
| WO | 03/013602 | A1 | 2/2003 |
| WO | 03/102157 | A2 | 11/2003 |
| WO | 2004/003019 | A2 | 1/2004 |
| WO | 2005/117973 | A2 | 12/2005 |
| WO | 2006/091209 | | 8/2006 |
| WO | 2007042289 | | 4/2007 |
| WO | 2007/077028 | | 7/2007 |
| WO | 2008027236 | | 3/2008 |
| WO | 2008/100624 | A2 | 8/2008 |
| WO | 2008/140493 | | 11/2008 |
| WO | 2009127881 | | 10/2009 |
| WO | 2010/115552 | | 10/2010 |
| WO | 2011/076683 | | 6/2011 |

OTHER PUBLICATIONS

Brummell et al., "Probing the combining site of an anti-carbohydrate antibody by saturation-mutagenesis: role of the heavy-chain CDR3 residues," Biochemistry 32(4):1180-1187 (Feb. 1993).
Buck et al., "Inactivation of Akt by the epidermal growth factor receptor inhibitor erlotinib is mediated by HER-3 in pancreatic and colorectal tumor cell lines and contributes to erlotinib sensitivity" Mol Cancer Ther 5:2051-2059 ( 2006).
Burks et al., "In vitro scanning saturation mutagenesis of an antibody binding pocket," Proc. Natl. Acad. Sci. 94:412-417 ( 1997).
Burton et al., "Broadly neutralizing antibodies present new prospects to counter highly antigenically diverse viruses" Science 337:183-186 ( 2012).
Cho et al., "Structure of the extracellular region of HER2 alone and in complex with the Herceptin Fab," Nature 421:756-760 (Feb. 13, 2003).
Chothia et al., "Canonical structures for the hypervariable regions of immunoglobulins," J Mol Biol 196(4):901-917 ( 1987).
Coleman, P.M., "Effects of amino acid sequence changes on antibody-antigen interactions" Res Immunol 145:33-36 ( 1994).
Dall'Acqua et al., "A mutational analysis of the binding of two different proteins to the same antibody" Biochem 35:9667-9676 (1996).
de Kruif et al., "Leucine zipper dimerized bivalent and bispecific scFv antibodies from a semi-synthetic antibody phage display library" J Biol Chem 271(13):7630-7634 (Mar. 29, 1996).
Eigenbrot et al., "X-Ray structures of the antigen-binding domains from three variants of humanized anti-p185\\\superscript:HER2\\\ antibody 4D5 and comparison with molecular modeling" J Mol Biol 229:969-995 ( 1993).
Ekiert et al., "Broadly neutralizing antibodies against influenza virus and prospects for universal therapies" Curr Opin Virology 2:134-141 (2012).
Engelman et al., "Factors predicting response to EGFR tyrosine kinase inhibitors" Semin Respir Crit Care Med 26:314-322 ( 2005).
Engelman et al., "Select this articleErbB-3 mediates phosphoinositide 3-kinase activity in gefitinib-sensitive non-small cell lung cancer cell lines" P Natl Acad Sci USA 102:3788-3793 ( 2005).
Fendly et al., "Characterization of murine monoclonal antibodies reactive to either the human epidermal growth factor receptor or HER2/neu gene product" Cancer Res 50:1550-1558 (Mar. 1, 1990).
Foote et al., "Isomeric antibodies" Science 299:1327-1358 ( 2003).
Franklin et al., "Insights into ErbB signaling from the structure of the ErbB2-pertuzumab complex" Cancer Cell 5:317-328 (Apr. 2004).
Fuh et al., "Structure-function studies of two synthetic anti-vascular endothelial growth factor Fabs and comparison with the Avastin Fab" J Biol Chem 281(10):6625-6631 (Mar. 10, 2006).
Grothey, "EGFR antibodies in colorectal cancer: Where do they belong?" J Clin Oncol 28:4668-4670 ( 2010).
Holliger et al., "'Diabodies': Small bivalent and bispecific antibody fragments" P Natl Acad Sci USA 90:6444-6448 (Jul. 1993).
Hsieh et al., "Targeting HER proteins in cancer therapy and the role of the non-target HER3" Brit J Cancer 97:453-457 (Aug. 2007).
Htun van der Horst, E. et al., "Anti-HER-3 MAbs inhibit HER-3-mediated signaling in breast cancer cell lines resistant to anti-HER-2 antibodies" Int J Cancer 115:519-527 ( 2005).
Hynes et al., "ErbB receptors and signaling pathways in cancer" Curr Opin Cell Biol 21:177-184 ( 2009).
International Prelminary Examination Report on Patentability for PCT/US2010/028023 (Date of mailing Sep. 20, 2011).
International Search Report for PCT/US2010/028023 (Date of mailing May 12, 2010).
James et al., "Antibody multispecificity mediated by conformational diversity" Science 299:1362-1367 (Feb. 2003).
Jang et al., "The structural basis for DNA binding by an anti-DNA autoantibody" Mol Immunol. 35(18):1207-17 (Dec. 1998).
Jimenez et al., "Flexibility and molecular recognition in the immune system" P Natl Acad Sci USA 100:92-97 (Jan. 2003).
Jones et al., "Neoadjuvant treatment for early-stage breast cancer: opportunities to assess tumour response" Lancet Oncol 7:869-874 ( 2006).
Keitel et al., "Crystallographic analysis of anti-p24 (HIV-1) monoclonal antibody cross-reactivity and polyspecificity" Cell 91:811-820 ( 1997).
Kelley et al., "Antigen binding thermodynamics and antiproliferative effects of chimeric and humanized anti-p185HER2 antibody Fab fragments" Biochem 31:5434-5441 ( 1992).
Kelley et al., "Thermodynamic analysis of an antibody functional epitope" Biochem 32:6828-6835 ( 1993).
Kobayashi, H., et al. et al., "Tryptophan H33 plays an important role in pyrimidin (6-4) pyrimidone photoproduct binding by a high-affinity antibody" Protein Eng 12(10):879-884 ( 1999).
Kohler and Milstein, "Continuous cultures of fused cells secreting antibody of predefined specificity" Nature 256:495-497 (Aug. 7, 1975).
Kontermann et al., "Production of recombinant biscpecific antibodies" Methods Mol Biol 248:227-242 ( 2004).
Kontermann, R., "Recombinant bispecific antibodies for cancer therapy" Acta Pharmacologica Sinica 26(1):1-9 (Jan. 2005).
Kostelny et al., "Formation of a bispecific antibody by the use of leucine zippers" J Immunol 148(5):1547-1553 (Mar. 1, 1992).
Kramer et al., "Molecular basis for the binding promiscuity of an anti-p24 (HIV-1) monoclonal antibody" Cell 91:799-809 ( 1997).
Kufer et al., "A revival of bispecific antibodies" Trends Biotechnol 22(5):238-244 (May 2004).
Kumar, Sanjeev et al., "Molecular cloning and expression of the fabs of human autoantibodies in *escherichia coli*" J Biol Chem 275(45):35129-35136 ( 2000).
Lacouture, "Mechanisms of cutaneous toxicities to EGFR inhibitors" Nat Rev Cancer 6:803-812 (Oct. 2006).
Lee et al., "Bivalent antibody phage display mimics natural immunoglobulin" J Immunol Methods 284(1-2):119-132 ( 2004).
Lee et al., "High-affinity human antibodies from phage-displayed synthetic single Fab libraries with a single framework scaffold" J Mol Biol 340(5):1073-1093 ( 2004).
Lee et al., "Synthetic anti-BR3 antibodies that mimic BAFF binding and target both human and murine B cells" Blood 108:3103-3111 (2006).
Li et al., "Structural basis for inhibition of the epidermal growth factor receptor by cetuximab" Cancer Cell 7:301-311 ( 2005).
Lowman et al., "Selecting High-Affinity Binding Proteins by Monovalent Phage Display" Biochem 30(45):10832-10838 ( 1991).
Lum et al., "The new face of bispecific antibodies: targeting cancer and much more" Exp Hematol 34:1-6 (Jan. 2006).
Marks et al., "By-passing immunization, human antibodies from V-gene libraries displayed on phage" J Mol Biol 222:581-597 (1991).
Marks et al., "By-passing immunization: building high affinity human antibodies by chain shuffling" Bio/Technology 10:779-783 (Jul. 1992).
Marvin et al., "Recombinant approaches to IgG-like bispecific antibodies" Acta Pharmacologica Sinica 26(6):649-658 (Jun. 2005).
McIntyre et al., "The complete family of epidermal growth factor receptors and their ligands are co-ordinately expressed in breast cancer" Breast Cancer Res Treat 122:105-110 (Jul. 2010).
Mohan et al., "Association energetics of cross-reactive and specific antibodies" Biochem 48:1390-8 ( 2009).

(56) References Cited

OTHER PUBLICATIONS

Notkins, "Polyreactivity of antibody molecules" Trends Immunol 25(4):174-9 (Apr. 2004).

Ocana et al., "An update into the pathophysiological role of HER2 in cancer: therapeutic implications" Clin Transl Oncol 9:543-544 (2007).

Olayioye et al., "The ErbB signaling network: receptor heterodimerization in development and cancer" EMBO J 19(13):3159-3167 (2000).

Parren et al., "Two-in-one designer antibodies" Science 323:1567-1568 (Mar. 20, 2009).

Response to Written Opinion for Corresponding European Patent Application EP10710142 (Date of mailing May 10, 2012).

Robinson et al., "Targeting ErbB2 and ErbB3 with a bispecific single-chain Fv enhances targeting selectivity and induces a therapeutic effect in vitro" Brit J Cancer 99:1415-1425 (2008).

Schaefer et al., "A two-in-one antibody against HER3 and EGFR has superior inhibitory activity compared with monospecific antibodies original research article" Cancer Cell 20:472-486 (2011).

Schoeberl et al., "An ErbB3 antibody, MM-121, is active in cancers with ligand-dependent activation" Cancer Res 70:2485-2494 (Mar. 2010).

Sethi et al., "Differential epitope positioning within the germline antibody paratope enhances promiscuity in the primary Immune response" Immunity 24:429-438 (2006).

Shen et al., "Single variable domain antibody as a versatile building block for the construction of IgG-like bispecific antibodies" J Immunol Methods 318:65-74 (2007).

Sheng et al., "An activated ErbB3/NRG1 autocrine loop supports in vivo proliferation in ovarian cancer cells" Cancer Cell 17:298-310 (Mar. 2010).

Sidhu et al., "Phage-displayed antibody libraries of synthetic heavy chain complementary determining regions" J Mol Biol 338:299-310 (2004).

Smith-Gill, S., et al. et al., "Contributions of immunoglobulin heavy and light chains to antibody specificity for lysozyme and two haptens" J Immunol 139:4135-4144 (1987).

Song, Mi-Kyung, et al. et al., "Light chain of natural antibody plays a dominant role in protein antigen binding" Biochem Bioph Res Co 268:390-394 (2000).

Stone et al., "The assembly of single domain antibodies into bispecific decavalent molecules" J Immunol Methods 318:88-94 (Jan. 2007).

Taylor et al., "FcγRIIIa polymorphisms and cetuximab induced cytotoxicity in squamous cell carcinoma of the head and neck" Cancer Immunol Immun 58:997-1006 (2009).

Treder, M. et al., "Fully human anti-HER3 mAb U3-1287 (AMG 888) demonstrates unique in vitro and in vivo activities versus other HER family inhibitors in NSCLC models" Eur J Cancer Supp. (309 Poster), 6(12) (Oct. 2008).

Trinh et al., "Antibody fragment Fv4155 bound to two closely related steroid hormones: the structural basis of fine specificity" Structure 5:937-948 (1997).

Valladares et al., "Designing two-in-one antibodies" J Immunother 1:749-751 (Sep. 2009).

Ward et al., Nature 341:544-546 (1989).

Wheeler et al., "Mechanisms of acquired resistance to cetuximab: role of HER (ErbB) family members" Oncogene 27:3944-3956 (Jun. 2008).

Winter et al., "Making antibodies by phage display technology" Annu Rev Immunol 12:433-455 (1994).

Yarden et al., "The ERBB network: at last, cancer therapy meets systems biology" Nat Rev Cancer 12:553-563 (2012).

Yarden et al., "Untangling the ErbB signalling network" Nat Rev Mol Cell Biol 2:127-137 (Feb. 2001).

Zaczek et al., "The diverse signaling network of EGFR, HER2, HER3 and HER4 tyrosine kinase receptors and the consequences for therapeutic approaches" Histol Histopathol 20:1005-1015 (2005).

\* cited by examiner

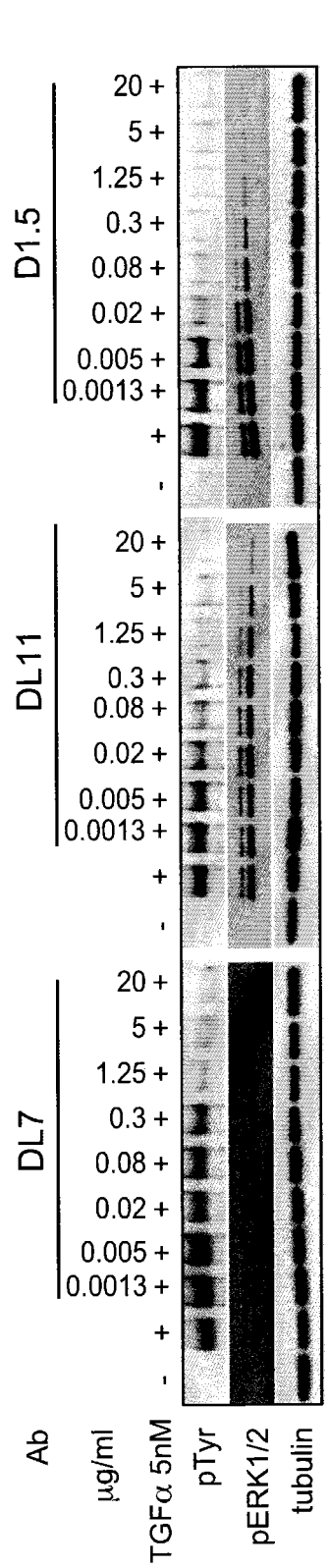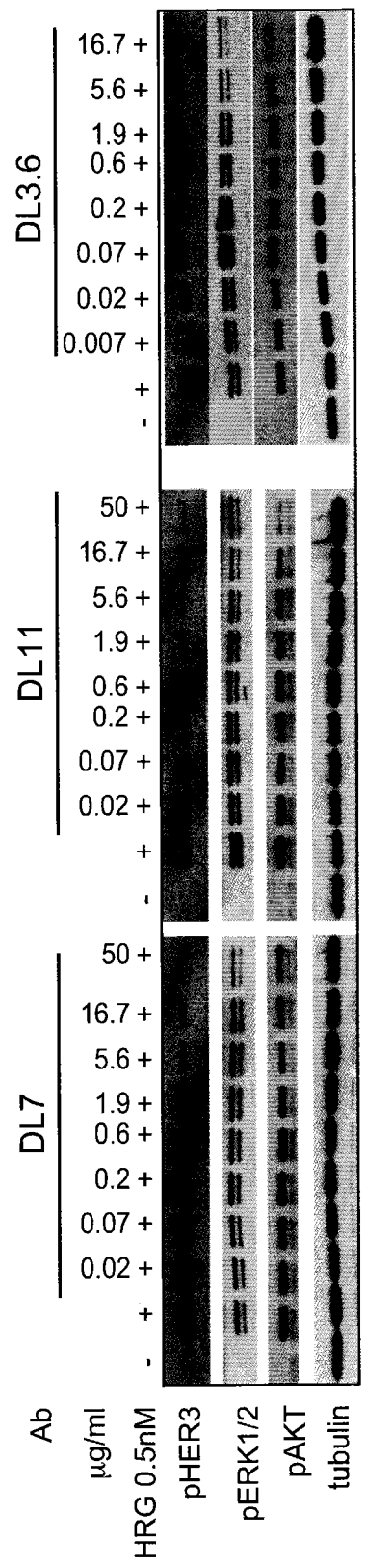
FIG. 10A
FIG. 10B

| EGFR Antagonist | Nonclinical Data | Clinical Data |
|---|---|---|
| ERBITUX® (cetuximab) Imclone (BLA No.: 125084) Recombinant human/mouse chimeric monoclonal antibody that binds specifically to extracellular domain of EGFR | 9 months repeat-dose toxicity study conducted in cynomolgus monkeys. Doses and regimen: Administered once weekly for 9 months at doses approx. 0.4-4 X's (7.5, 24 and 75 mg/kg/week) above weekly human exposure based on BSA Major test article-related tox: Mild to severe skin lesions (scale formation, erythema, dermatitis, fissures, wounds, exanthema on various parts of body) at all dose levels. Severity and onset was dependent on dose. Onset for high, mid and low doses were on Study Days 15, 22 and 64, respectively. Secondary complication of severe skin lesions was bacterial infection or sepsis with subsequent euthanasia of 50% of animals in moribund condition in high dose group. | Dosing regimen for cetuximab was the same for all trials: On Day 1, test dose of 20 mg was given following by 400 mg/m2 initial dose and then 250 mg/m2 dose for the duration of radiation therapy (6-7 weeks) or until progression of disease or unacceptable toxicities. Dermatological toxicities (acneform rash, skin drying and fissuring and inflammatory and infectious sequelea (eg. blephantis, cheilitis, cellulitis, cyst) also reported in clinical trials. Secondary complications were reported including S. aureus sepsis and abcesses requiring incision and drainage. Squamous cell carcinoma of head and neck clinical trial results: acneform rash was reported in 76% of patients treated with cetuximab alone of which 1% were regarded as severe vs 10% with radiation therapy only. Colorectal cancer trial results: acneform rash was reported in 89% of patients treated with cetuximab of which 11% were regarded as severe. |

FIG. 31A

| EGFR Antagonist | Nonclinical Data | Clinical Data |
|---|---|---|
| TARCEVA® (Erlotinib hydrochloride) OSI Pharms /Genentech (NDA No. 021743) Small molecule which inhibits the intracellular phosphorylation of tyrosine kinase associated with EGFR. | 6 months oral toxicity study in Sprague-Dawley rat and 12 months oral toxicity study in Beagle dog were conducted. In the summary of the NDA, target sites of toxicity were listed and dermatological was included in the list. <u>Rat study findings:</u> Doses – 1, 5 and 10 m/kg/day Clinical findings: Skin lesion described as scabs on muzzle from Day 50 onwards in the high dose group. <u>Histopathology findings:</u> degeneration and inflammation of skin in 2/15 males and 2/15 females at 5 mg/kg/day and 11/15 males and 11/15 females at 10 mg/kg/day. No histopath finding for skin in controls. <u>Dog study findings:</u> Doses – 2.5, 7.5 and 15 mg/kg/day Clinical signs: All dose groups included redness of skin (in 2/8, 3/8 and 5/8 dogs, respectively) and redness of buccal mucus membrane (in 4/8, 6/8 and 8/8 dogs, respectively). Time to onset of findings, decreased with increasing dose. | Dosing regimen was 150 mg daily, 2 hours before food ingestion. <u>Clinical trial findings:</u> Generally well tolerated. Most frequently occurring toxicities include skin rash and diarrhea. The latter two toxicities sometimes resulted in dose-reduction or discontinuation of treatment. |

*FIG. 31B*

| EGFR Antagonist | Nonclinical Data | Clinical Data |
|---|---|---|
| VECTIBIX ® (panitumumab)<br><br>Amgen<br><br>(BLA No. 125147)<br><br>Recombinant fully humanized monoclonal antibody directed against human EGFR | Several repeat dose toxicity studies were conducted in the cynomolgus monkey. Severe dermatologic toxicities were reported in these studies at doses of 7.5, 15, 30 or 60 mg/kg for 4, 13 or 26 weeks treatment duration.<br>26-week study results:<br>Doses: 7.5, 15 and 30 mg/kg/dose, IV bolus once a week.<br>Summary of findings: Mild to severe dermatologic toxicities (erythema, irritation, crus (often associated with secondary infections), flaky skin (dandruff-like), loss of fur, abrasions, and/or eyelid swelling and eye redness), epidermal sloughing, septicemia and deaths (2, 6, and 6 in LD, MD and HD, respectively) in all dose groups. In addition, papules and/or ulceration/necrosis were sporadically reported in all dose groups.<br>Histopathology findings:<br>Mild to marked hyperkeratosis, accompanied by epidermal acanthosis, parakeratosis in skin of animals in all dose groups. Severity was the same for 15 and 30 mg/kg dose groups and slightly reduced in 7.5 mg/kg dose group.<br>No NOAEL was determined.<br>Doses were 1.25 to 10-fold greater than proposed 6 mg/kg human dose every 2 weeks and approximately 3-24-fold higher than proposed 2.5 mg/kg/week dose when adjusted to body weight of the human. | Dosing regimen was 6 mg/kg daily every 2 weeks until disease progression.<br><br>Clinical trial findings:<br>One of the most serious adverse events reported was dermatologic toxicities complicated by infections sequelae and septic death.<br><br>Skin lesions (acneform rash, pruritis, dry skin, exfoliation, skin fissures and paronychia) were reported in 90% of 789 metastatic colorectal cancer patients. These were Grade 2 in severity with 12% of patients having Grade 3 in severity. In patients (not observed nonclinically), Grade 1 or 2 stomatitis and oral mucositis was also reported in 7% of patients. Development of severe dermatologic toxicities did lead to secondary infections (sepsis) and on rare occasions even death but most frequently a dose reduction or interruption was necessary.<br><br>Labeling review included a Boxed Warning section for dermatologic toxicities. |

FIG. 31C

| Adverse Event | Short Name | Grade 1 | Grade 2 | Grade 3 | Grade 4 | Grade 5 |
|---|---|---|---|---|---|---|
| Rash/ Desquamation | Rash | Macular or papular eruption or erythema without associated symptoms | Macular or papular eruption or erythema with pruritus or other associated symptoms; or other lesions covering <50% of body surface area (BSA) | Severe, generalized erythroderma or macular, papular or vesicular eruption; desquamation covering >50% BSA | Generalized, exfoliative, ulcerative, or bullous dermatitis | Death |
| Rash: Acne/aneiform | Acne | Intervention not indicated | Intervention indicated | Associated with pain, disfigurement, ulceration, or desquamation | - | Death |

FIG. 32

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| D1 | D | I | Q | M | T | Q | S | P | S | S | L | S | A | S | V | G | D | R | V | T | I | T | C | R | A | S | Q | | | | | | | D | V | S | T | A | V | A | W | Y | Q |
| D1.5 | D | I | Q | M | T | Q | S | P | S | S | L | S | A | S | V | G | D | R | V | T | I | T | C | R | A | S | Q | | | | | | | D | V | S | T | A | V | A | W | Y | Q |
| D1.5-100 | D | I | Q | M | T | Q | S | P | S | S | L | S | A | S | V | G | D | R | V | T | I | T | C | R | A | S | Q | | | | | | | D | L | A | T | D | V | A | W | Y | Q |
| DL11 | D | I | Q | M | T | Q | S | P | S | S | L | S | A | S | V | G | D | R | V | T | I | T | C | R | A | S | Q | | | | | | | D | L | A | T | D | V | A | W | Y | Q |
| DL11b | D | I | Q | M | T | Q | S | P | S | S | L | S | A | S | V | G | D | R | V | T | I | T | C | R | A | S | Q | | | | | | | N | I | A | T | D | V | A | W | Y | Q |
| DL11f | D | I | Q | M | T | Q | S | P | S | S | L | S | A | S | V | G | D | R | V | T | I | T | C | R | A | S | Q | | | | | | | N | I | A | T | D | V | A | W | Y | Q |

| Kabat# | 38 | 39 | 40 | 41 | 42 | 43 | 44 | 45 | 46 | 47 | 48 | A | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| D1 | Q | K | P | G | K | A | P | K | L | L | I | | Y | S | A | S | F | L | Y | S | G | V | P | S | R | F | S | G | S | G | S | G | T | D | F | T | L | T | I | S | S | L | Q | P |
| D1.5 | Q | K | P | G | K | A | P | K | L | L | I | | Y | S | A | S | F | L | Y | S | G | V | P | S | R | F | S | G | S | G | S | G | T | D | F | T | L | T | I | S | S | L | Q | P |
| D1.5-100 | Q | K | P | G | K | A | P | K | L | L | I | | Y | S | A | S | F | L | Y | S | G | V | P | S | R | F | S | G | S | G | S | G | T | D | F | T | L | T | I | S | S | L | Q | P |
| DL11 | Q | K | P | G | K | A | P | K | L | L | I | | Y | S | A | S | F | L | Y | S | G | V | P | S | R | F | S | G | S | G | S | G | T | D | F | T | L | T | I | S | S | L | Q | P |
| DL11b | Q | K | P | G | K | A | P | K | L | L | I | | Y | S | A | S | F | L | Y | S | G | V | P | S | R | F | S | G | S | G | S | G | T | D | F | T | L | T | I | S | S | L | Q | P |
| DL11f | Q | K | P | G | K | A | P | K | L | L | I | | Y | S | A | S | F | L | Y | S | G | V | P | S | R | F | S | G | S | G | S | G | T | D | F | T | L | T | I | S | S | L | Q | P |

| Kabat# | 81 | 82 | 83 | 84 | 85 | 86 | 87 | 88 | 89 | 90 | 91 | 92 | 93 | 94 | 95 | A | B | C | D | E | F | 96 | 97 | 98 | 99 | 100 | 101 | 102 | 103 | 104 | 105 | 106 | 107 | 108 |
|---|---|---|---|---|---|---|---|---|---|---|---|---|---|---|---|---|---|---|---|---|---|---|---|---|---|---|---|---|---|---|---|---|---|---|
| D1 | E | D | F | A | T | Y | Y | C | Q | Q | S | Y | T | T | P | | | | | | | P | T | F | G | Q | G | T | K | V | E | I | K | R |
| D1.5 | E | D | F | A | T | Y | Y | C | Q | Q | S | Y | P | T | P | | | | | | | Y | T | F | G | Q | G | T | K | V | E | I | K | R |
| D1.5-100 | E | D | F | A | T | Y | Y | C | Q | Q | S | E | P | E | P | | | | | | | Y | T | F | G | Q | G | T | K | V | E | I | K | R |
| DL11 | E | D | F | A | T | Y | Y | C | Q | Q | S | E | P | E | P | | | | | | | Y | T | F | G | Q | G | T | K | V | E | I | K | R |
| DL11b | E | D | F | A | T | Y | Y | C | Q | Q | S | E | P | E | P | | | | | | | Y | T | F | G | Q | G | T | K | V | E | I | K | R |
| DL11f | E | D | F | A | T | Y | Y | C | Q | Q | S | E | P | E | P | | | | | | | Y | | F | G | Q | G | T | K | V | E | I | K | R |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | B | A | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| D1      | E | V | Q | L | V | E | S | G | G | G | L | V | Q | P | G | G | S | L | R | L | S | C | A | A | S | G | F | T | F | T | G | N | W | I | H |   |   | W | V | R | Q | A | P |
| D1.5    | E | V | Q | L | V | E | S | G | G | G | L | V | Q | P | G | G | S | L | R | L | S | C | A | A | S | G | F | T | F | T | G | N | W | I | H |   |   | W | V | R | Q | A | P |
| D1.5-100| E | V | Q | L | V | E | S | G | G | G | L | V | Q | P | G | G | S | L | R | L | S | C | A | A | S | G | F | T | F | T | G | N | W | I | H |   |   | W | V | R | Q | A | P |
| DL11    | E | V | Q | L | V | E | S | G | G | G | L | V | Q | P | G | G | S | L | R | L | S | C | A | A | S | G | F | T | L | S | G | D | W | I | H |   |   | W | V | R | Q | A | P |
| DL11b   | E | V | Q | L | V | E | S | G | G | G | L | V | Q | P | G | G | S | L | R | L | S | C | A | A | S | G | F | T | L | S | G | D | W | I | H |   |   | W | V | R | Q | A | P |
| DL11f   | E | V | Q | L | V | E | S | G | G | G | L | V | Q | P | G | G | S | L | R | L | S | C | A | A | S | G | F | T | L | S | G | D | W | I | H |   |   | W | V | R | Q | A | P |

| Kabat# | 42 | 43 | 44 | 45 | 46 | 47 | 48 | 49 | 50 | 51 | 52 | a | b | c | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| D1      | G | K | G | L | E | W | V | G | E | I | S |   |   |   | S | G | G | Y | T | D | Y | A | D | S | V | K | G | R | F | T | I | S | A | D | T | S | K | N | T | A | Y | L |
| D1.5    | G | K | G | L | E | W | V | G | E | I | S |   |   |   | S | G | G | Y | T | D | Y | A | D | S | V | K | G | R | F | T | I | S | A | D | T | S | K | N | T | A | Y | L |
| D1.5-100| G | K | G | L | E | W | V | G | E | I | S | P |   |   | S | G | G | Y | T | D | Y | A | D | S | V | K | G | R | F | T | I | S | A | D | T | S | K | N | T | A | Y | L |
| DL11    | G | K | G | L | E | W | L | G | E | I | S | P | A |   | A | G | G | Y | T | D | Y | A | D | S | V | K | G | R | F | T | I | S | A | D | T | S | K | N | T | A | Y | L |
| DL11b   | G | K | G | L | E | W | L | G | E | I | S | P | A |   | A | G | G | Y | T | D | Y | A | D | S | V | K | G | R | F | T | I | S | A | D | T | S | K | N | T | A | Y | L |
| DL11f   | G | K | G | L | E | W | V | G | E | I | S | A |   |   | A | G | G | Y | T | D | Y | A | D | S | V | K | G | R | F | T | I | S | A | D | T | S | K | N | T | A | Y | L |

| Kabat# | 81 | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | F | G | H | I | J | K | 101 | 102 | 103 | 104 | 105 | 106 | 107 | 108 | 109 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| D1      | Q | M | N | S | L | R | A | E | D | T | A | V | Y | Y | C | A | R | E | S | R | V | S | Y | E | A |   |   |   |   |   |   |   |   |   | M | D | Y | W | G | Q | G | T | L | V |
| D1.5    | Q | M | N | S | L | R | A | E | D | T | A | V | Y | Y | C | A | R | E | S | R | V | S | Y | E | A |   |   |   |   |   |   |   |   |   | M | D | Y | W | G | Q | G | T | L | V |
| D1.5-100| Q | M | N | S | L | R | A | E | D | T | A | V | Y | Y | C | A | R | E | S | R | V | S | Y | E | A |   |   |   |   |   |   |   |   |   | M | D | Y | W | G | Q | G | T | L | V |
| DL11    | Q | M | N | S | L | R | A | E | D | T | A | V | Y | Y | C | A | R | E | S | R | V | S | F | E | A |   |   |   |   |   |   |   |   |   | M | D | Y | W | G | Q | G | T | L | V |
| DL11b   | Q | M | N | S | L | R | A | E | D | T | A | V | Y | Y | C | A | R | E | S | R | V | S | F | E | A |   |   |   |   |   |   |   |   |   | M | D | Y | W | G | Q | G | T | L | V |
| DL11f   | Q | M | N | S | L | R | A | E | D | T | A | V | Y | Y | C | A | R | E | S | R | V | S | F | E | A |   |   |   |   |   |   |   |   |   | M | D | Y | W | G | Q | G | T | L | V |

ANTI-HER ANTIBODIES

RELATED APPLICATIONS

This application claims the benefit of priority under 35 USC 119(e) of U.S. Provisional Application No. 61/210,562, filed Mar. 20, 2009, the disclosure of which is incorporated herein by reference in its entirety.

FIELD OF THE INVENTION

The present invention concerns anti-HER antibodies, including multispecific anti-HER antibodies with binding specificity for at least two different HER receptors, and use of the antibodies to treat diseases or disorders.

BACKGROUND OF THE INVENTION

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

EGFR, encoded by the erbB 1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF- and EGF, have been evaluated as therapeutic agents in the treatment of such malignancies. See, e.g., Baselga and Mendelsohn., supra; Masui et al. *Cancer Research* 44:1002-1007 (1984); and Wu et al. *J. Clin. Invest.* 95:1897-1905 (1995).

The second member of the HER family, HER2 (p185$^{neu}$), was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science,* 235:177-182 (1987); Slamon et al., *Science,* 244:707-712 (1989); and U.S. Pat. No. 4,968,603). Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science,* 229:974 (1985); Yokota et al., *Lancet:* 1:765-767 (1986); Fukushige et al., *Mol Cell Biol.,* 6:955-958 (1986); Guerin et al., *Oncogene Res.,* 3:21-31 (1988); Cohen et al., *Oncogene,* 4:81-88 (1989); Yonemura et al., *Cancer Res.,* 51:1034 (1991); Borst et al., *Gynecol. Oncol.,* 38:364 (1990); Weiner et al., *Cancer Res.,* 50:421-425 (1990); Kern et al., *Cancer Res.,* 50:5184 (1990); Park et al., *Cancer Res.,* 49:6605 (1989); Zhau et al., *Mol. Carcinog.,* 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat p185$^{neu}$ and human HER2 protein products have been described. Drebin and colleagues have raised antibodies against the rat neu gene product, p185$^{neu}$ See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein.

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening resulted in the identification of two other HER receptor family members; HER3 (U.S. Pat. Nos. 5,968,511, 5,183,884 and 5,480,968 as well as Kraus et al. *PNAS (USA)* 86:9193-9197 (1989)) and HER4 (EP Pat Appln No 599,274; Plowman et al., *Proc. Natl. Acad. Sci. USA,*

90:1746-1750 (1993); and Plowman et al., *Nature,* 366:473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science,* 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Three additional HER ligands have been identified; neuregulin-2 (NRG-2) which is reported to bind either HER3 or HER4 (Chang et al. Nature 387 509-512 (1997); and Carraway et al *Nature* 387:512-516 (1997)); neuregulin-3 which binds HER4 (Zhang et al. *PNAS (USA)* 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.,* 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.,* 56:1457-1465 (1996) with respect to the HER2-HER3 protein complex. HER4, like HER3, forms an active signaling complex with HER2 (Carraway and Cantley, *Cell* 78:5-8 (1994)).

Therapeutics that target the HER pathway are presently in use in treating diseases such as breast cancer, non-small cell lung cancer, colorectal cancer, head and neck cancer and pancreatic cancer. While these therapeutics have had some success, there remain issues related to native and induced resistance and toxicity. Arteaga C L. *J Clin Oncol* 21:289-91s (2003); Hoshi S, et al., *Gan To Kagaku Ryoho* 31:1209-13 (2004); Viloria-Petit A M, and Kerbel R S. *Int J Radiat Oncol Biol Phys* 58:914-26 (2004); Bianco R, et al., *Endocr Relat Cancer* 12:S159-71 (2005); Engelman J A, and Janne P A., *Clin Cancer Res* 14:2895-9 (2008); Davoli A, et al., *Cancer Chemother Pharmacol.* 65(4):611-23 (2010); Pohlmann P R, et al., *Clin Cancer Res.* 15(24):7479-7491 (2009). In particular, therapeutics that target HER1 (EGFR) are often associated with undesirable side effects, such as significant levels of skin toxicity. Robert, et al. *Lancet Oncology* 6:491-500 (2005).

Accordingly, a need exists to develop improved therapeutics that target the HER pathway.

SUMMARY OF THE INVENTION

The invention provides for multispecific antibodies comprising an antigen-binding domain that specifically binds to at least two HER receptors selected from the group consisting of (a) EGFR and HER2, (b) EGFR and HER3, and (c) EGFR and HER4. The antibody inhibits a biological activity of at least one of the HER receptors. In particular embodiments, the multispecific antibody specifically binds to its target HER receptors and does not specifically bind to the non-target HER receptors. Accordingly, in one embodiment, the antibody specifically binds to EGFR and HER3 but does not specifically bind to HER2 or HER4. In another embodiment, the antibody specifically binds to EGFR and HER2 but does not specifically bind to HER3 or HER4. In another embodiment, the antibody specifically binds to EGFR and HER4 but does not specifically bind to HER2 or HER3. The invention also provides for monospecific antibodies that specifically bind to a target HER receptor.

One aspect of the invention provides for multispecific antibodies that are capable of specifically binding to EGFR and another HER receptor that are less toxic than traditional EGFR antagonists, such as cetuximab. In one embodiment, the toxicity is dermatological toxicity. In one embodiment, the multispecific HER antibody comprises an antigen-binding domain that specifically binds to EGFR and HER3.

In one aspect, the invention provides a multispecific antibody comprising an antigen-binding domain that specifically binds to EGFR and HER3. In one embodiment, the multispecific antibody is less toxic than EGFR antagonists. In one embodiment, the multispecific antibody inhibits a biological activity of at least one of EGFR and HER3. In one embodiment, the antibody inhibits EGF binding to EGFR. In another embodiment, the antibody inhibits TGF-α induced EGFR phosphorylation. In some embodiments, the antibody inhibits tumor cell growth. In one embodiment, the multispecific antibody specifically binds to EGFR and HER3 but does not specifically bind to HER2 or HER4.

In one embodiment, the multispecific antibody comprises an antigen-binding domain that specifically binds to EGFR and HER3 with a Kd of less than $10^{-6}$M. In one embodiment the multispecific antibody comprises an antigen-binding domain that specifically binds EGFR with a Kd of less than $10^{-6}$M and specifically binds HER3 with a Kd of less than $10^{-7}$M.

In one embodiment, the multispecific antibody comprising an antigen-binding domain that specifically binds to EGFR and HER3 comprises (a) HVR-H1 comprising the amino acid sequence of LSGDWIH (SEQ ID NO: 48); (b) HVR-H2 comprising the amino acid sequence of VGEISAAGGYTD (SEQ ID NO: 51); and (c) HVR-H3 comprising the amino acid sequence of ARESRVSFEAAMDY (SEQ ID NO: 53); and (d) HVR-L1 comprising the amino acid sequence of NIATDVA (SEQ ID NO: 55); (e) HVR-L2 comprising the amino acid sequence of SASF (SEQ ID NO: 56); and (f) HVR-L3 comprising the amino acid sequence of SEPEPYT (SEQ ID NO: 57).

In one embodiment, the multispecific antibody comprising an antigen-binding domain that specifically binds to EGFR and HER3 comprises (a) a heavy chain variable domain having at least 95% sequence identity to the amino acid sequence of SEQ ID NO: 30; (b) a light chain variable domain having at least 95% sequence identity to the amino acid sequence of SEQ ID NO: 29; or (c) a heavy chain variable domain sequence as in (a) and a light chain variable domain sequence as in (b). In one embodiment, the multispecific antibody comprising an antigen-binding domain that specifically binds to EGFR and HER3 comprises a heavy chain variable domain sequence of SEQ ID NO: 30. In one embodiment, the multispecific antibody comprising an antigen-binding domain that specifically binds to EGFR and HER3 comprises a light chain variable domain sequence of SEQ ID NO: 29. In another embodiment, the multispecific antibody comprising an antigen-binding domain that specifically binds to EGFR and HER3 comprises a heavy chain variable domain sequence of SEQ ID NO: 30 and a light chain variable domain sequence of SEQ ID NO: 29.

In some embodiments, the multispecific antibody comprising an antigen-binding domain that specifically binds to EGFR and HER3 is a full length IgG1 antibody.

One aspect of the invention provides for an isolated nucleic acid encoding the multispecific HER antibodies. Another aspect provides for a host cell comprising the nucleic acid encoding the multispecific HER antibodies. Yet another aspect provides for a method of producing a multispecific HER antibody comprising culturing the host cell comprising the nucleic acid encoding the multispecific HER antibody so that the antibody is produced.

One aspect of the invention provides for an immunoconjugate comprising a multispecific HER antibody and a cytotoxic agent. Another aspect provides a pharmaceutical formulation comprising a multispecific HER antibody and a pharmaceutically acceptable carrier.

One aspect of the invention provides for a method of treating an individual having cancer comprising administering to the individual an effective amount of a multispecific HER antibody. In one embodiment, the multispecific HER antibody comprises an antigen-binding domain that specifically binds to EGFR and HER3. In one embodiment, the cancer treated by the multispecific HER antibody comprises cells that express EGFR and HER3. In one embodiment, the cancer treated by the multispecific HER antibody is breast cancer, colorectal cancer, pancreatic cancer, head and neck cancer, melanoma, ovarian cancer, prostate cancer, or non-small lung cell cancer.

Another aspect of the invention provides for a method of inhibiting a biological activity of a HER receptor in an individual comprising administering to the individual an effective amount of a multispecific HER antibody. In one embodiment, the multispecific HER antibody comprises an antigen-binding domain that specifically binds to EGFR and HER3.

BRIEF DESCRIPTION OF THE DRAWINGS

FIG. 10: A) Shows the comparison of the inhibitory function of affinity matured antibodies DL7 and DL11 and parental antibody D1.5 on EGFR. B) Shows the comparison of the inhibitory function of affinity matured antibodies DL7 and DL11, and monospecific anti-HER3 antibody DL3.6 on HER3 transactivation.

FIG. 31A-C is a table providing information on observed non-clinical and clinical toxicities for EGFR antagonist therapies.

FIG. 32 is a table providing information on grading for rash/desquamation and acne/acneiform rash.

FIG. 33 provides an amino acid alignment of the heavy chain variable domain and light chain variable domain of several anti-HER antibodies with Kabat numbering. FIG. 33A shows the light chain variable domain of the following antibodies: D1 (SEQ ID NO: 58); D1.5 (SEQ ID NO: 24); D1.5-100 (SEQ ID NO: 40); DL11 (SEQ ID NO: 27); DL11b (SEQ ID NO: 29); DL11f (SEQ ID NO: 29). FIG. 33B shows the heavy chain variable domain of the following antibodies: D1 (SEQ ID NO: 25); D1.5 (SEQ ID NO: 25); D1.5-100 (SEQ ID NO: 25); DL11 (SEQ ID NO: 28); DL11b (SEQ ID NO: 28); DL1 if (SEQ ID NO: 30).

DETAILED DESCRIPTION OF THE INVENTION

I. Definitions

Figure 1:
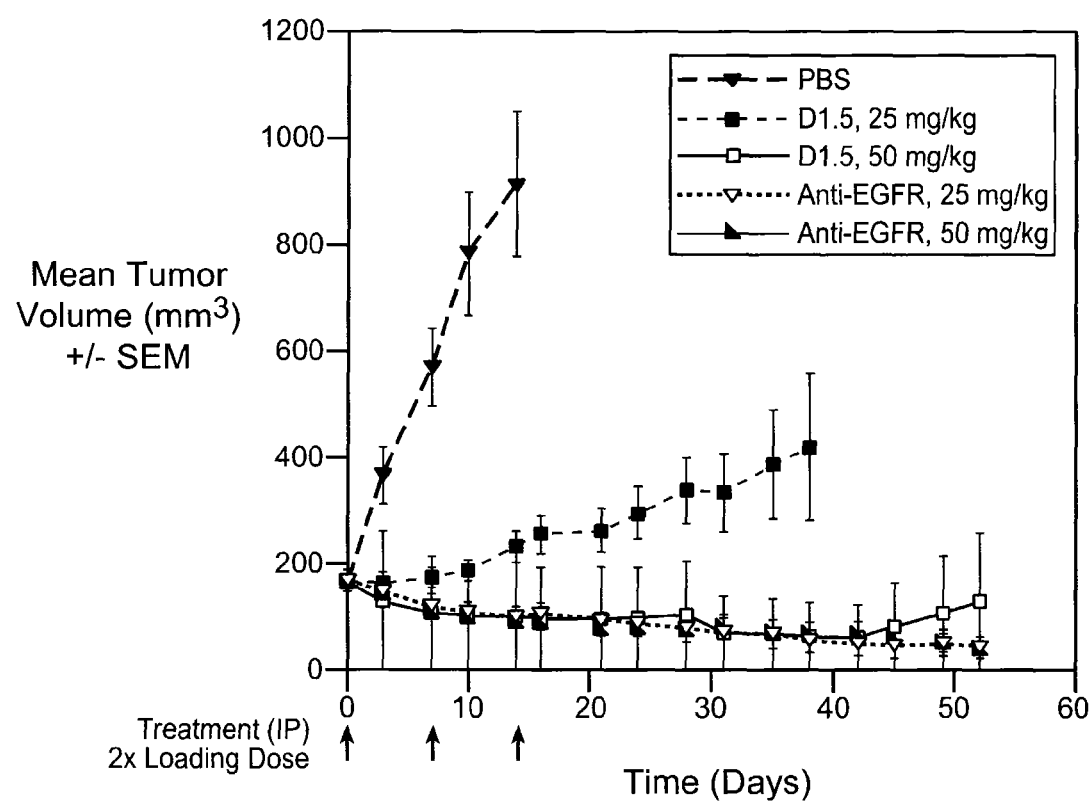
FIG. 1 shows inhibition of tumor growth by anti-EGFR antibody D1.5 in an A431 xenograft model.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

Before the present methods, kits and uses therefore are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise.

Throughout this specification and claims, the word "comprise," or variations such as "comprises" or "comprising," will be understood to imply the inclusion of a stated integer or group of integers but not the exclusion of any other integer or group of integers.

The term "antibody" herein is used in the broadest sense and specifically covers monoclonal antibodies, polyclonal antibodies, multispecific antibodies, and antibody fragments so long as they exhibit the desired biological activity. The term "multispecific antibody" is used in the broadest sense and specifically covers an antibody comprising an antigen-binding domain that has polyepitopic specificity (i.e., is capable of specifically binding to two, or more, different epitopes on one biological molecule or is capable of specifically binding to epitopes on two, or more, different biological molecules). One specific example of an antigen-binding domain is a $V_H V_L$ unit comprised of a heavy chain variable domain ($V_H$) and a light chain variable domain ($V_L$). Such multispecific antibodies include, but are not limited to, full length antibodies, antibodies having two or more $V_L$ and $V_H$ domains, antibody fragments such as Fab, Fv, dsFv, scFv, diabodies, bispecific diabodies and triabodies, antibody fragments that have been linked covalently or non-covalently. A "bispecific antibody" is a multispecific antibody comprising an antigen-binding domain that is capable of specifically binding to two different epitopes on one biological molecule or is capable of specifically binding to epitopes on two different biological molecules. The bispecific antibody is also referred to herein as having "dual specificity" or as being "dual specific".

In certain embodiments, an antibody of the invention has a dissociation constant (Kd) of ≤1 M, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M) for its target HER or HERs.

The basic 4-chain antibody unit is a heterotetrameric glycoprotein composed of two identical light (L) chains and two identical heavy (H) chains (an IgM antibody consists of 5 of the basic heterotetramer units along with an additional polypeptide called J chain, and therefore contains 10 antigen-binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has, at the N-terminus, a variable domain ($V_H$) followed by three constant domains ($C_H$) for each of the α and γ chains and four $C_H$ domains for μ and ε isotypes. Each L chain has, at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H 1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology,* 8th edition, Daniel P. Stites, Abba I. Ten and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, γ, ε, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen-binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called hypervariable regions" or HVR. The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region," "HVR," or "HV," when used herein refers to the regions of an antibody variable domain which are hypervariable in sequence and/or form structurally defined loops. Generally, antibodies comprise six HVRs; three in the VH (HVR-H1, HVR-H2, HVR-H3), and three in the VL (HVR-L1, HVR-L2, HVR-L3). In native antibodies, H3 and L3 display the most diversity of the six HVRs, and H3 in particular is believed to play a unique role in conferring fine specificity to antibodies. See, e.g., Xu et al., Immunity 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

HVRs generally comprise amino acid residues from the hypervariable loops and/or from the "complementarity determining regions" (CDRs), the latter being of highest sequence variability and/or involved in antigen recognition. A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 47-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g, Kabat et al., *Sequences of Immunological Interest*. 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system (e.g., see WO 2006/073941).

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein.

An "affinity matured" antibody is one with one or more alterations in one or more HVRs or framework region thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. Bio/Technology 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term "monoclonal antibody" as used herein refers to an antibody from a population of substantially homogeneous antibodies, i.e., the individual antibodies comprising the population are substantially similar and bind the same epitope(s), except for possible variants that may arise during production of the monoclonal antibody, such variants generally being present in minor amounts. Such monoclonal antibody typically includes an antibody comprising a variable region that binds a target, wherein the antibody was obtained by a process that includes the selection of the antibody from a plurality of antibodies. For example, the selection process can be the selection of a unique clone from a plurality of clones, such as a pool of hybridoma clones, phage clones or recombinant DNA clones. It should be understood that the selected antibody can be further altered, for example, to improve affinity for the target, to humanize the antibody, to improve its production in cell culture, to reduce its immunogenicity in vivo, to create a multispecific antibody, etc., and that an antibody comprising the altered variable region sequence is also a monoclonal antibody of this invention. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340(5): 1073-1093 (2004); Fellouse, Proc. Nat. Acad. Sci. USA 101 (34):12467-12472 (2004); and Lee et al. J. Immunol. Methods 284(1-2):119-132 (2004) and technologies for producing human or human-like antibodies from animals that have parts or all of the human immunoglobulin loci or genes encoding human immunoglobulin sequences (see, e.g., WO98/24893, WO/9634096, WO/9633735, and WO/91 10741, Jakobovits et al., Proc. Natl. Acad. Sci. USA, 90:2551 (1993); Jakobovits et al., Nature, 362:255-258 (1993); Bruggemann et al., Year in Immuno., 7:33 (1993); U.S. Pat. Nos. 5,545,806, 5,569,825, 5,591,669 (all of GenPharm); 5,545,807; WO 97/17852, U.S. Pat. Nos. 5,545,807; 5,545,806; 5,569,825; 5,625,126; 5,633, 425; and 5,661,016, and Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995).

An "intact" antibody is one which comprises an antigen-binding site as well as a $C_L$ and at least heavy chain constant domains, $C_H1$, $C_H2$, and $C_H3$. The constant domains can be native sequence constant domains (e.g., human native sequence constant domains) or amino acid sequence variant thereof. Preferably, the intact antibody has one or more effector functions.

"Antibody fragments" comprise a portion of an intact antibody, preferably the antigen-binding or variable region of the intact antibody. Examples of antibody fragments include Fv, Fab, Fab', F(ab')$_2$, Fab'-SH; diabodies; linear antibodies (see U.S. Pat. No. 5,641,870, Example 2; Zapata et al., Protein Eng. 8(10): 1057-1062 (1995)); single-chain antibody molecules (e.g. scFv). While in the present description, and throughout the specification, reference is made to antibodies and various properties of antibodies, the same disclosure also applies to functional antibody fragments, e.g. dual action Fab fragments.

The expression "linear antibodies" generally refers to the antibodies described in Zapata et al., Protein Eng., 8(10): 1057-1062 (1995). These antibodies comprise a pair of tandem Fd segments ($V_H$-$C_H1$-$V_H$-$C_H1$) which, together with complementary light chain polypeptides, form a pair of antigen-binding regions. In a preferred embodiment, the fragment is "functional," i.e. qualitatively retains the ability of the corresponding intact antibody to bind to the target HER receptor and, if the intact antibody also inhibits HER activation or function, qualitatively retains such inhibitory property as well. Qualitative retention means that the activity in kind is retained, but the degree of binding affinity and/or activity might differ.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region; this region is also the part recognized by Fc receptors (FcR) found on certain types of cells.

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen-binding and confer antigen-binding specificity to the antibody. However, even a single variable domain (or half of an Fv comprising only three HVRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen-binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites.

Diabodies are described more fully in, for example, EP 404, 097; WO 93/11161; and Hollinger et al., Proc. Natl. Acad. Sci. USA, 90:6444-6448 (1993).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

An antibody of this invention "which binds" an antigen of interest is one that binds the antigen with sufficient affinity such that the antibody is useful as a diagnostic and/or therapeutic agent in targeting a protein or a cell or tissue expressing the antigen. With regard to the binding of a antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess non-labeled target. In one particular embodiment, "specifically binds" refers to binding of an antibody to its specified target HER receptors and not other specified non-target HER receptors. For example, the antibody specifically binds to EGFR and HER3 but does not specifically bind to HER2 or HER4, or the antibody specifically binds to EGFR and HER2 but does not specifically bind to HER3 or HER4, or the antibody specifically binds to EGFR and HER4 but does not specifically bind to HER2 or HER3.

A "HER receptor" is a receptor protein tyrosine kinase which belongs to the HER receptor family and includes EGFR (ErbB1, HER1), HER2 (ErbB2), HER3 (ErbB3) and HER4 (ErbB4) receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is a native sequence human HER receptor.

The "HER pathway" refers to the signaling network mediated by the HER receptor family.

The terms "ErbB1", "HER1", "epidermal growth factor receptor" and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Ullrich et al, Nature (1984) 309:418425 and Humphrey et al. *PNAS (USA)* 87:4207-4211 (1990)), as well we variants thereof, such as EGFRvIII. Variants of EGFR also include deletional, substitutional and insertional variants, for example those described in Lynch et al (New England Journal of Medicine 2004, 350:2129), Paez et al (Science 2004, 304: 1497), and Pao et al (PNAS 2004, 101:13306).

Herein, "EGFR extracellular domain" or "EGFR ECD" refers to a domain of EGFR that is outside of a cell, either anchored to a cell membrane, or in circulation, including fragments thereof. In one embodiment, the extracellular domain of EGFR may comprise four domains: "Domain I" (amino acid residues from about 1-158, "Domain II" (amino acid residues 159-336), "Domain III" (amino acid residues 337-470), and "Domain IV" (amino acid residues 471-645), where the boundaries are approximate, and may vary by about 1-3 amino acids.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (GenBank accession number X03363). The term "erbB2" refers to the gene encoding human HER2 and "neu" refers to the gene encoding rat p185$^{neu}$. Preferred HER2 is native sequence human HER2.

Herein, "HER2 extracellular domain" or "HER2 ECD" refers to a domain of HER2 that is outside of a cell, either anchored to a cell membrane, or in circulation, including fragments thereof. In one embodiment, the extracellular domain of HER2 may comprise four domains: "Domain I" (amino acid residues from about 1-195, "Domain II" (amino acid residues from about 196-319), "Domain III" (amino acid residues from about 320-488), and "Domain IV" (amino acid residues from about 489-630) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), and Plowman et al. *Proc. Natl. Acad. Sci.* 90:1746-1750 (1993).

"ErbB3" and "HER3" refer to the receptor polypeptide as disclosed, for example, in U.S. Pat. Nos. 5,183,884 and 5,480,968 as well as Kraus et al. *PNAS (USA)* 86:9193-9197 (1989).

Herein, "HER3 extracellular domain" or "HER3 ECD" refers to a domain of HER3 that is outside of a cell, either anchored to a cell membrane, or in circulation, including fragments thereof. In one embodiment, the extracellular domain of HER3 may comprise four domains: Domain I, Domain II, Domain III, and Domain IV. In one embodiment, the HER3 ECD comprises amino acids 1-636 (numbering including signal peptide). In one embodiment, HER3 domain III comprises amino acids 328-532 (numbering including signal peptide.

The terms "ErbB4" and "HER4" herein refer to the receptor polypeptide as disclosed, for example, in EP Pat Appln No 599,274; Plowman et al., *Proc. Natl. Acad. Sci. USA,* 90:1746-1750 (1993); and Plowman et al., *Nature,* 366:473-475 (1993), including isoforms thereof, e.g., as disclosed in WO99/19488, published Apr. 22, 1999.

By "HER ligand" is meant a polypeptide which binds to and/or activates a HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)); and cripto (CR-1) (Kannan et al. *J. Biol. Chem.* 272(6):3330-3335 (1997)). HER ligands which bind EGFR include EGF, TGF-, amphiregulin, betacellulin, HB-EGF and epiregulin. HER ligands which bind HER3 include heregulins and NRG-2. HER ligands capable of binding HER4 include betacellulin, epiregulin, HB-EGF, NRG-2, NRG-3, NRG-4, and heregulins.

"Heregulin" (HRG) when used herein refers to a polypeptide encoded by the heregulin gene product as disclosed in U.S. Pat. No. 5,641,869, or Marchionni et al., *Nature,* 362: 312-318 (1993). Examples of heregulins include heregulin-, heregulin-1, heregulin-2 and heregulin-3 (Holmes et al., *Science,* 256:1205-1210 (1992); and U.S. Pat. No. 5,641,869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); -heregulin (Schaefer et al. *Oncogene* 15:1385-1394 (1997)).

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.,* 269(20):14661-14665 (1994), for example. Other proteins, such as a cytokine receptor subunit (e.g. gp130) may be associated with the dimer.

A "HER heterodimer" herein is a noncovalently associated heterodimer comprising at least two different HER receptors, such as EGFR-HER2, EGFR-HER3, EGFR-HER4, HER2-HER3 or HER2-HER4 heterodimers.

A "HER inhibitor" is an agent which interferes with HER activation or function. Examples of HER inhibitors include HER antibodies (e.g. EGFR, HER2, HER3, or HER4 antibodies); EGFR-targeted drugs; small molecule HER antagonists; HER tyrosine kinase inhibitors; HER2 and EGFR dual tyrosine kinase inhibitors such as lapatinib/GW572016; antisense molecules (see, for example, WO2004/87207); and/or agents that bind to, or interfere with function of, downstream signaling molecules, such as MAPK or Ala. Preferably, the HER inhibitor is an antibody which binds to a HER receptor.

A "HER dimerization inhibitor" or "HDI" is an agent which inhibits formation of a HER homodimer or HER heterodimer. Preferably, the HER dimerization inhibitor is an antibody. However, HER dimerization inhibitors also include peptide and non-peptide small molecules, and other chemical entities which inhibit the formation of HER homo- or heterodimers.

An antibody which "inhibits HER dimerization" is an antibody which inhibits, or interferes with, formation of a HER dimer, regardless of the underlying mechanism. In one embodiment, such an antibody binds to HER2 at the heterodimeric binding site thereof. One particular example of a dimerization inhibiting antibody is pertuzumab (Pmab), or MAb 2C4. Other examples of HER dimerization inhibitors include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; antibodies which bind to HER4 and inhibit dimerization thereof with one or more other HER receptors; peptide dimerization inhibitors (U.S. Pat. No. 6,417,168); antisense dimerization inhibitors; etc.

As used herein, "EGFR antagonist" or "EGFR inhibitor" refer to those compounds that specifically bind to EGFR and prevent or reduce its signaling activity, and do not specifically bind to HER2, HER3, or HER4. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al., *J. Biol. Chem.* 279(29):30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI-1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N-8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyeamino]-7H-pyrrolo[2,3-d]pyrimidine); CL-387785 (N-[4-[(3-bromophenyeamino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Sugen); and AG1571 (SU 5271; Sugen).

A "HER antibody" is an antibody that binds to a HER receptor. Optionally, the HER antibody further interferes with HER activation or function. Particular HER2 antibodies include pertuzumab and trastuzumab. Examples of particular EGFR antibodies include cetuximab and panitumumab.

Patent publications related to HER antibodies include: U.S. Pat. Nos. 5,677,171, 5,720,937, 5,720,954, 5,725,856, 5,770,195, 5,772,997, 6,165,464, 6,387,371, 6,399,063, US2002/0192211A1, U.S. Pat. Nos. 6,015,567, 6,333,169, 4,968,603, 5,821,337, 6,054,297, 6,407,213, 6,719,971, 6,800,738, US2004/0236078A1, U.S. Pat. Nos. 5,648,237, 6,267,958, 6,685,940, 6,821,515, WO98/17797, U.S. Pat. Nos. 6,333,398, 6,797,814, 6,339,142, 6,417,335, 6,489,447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. Nos. 6,627,19681, 6,632,97981, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. Nos. 5,985,553, 5,747,261, 4,935,341, 5,401,638, 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. Nos. 5,571,894, 5,939,531, EP 502,812 B1, WO 93/03741, EP 554,441 B1, EP 656,367 A1, U.S. Pat. Nos. 5,288,477, 5,514,554, 5,587,458, WO 93/12220, WO 93/16185, U.S. Pat. No. 5,877,305, WO 93/21319, WO 93/21232, U.S. Pat. No. 5,856,089, WO 94/22478, U.S. Pat. Nos. 5,910,486, 6,028,059, WO 96/07321, U.S. Pat. Nos. 5,804,396, 5,846,749, EP 711,565, WO 96/16673, U.S. Pat. Nos. 5,783,404, 5,977,322, 6,512,097, WO 97/00271, U.S. Pat. Nos. 6,270,765, 6,395,272, 5,837,243, WO 96/40789, U.S. Pat. Nos. 5,783,186, 6,458,356, WO 97/20858, WO 97/38731, U.S. Pat. Nos. 6,214,388, 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. Nos. 5,705,157, 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842 and WO 03/86467.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"Phosphorylation" refers to the addition of one or more phosphate group(s) to a protein, such as a HER receptor, or substrate thereof.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2. Franklin et al. *Cancer Cell* 5:317-328 (2004).

A HER2 antibody that "binds to a heterodimeric binding site" of HER2, binds to residues in domain II (and optionally also binds to residues in other of the domains of the HER2 extracellular domain, such as domains I and III), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II and optionally residues in other domain(s) of HER2, such as domains I and III.

"Isolated," when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step. In some embodiments, the multispecific anti-HER antibody is an isolated antibody.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, can be identified by those that: (1) employ low ionic strength and high temperature for washing, for example 0.015 M sodium chloride/0.0015 M sodium citrate/0.1% sodium dodecyl sulfate at 50 C; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) overnight hybridization in a solution that employs 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS, and 10% dextran sulfate at 42° C., with a 10 minute wash at 42° C. in 0.2×SSC (sodium chloride/sodium citrate) followed by a 10 minute high-stringency wash consisting of 0.1×SSC containing EDTA at 55° C.

"Moderately stringent conditions" can be identified as described by Sambrook et al., *Molecular Cloning: A Laboratory Manual*, New York: Cold Spring Harbor Press, 1989, and include the use of washing solution and hybridization conditions (e.g., temperature, ionic strength, and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express Fc RIII only, whereas monocytes express Fc RI, Fc RII, and Fc RIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al. (Proc. Natl. Acad. Sci. USA) 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the Fc RI, Fc RII, and Fc RIII subclasses, including allelic variants and alternatively spliced forms of these receptors. Fc RII receptors include Fc RIIA (an "activating receptor") and Fc RIIB (an "inhibiting receptor"), which have similar amino acid sequences that differ primarily in the cytoplasmic domains thereof. Activating receptor Fc RIIA contains an immunoreceptor tyrosine-based activation motif (ITAM) in its cytoplasmic domain. Inhibiting receptor Fc RIIB contains an immunoreceptor tyrosine-based inhibition motif (ITIM) in its cytoplasmic domain (see review M. in Daeron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes which express one or more FcRs and perform effector functions. Preferably, the cells express at least Fc RIII and perform ADCC effector function. Examples of human leukocytes which mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., J. Immunol. Methods 202:163 (1996), can be performed.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "therapeutically effective amount" refers to an amount of an antibody or antibody fragment to treat a disease or disorder in a subject. In the case of tumor (e.g., a cancerous tumor), the therapeutically effective amount of the antibody or antibody fragment may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The terms "cancer" and "cancerous" refer to or describe the physiological condition in mammals that is typically characterized by unregulated cell growth. Included in this definition are benign and malignant cancers. By "early stage cancer" is meant a cancer that is not invasive or metastatic or is classified as a Stage 0, I, or II cancer.

The term "precancerous" refers to a condition or a growth that typically precedes or develops into a cancer.

By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "anti-cancer therapy" refers to a therapy useful in treating cancer. Examples of anti-cancer therapeutic agents include, but are limited to, e.g., chemotherapeutic agents, growth inhibitory agents, cytotoxic agents, agents used in radiation therapy, anti-angiogenesis agents, apoptotic agents, anti-tubulin agents, and other agents to treat cancer, anti-CD20 antibodies, platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets EGFR, ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Nicolaou et al., *Angew. Chem Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2'-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chlorambucil; 6-thioguanine; mercaptopurine; methotrexate; platinum agents such as cisplatin, oxaliplatin (e.g., ELOXATIN®), and carboplatin; vincas, which prevent tubulin polymerization from forming microtubules, including vinblastine (VELBAN®), vincristine (ONCOVIN®), vindesine (ELDISINE®, FILDESIN®), and vinorelbine (NAVELBINE®); etoposide (VP-16); ifosfamide; mitoxantrone; leucovorin; novantrone; edatrexate; daunomycin; aminopterin; ibandronate; topoisomerase inhibitor RFS 2000; difluoromethylornithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); BAY439006 (sorafenib; Bayer); SU-11248 (sunitinib, SUTENT®, Pfizer); perifosine, COX-2 inhibitor (e.g. celecoxib or etoricoxib), proteosome inhibitor (e.g. PS341); bortezomib (VELCADE®); CCI-779; tipifarnib (R11577); orafenib, ABT510; Bcl-2 inhibitor such as oblimersen sodium (GENASENSE®); pixantrone; EGFR inhibitors (see definition below); tyrosine kinase inhibitors (see definition below); serine-threonine kinase inhibitors such as rapamycin (sirolimus, RAPAMUNE®); farnesyl-transferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents as defined herein include "antihormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

A "subject" is a vertebrate, preferably a mammal, more preferably a human. Mammals include, but are not limited to, humans, non-human higher primates, primates, farm animals (such as cows), sport animals, pets (such as cats, dogs and horses), and laboratory animals (such as mice and rats).

II. Detailed Description

The present invention provides antibodies, and functional antibody fragments, comprising at least one antigen-binding domain that has binding specificity for at least two different HER receptors, in particular EGFR and HER2, EGFR and HER3, or EGFR and HER4. These multispecific antibodies are distinct from traditional multispecific antibodies which have antigen-binding domains (usually two) with different binding specificities. In certain embodiments, the multispecific antibodies described herein have the molecular structure of an IgG (or Fab) and thus retain favorable attributes of an IgG for therapeutic development, such as predictable pharmacokinetic properties, well established manufacturing protocols, choice of Fc-mediated effector functions, and bi- or mono-valencies. These favorable attributes are often lacking in the traditional multispecific antibodies that are derived by assembling two distinct antibody fragments into one molecule.

The multispecific antibodies described herein, and functional antibody fragments thereof, are useful for the treatment of diseases or conditions, such as cancers, that are associated with HER receptor pathways. In one particular embodiment, the antigen-binding domain of the multispecific antibody specifically binds to both EGFR and HER3. In another embodiment, the antigen-binding domain specifically binds to both EGFR and HER2. In another embodiment, the antigen-binding domain specifically binds to both EGFR and HER4.

One particular aspect of the invention provides for antibodies comprising two (or more) antigen-binding domains, each of which has the same binding specificity.

One embodiment provides for a multispecific antibody comprised of two antigen-binding domains, where each antigen-binding domain has the same specificity and specifically binds to two different HER receptors. In one particular embodiment, each antigen-binding domain specifically binds to both EGFR and HER3. In another embodiment, each antigen-binding domain specifically binds to both EGFR and HER2. In another embodiment, each antigen-binding domain specifically binds to both EGFR and HER4. In yet another embodiment, each antigen-binding domain specifically binds to Domain III of EGFR. In another embodiment, each antigen-binding domain specifically binds to Domain III of HER3. In yet another embodiment, each antigen-binding domain is capable of binding to Domain III of EGFR and Domain III of HER3.

In particular embodiments, the multispecific antibody specifically binds to its target HER receptor or HER receptors and does not specifically bind to the non-target HER receptors. Accordingly, in one embodiment, the multispecific antibody specifically binds to EGFR and HER3 but does not specifically bind to HER2 or HER4. In another embodiment, the multispecific antibody specifically binds to EGFR and HER2 but does not specifically bind to HER3 or HER4. In another embodiment, the multispecific antibody specifically binds to EGFR and HER4 but does not specifically bind to HER2 or HER3.

In certain embodiments, each antigen-binding domain comprises a heavy chain variable domain ($V_H$) and a light chain variable domain ($V_L$). In one embodiment, the $V_H V_L$ unit specifically binds to two different HER receptors. In one particular embodiment, the $V_H V_L$ unit specifically binds to EGFR and HER3. In another embodiment, the $V_H V_L$ unit specifically binds to EGFR and HER2. In another embodiment, the $V_H V_L$ unit specifically binds to EGFR and HER4.

In particular embodiments, the affinity of the multispecific antibody for its target HER receptor or receptors is indicated by a Kd of less than $10^{-5}$ M, less than $10^{-6}$ M, less than $10^{-7}$ M, less than $10^{-8}$ M, less than $10^{-9}$ M, less than $10^{-10}$ M, less than $10^{-11}$ M, or less than $10^{-12}$ M. In one embodiment, the Kd of the antibody for one of its target receptors is less than $10^{-7}$ M, less than $10^{-8}$ M, less than $10^{-9}$ M, less than $10^{-10}$ M, less than $10^{-11}$ M, or less than $10^{-12}$ M. In another embodiment, the Kd of the multispecific antibody for all of its target receptors is less than $10^{-7}$ M, less than $10^{-8}$ M, less than $10^{-9}$ M, less than $10^{-10}$ M, a less than $10^{-11}$ M, or less than $10^{-12}$ M.

In some embodiments, the affinity of the multispecific antibody for one of its target HER receptors is greater than for its other target HER receptor or receptors. In one embodiment, the affinity of the multispecific antibody for one target HER receptor is at least 2, 3, 4, 5, 8, 10, 12, 15, 18, 20, 22, 25, 30, 35, 40, 50, 100-fold greater than its affinity for another target HER receptor. In one embodiment, the multispecific antibody specifically binds to EGFR and another HER receptor and its binding affinity for the other HER receptor is at least 2, 3, 4, 5, 8, 10, 12, 15, 18, 20, 22, 25, 30, 35, 40, 50, or 100-fold greater than its affinity for EGFR. In one embodiment, the multispecific antibody specifically binds to EGFR and HER3 and its binding affinity for HER3 is at least 2, 3, 4, 5, 8, 10, 12, 15, 18, 20, 22, 25, 30, 35, 40, 50, or 100-fold greater than its binding affinity for EGFR. In another embodiment, the multispecific antibody specifically binds to EGFR and HER2 and its binding affinity for HER2 is at least 2, 3, 4, 5, 8, 10, 12, 15, 18, 20, 22, 25, 30, 35, 40, 50, or 100-fold greater than its binding affinity for EGFR. In another embodiment, the multispecific antibody specifically binds to EGFR and HER4 and its binding affinity for HER4 is at least 2, 3, 4, 5, 8, 10, 12, 15, 18, 20, 22, 25, 30, 35, 40, 50, or 100-fold greater than its affinity for EGFR.

In some embodiments, the multispecific antibodies of the present invention inhibit a biological activity of at least one of the HER receptors to which they specifically bind. In some embodiments, the multispecific antibodies of the present invention inhibit a biological activity of both of the HER receptors to which specifically they bind. Thus, for example, a multispecific antibody of the invention inhibits a biological activity of an EGFR and/or HER2 and/or HER3 and/or HER4 receptor.

In one embodiment, the multispecific antibody specifically binds human EGFR and human HER3, and inhibits a biological activity of at least the EGFR. In another embodiment, the multispecific antibody specifically binds human EGFR and human HER3 and inhibits at least a biological activity of HER3. In another embodiment, the multispecific antibody specifically binds human EGFR and human HER3 and inhibits a biological activity of both EGFR and HER3.

In another embodiment, the multispecific antibody specifically binds human EGFR and human HER2 and inhibits at least a biological activity of EGFR. In yet another embodiment, the antibody specifically binds human EGFR and human HER2 and inhibits at least a biological activity of HER2. In yet another embodiment, the antibody specifically binds human EGFR and human HER2 and inhibits a biological activity of both EGFR and HER2.

In another embodiment, the antibody specifically binds human EGFR and human HER4, and inhibits a biological activity of at least the EGFR. In another embodiment, the antibody specifically binds human EGFR and human HER4 and inhibits at least a biological activity of HER4. In another embodiment, the antibody specifically binds human EGFR and human HER4 and inhibits a biological activity of both EGFR and HER4.

In certain embodiments, the antibodies herein inhibit a biological activity driven, at least partially, by a HER receptor to which they do not bind. For example, antibodies that bind EGFR and HER3 might still be able to inhibit a HER2-driven biological activity.

Inhibition of a biological activity can be measured in assays well known in the art. Thus, for example, the antibodies herein may inhibit phosphorylation of one or more of the HER receptors, and/or may inhibit the binding of a HER ligand to its receptor, and/or may inhibit ligand induced proliferation of HER receptor expressing cells and/or may inhibit downstream signaling pathways that are activated via a HER receptor.

Two major downstream signaling pathways that are activated in response to EGFR phosphorylation are the Ras/MAPK and the phosphatidylinositol 3-kinase (PI3K)/Akt pathways. Therefore, the ability of an antibody herein to inhibit the biological activity of a HER receptor can be measured by assessing whether it can block the activation of these pathways, for example in NR6 cells. Thus, the ability of the antibodies to block ligand induced phosphorylation of p44/42MAPK, pAKT or other downstream signaling molecules can be measured. HER3 signaling has also been implicated in several other pathways, including c-met and FGFR. The ability of an antibody herein to inhibit the biological activity of a HER receptor can be measured by assessing whether it can block the activation of these pathways.

One aspect of invention provides for multispecific antibodies that are generated by diversifying an antibody with specificity for one HER receptor such that it develops specificity for a second HER receptor while retaining specificity for the first HER receptor. In generic terms, this method comprises the steps of (1) diversifying the amino acid sequence of a light chain variable domain ($V_L$) of an antibody, wherein prior to the diversification, the antibody comprised a $V_L$ and a heavy chain variable domain ($V_H$) capable of binding to an epitope on a first HER receptor and (2) selecting a diversified antibody capable of binding to the epitope on the first HER receptor and an epitope on a second HER receptor. These steps can be repeated in order to generate multi-specific antibodies. A detailed description of this method is provided in United States Patent Publication No. 20080069820, the entire disclosure of which is expressly incorporated by reference herein. This method is further illustrated in the Examples. In the method described in the Examples, an anti-EGFR antibody is used as a template for diversification and thus for the preparation of multispecific anti-HER antibodies, however, other anti-HER antibodies, such as anti-HER2, anti-HER3, or anti-HER4 antibodies could also serve as a template.

The invention further provides for monospecific antibodies that are capable of specifically binding to one HER receptor and do not specifically bind to the other HER receptors. In one embodiment, the antibody specifically binds to EGFR. In one embodiment, the antibody specifically binds to Domain III of EGFR. In some embodiments, the antibody specifically binds to EGFR and inhibits a biological activity of EGFR. In another embodiment, the antibody specifically binds to HER3. In one embodiment, the antibody specifically binds to Domain III of HER3. In some embodiments, the antibody specifically binds to HER3 and inhibits a biological activity of HER3.

The monospecific antibodies can be used as the template antibody for further diversification to add binding specificity to other HER receptors or to other target antigens.

Toxicity

Toxicity of EGFR antagonists is well documented in both pre-clinical and clinical studies. For example, the anti-EGFR antibody cetuximab exhibits various forms of toxicity at therapeutically effective levels. The most common adverse reactions with cetuximab (ERBITUX®, Imclone) (incidence ≥25%) are cutaneous adverse reactions (including rash, pruritus, and nail changes), headache, diarrhea, and infection. The most serious adverse reactions associated with cetuximab treatment are infusion reactions, cardiopulmonary arrest, dermatologic toxicity and radiation dermatitis, sepsis, renal failure, interstitial lung disease, and pulmonary embolus. See, Biologics License Agreement (BLA) for cetuximab (Application No.: 125084) (incorporated by reference herein). Similar toxicity issues are observed for panitumumab (VECTIBIX® Amgen) where dermatologic toxicity occurred in 89% of patients administered this antibody. These toxicities were severe, CTC grade 3 and higher. (VECTIBIX® FDA label.)

The anti-EGFR chemotherapeutic agent erlotinib has been reported to cause, in some instances, acute renal failure or renal insufficiency, hepatic failure and/or hepatorenal syndrome, gastrointestinal perforations, bullous and exfoliative skin disorders, and corneal ulceration and perforation. See, FDA Warnings and Precautions safety labeling for erlotinib (TARCEVA®, Genentech, OSI Pharmaceuticals) (2009).

"Toxic", or "toxicity", refers to any adverse effect caused by an agent when administered to a subject. Measures of toxicity include, but are not limited to, mortality, loss of body weight, organ failure, altered organ function, central nervous system toxicity, gastrointestinal toxicity (as indicated, for example, by diarrhea), dermatologic toxicity (as indicated, for example, by appearance of rash, skin lesion, desquamation, or pruritus), cardiac toxicity, infection, sepsis, and cytotoxicity.

Toxicity can be determined by methods known in the art such as monitoring clinical cage side observations, body weight, food consumption, respiration rate, pulse oximetry measurements, physical examination, ophthalmic evaluations, neurological evaluations, metabolic parameters, cardiovascular parameters, clinical pathology (including clinical chemistry, hematology, urinalysis and coagulation parameters), and macroscopic and microscopic pathology.

The Common Terminology Criteria for Adverse Events v3.0 (CTCAE) prepared by the National Cancer Institute (incorporated by reference in its entirety herein) provides information regarding particular accepted indicators of toxicity in human subjects. FIG. 31 provides information regarding observed non-clinical and clinical toxicities for EGFR antagonist therapies.

Toxicity can be measured in terms of total toxic events or severity of the toxic event/events. Severity of the events can be described using the grading system set up in the CTCAE. Grades are assigned each adverse event using unique clinical descriptions of severity based on the general guideline that Grade 1 refers to a mild event, Grade 2 refers to a moderate event, Grade 3 refers to a severe event, Grade 4 refers to a life-threatening or disabling event, and Grade 5 refers to a death related to the event. The CTCAE provides the specific clinical descriptions for the toxic events. The descriptors for dermatologic toxicity are provided beginning at page 14 of the CTCAE, v.3. As an example, FIG. 32 shows grading for rash/desquamation and acne/acneiform rash. (CTCAE, v.3) There are a number of models known in the art that are used to monitor for potential indicators of toxicity, including, but not limited to, in vitro cell-based models and in vivo non-human animal models. Toxicity is also monitored in human subjects in clinical trial studies.

In one particular embodiment, toxicity is measured in cynomolgus monkeys. The toxic effect of EGFR antagonists in cynomolgus monkeys is well documented. As set forth in the Biologics License Agreement (BLA) for cetuximab (Application No.: 125084) (incorporated by reference herein), all monkeys receiving cetuximab exhibited mild to severe lesions on the skin, consisting of scale formation, reddening, erythema, dermatitis, fissures, wounds, and exanthema, and/or hair thinning or loss. The dermatologic toxicity was dose-dependent in both severity and time of onset, where severity for high, mid and low doses were severe, moderate and mild and time of onset occurred on Study Days 15, 22 and 64, respectively. Secondary complications of severe skin lesions were bacterial infection or sepsis with subsequent mortality or euthanasia of 50% of the animals in the high dose group. Other dose-related toxicities included changes in certain clinical pathology parameters associated with macroscopic and microscopic evidence of cellular and tissue damage in the liver, bone marrow, spleen, and lymphoid organs.

As set forth in the Examples, cynomolgus monkeys dosed with a bispecific antibody that specifically binds to EGFR and HER3 exhibited fewer incidences of toxicity, as indicated by dermal lesions, as compared to cynomolgus monkeys dosed with an equal amount of the EGFR antagonist cetuximab. One of three cynomolgus monkeys dosed with 25 mg/kg of the bispecific antibody developed dermal lesions whereas 3 of 3 cynomolgus monkeys dosed with 25 mg/kg of cetuximab developed dermal lesions. The lesion that occurred in a bispecific antibody dosed monkey was less severe than the lesions of the cetuximab dosed monkeys and the onset of the lesion was delayed. The animal dosed with the bispecific antibody developed the skin lesion one week after the last (sixth) dose compared to the monkeys dosed with cetuximab where the onset of dermal lesions occurred after the third dose in all animals.

In clinical studies of cetuximab, dermatologic toxicities, including acneiform rash, skin drying and fissuring, and inflammatory and infectious sequelae were observed. The reported incidence of dermatologic toxicity was as high as 89% (for those patients with advanced colorectal cancer).

Models of skin toxicity are known and can be used to determine dermatologic toxicity of the antibodies. Examples of such models include human epidermal keratinocytes (NHEK (Clonetics, San Diego, Calif.; Lonza Bioscience, Walkersville, Md.); HEKa (Cascade Biologics, Portland, Oreg.; Invitrogen, Carlsbad, Calif.) and reconstituted human epidermis (EpiDerm™ cultures (MatTek, Ashland, Mass.). These models can be used to examine the effect of the antibodies on cellular proliferation, gene expression, protein expression, receptor phosphorylation, cell viability, and changes in histopathology. Lacouture, M. E., *Nature Rev. Cancer*, 6:803-812 (2006).

It is desirable to provide a less toxic antibody that targets the EGFR pathway. Dosing of EGFR antagonists such as cetuximab is limited by toxicity (primarily dermatologic toxicity and infusion reactions). A less toxic antibody could be administered at a higher dose than a more toxic EGFR antagonist which may result in increased antitumor effects. Accordingly, one aspect of the invention provides a multispecific antibody that specifically binds to EGFR and at least one other HER receptor, (HER2, HER3, and/or HER4), where the antibody is less toxic than an EGFR antagonist when the antibody and EGFR antagonist are administered at equivalent doses. In one embodiment, the antibody specifically binds to EGFR and HER3. In another embodiment, the antibody specifically binds to EGFR and HER2. In yet another embodiment, the antibody specifically binds to EGFR and HER4.

In some embodiments the multispecific antibody induces a lower incidence of toxicities, less severe toxicities, or delayed onset of toxicities in an in vivo model compared to an EGFR antagonist. One aspect of the invention provides for a multi-specific antibody that specifically binds to EGFR and at least one other HER receptor (HER2, HER3, and/or HER4) where the antibody induces fewer toxicity incidents in subjects administered the antibody as compared to toxicity incidents in subjects administered an EGFR antagonist. In particular embodiments, the number of toxicity incidents in subjects administered the antibody is at least 10%, 20%, 30%, 40%, 50%, 60%, 70%, 80%, or 90% less than the number of toxicity incidents in subjects administered an EGFR antagonist.

In other embodiments, the rate of toxicity incidents in subjects administered the antibody is less than 80%, 70%, 60%, 50%, 40%, 30%, 20%, 10%, 5%, 2%, or 1%.

In particular embodiments the multispecific antibody induces a lower incidence of dermatologic toxicities, less severe dermatologic toxicities, or delayed onset of dermatologic toxicities in an in vivo model compared to an EGFR antagonist. One aspect of the invention provides for a multi-specific antibody that specifically binds to EGFR and at least one other HER receptor (HER2, HER3, and/or HER4) where the antibody induces fewer total dermatologic toxicity incidents in subjects administered the antibody as compared to total dermatologic toxicity incidents in subjects administered an EGFR antagonist. In particular embodiments, the number of total dermatologic toxicity incidents in subjects administered the antibody is at least 10%, 20%, 30%, 40%, 50%, 60%, 70%, 80%, or 90% less than the number of total dermatologic toxicity incidents in subjects administered an EGFR antagonist.

In other embodiments, the rate of total dermatologic toxicity incidents in subjects administered the antibody is less than 80%, 70%, 60%, 50%, 40%, 30%, 20%, 10%, 5%, 2%, or 1%.

Another aspect of the invention provides for a multispecific antibody that specifically binds to EGFR and at least one other HER receptor (HER2, HER3, and/or HER4) where the antibody induces fewer grade 3 or higher toxicity incidents in subjects administered the antibody as compared to grade 3 or higher toxicity incidents in subjects administered the EGFR antagonist. In particular embodiments, the number of grade 3 or higher toxicity incidents in subjects administered the antibody is at least 10%, 20%, 30%, 40%, 50%, 60%, 70%, 80%, or 90% less than the number of grade 3 or higher toxicity incidents in subjects administered an EGFR antagonist.

In other embodiments, the rate of grade 3 or higher toxicity incidents in subjects administered the multispecific antibody is less than 70%, 60%, 50%, 40%, 30%, 20%, 15%, 12%, 11%, 10%, 9%, 8%, 7%, 6%, 5%, 4%, 3%, 2%, or 1%.

In particular embodiments, the multispecific antibody induces fewer grade 3 or higher dermatologic toxicity incidents in subjects administered the bispecific antibody as compared to grade 3 or higher dermatologic toxicity incidents in subjects administered an EGFR antagonist. In particular embodiments, the number of grade 3 or higher dermatologic toxicity incidents in subjects administered the multispecific antibody is at least 10%, 20%, 30%, 40%, 50%, 60%, 70%, 80%, or 90% less than the number of grade 3 or higher dermatologic toxicity incidents in subjects administered an EGFR antagonist.

In other embodiments, the rate of grade 3 or higher dermatologic toxicity incidents in subjects administered the multispecific antibody is less than 70%, 60%, 50%, 40%, 30%, 20%, 15%, 12%, 11%, 10%, 9%, 8%, 7%, 6%, 5%, 4%, 3%, 2%, or 1%.

In other embodiments, the antibody induces fewer incidences of altered organ function in an in vivo model compared to an EGFR antagonist. In other embodiments, the antibody induces fewer, or less severe, gastrointestinal toxicities in an in vivo model compared to an EGFR antagonist.

In some embodiment, the EGFR antagonist is an anti-EGFR antibody. In one embodiment, the EGFR antagonist is cetuximab. In another embodiment, the EGFR antagonist is panitumumab. In another embodiments, the EGFR antagonist is a small molecule. In one embodiment, the EGFR antagonist is erlotinib. In one embodiment, the in vivo model is a monkey, such as a cynomolgus monkey. In another embodiment, the in vivo model is a human.

Antibody and Antibody Variants

In some embodiments, the invention provides a multispecific antibody comprising an antigen-binding domain that specifically binds to EGFR and HER3. In some embodiments, the antigen-binding domain does not specifically bind to other targets, including other HER receptors.

In one embodiment, the multispecific antibody comprises an antigen-binding domain that specifically binds to EGFR and HER3 where the antibody comprises a $V_H$ (heavy chain variable domain) comprising the amino acid sequence of SEQ ID NO: 25. In one embodiment, the multispecific antibody comprises an antigen-binding domain that specifically binds to EGFR and HER3 where the antibody comprises a $V_L$ (light chain variable domain) comprising the amino acid sequence of SEQ ID NO: 40. In one embodiment, the multispecific antibody comprises an antigen-binding domain that specifically binds to EGFR and HER3 where the antibody comprises a $V_H$ comprising the amino acid sequence of SEQ ID NO: 25 and a $V_L$ comprising the amino acid sequence of SEQ ID NO: 40.

In one embodiment, the multispecific antibody comprises an antigen-binding domain that specifically binds to EGFR and HER3 where the antibody comprises a $V_H$ comprising one, two, and/or three of the HVRs of the amino acid sequence of SEQ ID NO: 25. In one embodiment, the multispecific antibody comprises an antigen-binding domain that specifically binds to EGFR and HER3 where the antibody comprises a $V_L$ comprising one, two, and/or three of the HVRs of the amino acid sequence of SEQ ID NO: 40. In one embodiment, the multispecific antibody comprises an antigen-binding domain that specifically binds to EGFR and HER3 where the antibody comprises a $V_H$ comprising one, two, and/or three of the HVRs of the amino acid sequence of SEQ ID NO: 25 and a $V_L$ comprising one, two, and/or three of the HVRs of the amino acid sequence of SEQ ID NO: 40. In one embodiment, the multispecific antibody comprises an antigen-binding domain that specifically binds to EGFR and HER3 where the antibody comprises a $V_H$ comprising all three HVRs of the amino acid sequence of SEQ ID NO: 25 and a $V_L$ comprising all three of the HVRs of the amino acid sequence of SEQ ID NO: 40. In some embodiments, the HVRs are extended HVRs.

In one embodiment, the multispecific antibody comprises an antigen-binding domain that specifically binds to EGFR and HER3 where the antibody comprises a $V_H$ comprising the amino acid sequence of SEQ ID NO: 64. In one embodiment, the multispecific antibody comprises an antigen-binding domain that specifically binds to EGFR and HER3 where the antibody comprises a $V_L$ comprising the amino acid sequence of SEQ ID NO: 26. In one embodiment, the multispecific antibody comprises an antigen-binding domain that specifically binds to EGFR and HER3 where the antibody comprises a $V_H$ comprising the amino acid sequence of SEQ ID NO: 64 and a $V_L$ comprising the amino acid sequence of SEQ ID NO: 26.

In one embodiment, the multispecific antibody comprises an antigen-binding domain that specifically binds to EGFR and HER3 where the antibody comprises a $V_H$ comprising one, two, and/or three of the HVRs of the amino acid sequence of SEQ ID NO: 64. In one embodiment, the multispecific antibody comprises an antigen-binding domain that specifically binds to EGFR and HER3 where the antibody comprises a $V_L$ comprising one, two, and/or three of the HVRs of the amino acid sequence of SEQ ID NO: 26. In one embodiment, the multispecific antibody comprises an antigen-binding domain that specifically binds to EGFR and HER3 where the antibody comprises a $V_H$ comprising one, two, and/or three of the HVRs of the amino acid sequence of SEQ ID NO: 64 and a $V_L$ comprising one, two, and/or three of the HVRs of the amino acid sequence of SEQ ID NO: 26. In one embodiment, the multispecific antibody comprises an antigen-binding domain that specifically binds to EGFR and HER3 where the antibody comprises a $V_H$ comprising all three HVRs of the amino acid sequence of SEQ ID NO: 64 and a $V_L$ comprising all three of the HVRs of the amino acid sequence of SEQ ID NO: 26. In some embodiments, the HVRs are extended HVRs.

In one embodiment, the multispecific antibody comprises an antigen-binding domain that specifically binds to EGFR and HER3 where the antibody comprises a $V_H$ comprising the amino acid sequence of SEQ ID NO: 28. In one embodiment, the multispecific antibody comprises an antigen-binding domain that specifically binds to EGFR and HER3 where the antibody comprises a V$_L$ comprising the amino acid sequence of SEQ ID NO: 27. In one embodiment, the multispecific antibody comprises an antigen-binding domain that specifically binds to EGFR and HER3 where the antibody comprises a V$_H$ comprising the amino acid sequence of SEQ ID NO: 28 and a V$_L$ comprising the amino acid sequence of SEQ ID NO: 27.

In one embodiment, the multispecific antibody comprises an antigen-binding domain that specifically binds to EGFR and HER3 where the antibody comprises a V$_H$ comprising one, two, and/or three of the HVRs of the amino acid sequence of SEQ ID NO: 28. In one embodiment, the multispecific antibody comprises an antigen-binding domain that specifically binds to EGFR and HER3 where the antibody comprises a V$_L$ comprising one, two, and/or three of the HVRs of the amino acid sequence of SEQ ID NO: 27. In one embodiment, the multispecific antibody comprises an antigen-binding domain that specifically binds to EGFR and HER3 where the antibody comprises a V$_H$ comprising one, two, and/or three of the HVRs of the amino acid sequence of SEQ ID NO: 28 and a V$_L$ comprising one, two, and/or three of the HVRs of the amino acid sequence of SEQ ID NO: 27. In one embodiment, the multispecific antibody comprises an antigen-binding domain that specifically binds to EGFR and HER3 where the antibody comprises a V$_H$ comprising all three HVRs of the amino acid sequence of SEQ ID NO: 28 and a V$_L$ comprising all three of the HVRs of the amino acid sequence of SEQ ID NO: 27. In some embodiments, the HVRs are extended HVRs. In one specific embodiment, HVR-H1 comprises the amino acid sequence LSGDWIH (SEQ ID NO: 48), HVR-H2 comprises the amino acid sequence LGEISAAGGYTD (SEQ ID NO: 50), HVR-H3 comprises the amino acid sequence ARESRVSFEAAMDY (SEQ ID NO: 53), HVR-L1 comprises the amino acid sequence DLATDVA (SEQ ID NO: 54), HVR-L2 comprises the amino acid sequence SASF (SEQ ID NO: 56), and HVR-L3 comprises the amino acid sequence SEPEPYT (SEQ ID NO: 57).

In one embodiment, the multispecific antibody comprises an antigen-binding domain that specifically binds to EGFR and HER3 where the antibody comprises a V$_L$ comprising the amino acid sequence of SEQ ID NO: 29. In one embodiment, the multispecific antibody comprises an antigen-binding domain that specifically binds to EGFR and HER3 where the antibody comprises a V$_H$ comprising the amino acid sequence of SEQ ID NO: 28 and a V$_L$ comprising the amino acid sequence of SEQ ID NO: 29.

In one embodiment, the multispecific antibody comprises an antigen-binding domain that specifically binds to EGFR and HER3 where the antibody comprises a V$_L$ comprising one, two, and/or three of the HVRs of the amino acid sequence of SEQ ID NO: 29. In one embodiment, the multispecific antibody comprises an antigen-binding domain that specifically binds to EGFR and HER3 where the antibody comprises a V$_H$ comprising one, two, and/or three of the HVRs of the amino acid sequence of SEQ ID NO: 28 and a V$_L$ comprising one, two, and/or three of the HVRs of the amino acid sequence of SEQ ID NO: 29. In one embodiment, the multispecific antibody comprises an antigen-binding domain that specifically binds to EGFR and HER3 where the antibody comprises a V$_H$ comprising all three HVRs of the amino acid sequence of SEQ ID NO: 28 and a V$_L$ comprising all three of the HVRs of the amino acid sequence of SEQ ID NO: 29. In some embodiments, the HVRs are extended HVRs. In one specific embodiment, HVR-H1 comprises the amino acid sequence LSGDWIH (SEQ ID NO: 48), HVR-H2 comprises the amino acid sequence LGEISAAGGYTD (SEQ ID NO: 50), HVR-H3 comprises the amino acid sequence ARESRVSFEAAMDY (SEQ ID NO: 53), HVR-L1 comprises the amino acid sequence NIATDVA (SEQ ID NO: 55), HVR-L2 comprises the amino acid sequence SASF (SEQ ID NO: 56), and HVR-L3 comprises the amino acid sequence SEPEPYT (SEQ ID NO: 57).

In one embodiment, the multispecific antibody comprises an antigen-binding domain that specifically binds to EGFR and HER3 where the antibody comprises a V$_H$ comprising the amino acid sequence of SEQ ID NO: 30. In one embodiment, the multispecific antibody comprises an antigen-binding domain that specifically binds to EGFR and HER3 where the antibody comprises a V$_H$ comprising the amino acid sequence of SEQ ID NO: 30 and a V$_L$ comprising the amino acid sequence of SEQ ID NO: 29.

In one embodiment, the multispecific antibody comprises an antigen-binding domain that specifically binds to EGFR and HER3 where the antibody comprises a V$_H$ comprising one, two, and/or three of the HVRs of the amino acid sequence of SEQ ID NO: 30. In one embodiment, the multispecific antibody comprises an antigen-binding domain that specifically binds to EGFR and HER3 where the antibody comprises a V$_H$ comprising one, two, and/or three of the HVRs of the amino acid sequence of SEQ ID NO: 30 and a V$_L$ comprising one, two, and/or three of the HVRs of the amino acid sequence of SEQ ID NO: 29. In one embodiment, the multispecific antibody comprises an antigen-binding domain that specifically binds to EGFR and HER3 where the antibody comprises a V$_H$ comprising all three HVRs of the amino acid sequence of SEQ ID NO: 30 and a V$_L$ comprising all three of the HVRs of the amino acid sequence of SEQ ID NO: 29. In some embodiments, the HVRs are extended HVRs. In one specific embodiment, HVR-H1 comprises the amino acid sequence LSGDWIH (SEQ ID NO: 48), HVR-H2 comprises the amino acid sequence VGEISAAGGYTD (SEQ ID NO: 51), HVR-H3 comprises the amino acid sequence ARESRVSFEAAMDY (SEQ ID NO: 53), HVR-L1 comprises the amino acid sequence NIATDVA (SEQ ID NO: 55), HVR-L2 comprises the amino acid sequence SASF (SEQ ID NO: 56), and HVR-L3 comprises the amino acid sequence SEPEPYT (SEQ ID NO: 57).

In one embodiment, the multispecific antibody comprises an antigen-binding domain that specifically binds to EGFR and HER3 where the antibody comprises a V$_L$ comprising the amino acid sequence of SEQ ID NOs: 40, 41, 42, 43, 44, 45, or 46. In one embodiment, the multispecific antibody comprises an antigen-binding domain that specifically binds to EGFR and HER3 where the antibody comprises a V$_H$ comprising the amino acid sequence of SEQ ID NO: 25 and a V$_L$ comprising the amino acid sequence of SEQ ID NOs: 40, 41, 42, 43, 44, 45, or 46.

In one embodiment, the multispecific antibody comprises an antigen-binding domain that specifically binds to EGFR and HER3 where the antibody comprises a V$_L$ comprising one, two, and/or three of the HVRs of the amino acid sequence of SEQ ID NOs: 40, 41, 42, 43, 44, 45, or 46. In one embodiment, the multispecific antibody comprises an antigen-binding domain that specifically binds to EGFR and HER3 where the antibody comprises a V$_H$ comprising one, two, and/or three of the HVRs of the amino acid sequence of SEQ ID NO: 25 and a V$_L$ comprising one, two, and/or three of the HVRs of the amino acid sequence of SEQ ID NOs: 40, 41, 42, 43, 44, 45, or 46. In one embodiment, the multispecific antibody comprises an antigen-binding domain that specifically binds to EGFR and HER3 where the antibody comprises a V$_H$ comprising all three HVRs of the amino acid sequence of SEQ ID NO: 25 and a V$_L$ comprising all three of the HVRs of the amino acid sequence of SEQ ID NOs: 40, 41, 42, 43, 44, 45, or 46. In some embodiments, the HVRs are extended HVRs.

In one embodiment, the multispecific antibody comprises an antigen-binding domain that specifically binds to EGFR and HER2 where the antibody comprises a light chain variable domain comprising the amino acid sequence of SEQ ID NOs: 36, 37, or 38. In one embodiment, the multispecific antibody comprises an antigen-binding domain that specifically binds to EGFR and HER2 where the antibody comprises a heavy chain variable domain comprising the amino acid sequence of SEQ ID NO: 25 and a light chain variable domain comprising the amino acid sequence of SEQ ID NOs: 36, 37, or 38.

In one embodiment, the multispecific antibody comprises an antigen-binding domain that specifically binds to EGFR and HER2 where the antibody comprises a $V_H$ comprising one, two, and/or three of the HVRs of the amino acid sequence of SEQ ID NO: 25. In one embodiment, the multispecific antibody comprises an antigen-binding domain that specifically binds to EGFR and HER2 where the antibody comprises a $V_L$ comprising one, two, and/or three of the HVRs of the amino acid sequence of SEQ ID NOs: 36, 37, or 38. In one embodiment, the multispecific antibody comprises an antigen-binding domain that specifically binds to EGFR and HER2 where the antibody comprises a $V_H$ comprising one, two, and/or three of the HVRs of the amino acid sequence of SEQ ID NO: 25 and a $V_L$ comprising one, two, and/or three of the HVRs of the amino acid sequence of SEQ ID NOs: 36, 37, or 38. In one embodiment, the multispecific antibody comprises an antigen-binding domain that specifically binds to EGFR and HER2 where the antibody comprises a $V_H$ comprising all three HVRs of the amino acid sequence of SEQ ID NO: 25 and a $V_L$ comprising all three of the HVRs of the amino acid sequence of SEQ ID NOs: 36, 37, or 38. In some embodiments, the HVRs are extended HVRs.

In one embodiment, the multispecific antibody comprises an antigen-binding domain that specifically binds to EGFR and HER4 where the antibody comprises a $V_H$ comprising the amino acid sequence of SEQ ID NO: 25. In one embodiment, the multispecific antibody comprises an antigen-binding domain that specifically binds to EGFR and HER4 where the antibody comprises a $V_L$ comprising the amino acid sequence of SEQ ID NO: 39. In one embodiment, the multispecific antibody comprises an antigen-binding domain that specifically binds to EGFR and HER4 where the antibody comprises a heavy chain variable domain comprising the amino acid sequence of SEQ ID NO: 25 and a light chain variable domain comprising the amino acid sequence of SEQ ID NO: 39.

In one embodiment, the multispecific antibody comprises an antigen-binding domain that specifically binds to EGFR and HER4 where the antibody comprises a $V_L$ comprising one, two, and/or three of the HVRs of the amino acid sequence of SEQ ID NO: 39. In one embodiment, the multispecific antibody comprises an antigen-binding domain that specifically binds to EGFR and HER4 where the antibody comprises a $V_H$ comprising one, two, and/or three of the HVRs of the amino acid sequence of SEQ ID NO: 25 and a $V_L$ comprising one, two, and/or three of the HVRs of the amino acid sequence of SEQ ID NO: 39. In one embodiment, the multispecific antibody comprises an antigen-binding domain that specifically binds to EGFR and HER4 where the antibody comprises a $V_H$ comprising all three HVRs of the amino acid sequence of SEQ ID NO: 25 and a $V_L$ comprising all three of the HVRs of the amino acid sequence of SEQ ID NO: 39. In some embodiments, the HVRs are extended HVRs.

In one embodiment, the invention provides for a monospecific antibody comprising an antigen-binding domain that specifically binds to EGFR where the antibody comprises a $V_H$ comprising the amino acid sequence of SEQ ID NO: 25. In one embodiment, the monospecific antibody comprises an antigen-binding domain that specifically binds to EGFR where the antibody comprises a $V_L$ comprising the amino acid sequence of SEQ ID NO: 58 or SEQ ID NO: 24. In one embodiment, monospecific antibody comprises an antigen-binding domain that specifically binds to EGFR where the antibody comprises a $V_H$ comprising the amino acid sequence of SEQ ID NO: 25 and a $V_L$ comprising the amino acid sequence of SEQ ID NO: 58 or SEQ ID NO: 24.

In one embodiment, the invention provides for a monospecific antibody comprising an antigen-binding domain that specifically binds to EGFR where the antibody comprises a $V_H$ comprising one, two, and/or three of the HVRs of the amino acid sequence of SEQ ID NO: 25. In one embodiment, the monospecific antibody comprises an antigen-binding domain that specifically binds to EGFR where the antibody comprises a $V_L$ comprising one, two, and/or three of the HVRs of the amino acid sequence of SEQ ID NO: 24. In one embodiment, the monospecific antibody comprises an antigen-binding domain that specifically binds to EGFR where the antibody comprises a $V_H$ comprising one, two, and/or three of the HVRs of the amino acid sequence of SEQ ID NO: 25 and a $V_L$ comprising one, two, and/or three of the HVRs of the amino acid sequence of SEQ ID NO: 24. In one embodiment, the monospecific antibody comprises an antigen-binding domain that specifically binds to EGFR where the antibody comprises a $V_H$ comprising all three HVRs of the amino acid sequence of SEQ ID NO: 25 and a $V_L$ comprising all three of the HVRs of the amino acid sequence of SEQ ID NO: 24. In some embodiments, the HVRs are extended HVRs. In one specific embodiment, HVR-H1 comprises the amino acid sequence FTGNWIH (SEQ ID NO: 47), HVR-H2 comprises the amino acid sequence VGEISPSGGYTD (SEQ ID NO: 49), HVR-H3 comprises the amino acid sequence ARESRVSYEAAMDY (SEQ ID NO: 52), HVR-L1 comprises the amino acid sequence DVSTAVA (SEQ ID NO: 78), HVR-L2 comprises the amino acid sequence SASF (SEQ ID NO: 56), and HVR-L3 comprises the amino acid sequence SYPTPYT (SEQ ID NO: 79).

In one embodiment, the invention provides for a monospecific antibody comprising an antigen-binding domain that specifically binds to HER3 where the antibody comprises a $V_H$ comprising the amino acid sequence of SEQ ID NO: 29. In one embodiment, the monospecific antibody comprises an antigen-binding domain that specifically binds to HER3 where the antibody comprises a $V_L$ comprising the amino acid sequence of SEQ ID NOs: 33, 34, or 35. In one embodiment, monospecific antibody comprises an antigen-binding domain that specifically binds to HER3 where the antibody comprises a $V_H$ comprising the amino acid sequence of SEQ ID NO: 29 and a $V_L$ comprising the amino acid sequence of SEQ ID NOs: 33, 34, or 35.

In one embodiment, the invention provides for a monospecific antibody comprising an antigen-binding domain that specifically binds to HER3 where the antibody comprises a $V_H$ comprising one, two, and/or three of the HVRs of the amino acid sequence of SEQ ID NO: 29. In one embodiment, the monospecific antibody comprises an antigen-binding domain that specifically binds to HER3 where the antibody comprises a $V_L$ comprising one, two, and/or three of the HVRs of the amino acid sequence of SEQ ID NOs: 33, 34, or 35. In one embodiment, the monospecific antibody comprises an antigen-binding domain that specifically binds to HER3 where the antibody comprises a $V_H$ comprising one, two, and/or three of the HVRs of the amino acid sequence of SEQ ID NO: 29 and a $V_L$ comprising one, two, and/or three of the HVRs of the amino acid sequence of SEQ ID NOs: 33, 34, or 35. In one embodiment, the monospecific antibody comprises an antigen-binding domain that specifically binds to HER3 where the antibody comprises a $V_H$ comprising all three HVRs of the amino acid sequence of SEQ ID NO: 29 and a $V_L$ comprising all three of the HVRs of the amino acid sequence of SEQ ID NOs: 33, 34, or 35. In some embodiments, the HVRs are extended HVRs. In one specific embodiment, HVR-H1 comprises the amino acid sequence FTGDWIH (SEQ ID NO: 62), HVR-H2 comprises the amino acid sequence VGEISPAGAYTD (SEQ ID NO: 60), HVR-H3 comprises the amino acid sequence AREAKVSFEAAMDY (SEQ ID NO: 61), HVR-L1 comprises the amino acid sequence NIATDVA (SEQ ID NO: 55), HVR-L2 comprises the amino acid sequence SASF (SEQ ID NO: 56), and HVR-L3 comprises the amino acid sequence SEPEPYT (SEQ ID NO: 57).

In one embodiment, the invention provides for a monospecific antibody comprising an antigen-binding domain that specifically binds to HER3 where the antibody comprises a $V_H$ comprising the amino acid sequence of SEQ ID NO: 32. In one embodiment, the monospecific antibody comprises an antigen-binding domain that specifically binds to HER3 where the antibody comprises a $V_L$ comprising the amino acid sequence of SEQ ID NO: 31. In one embodiment, monospecific antibody comprises an antigen-binding domain that specifically binds to HER3 where the antibody comprises a $V_H$ comprising the amino acid sequence of SEQ ID NO: 32 and a $V_L$ comprising the amino acid sequence of SEQ ID NO: 31.

In one embodiment, the invention provides for a monospecific antibody comprising an antigen-binding domain that specifically binds to HER3 where the antibody comprises a $V_H$ comprising one, two, and/or three of the HVRs of the amino acid sequence of SEQ ID NO: 32. In one embodiment, the monospecific antibody comprises an antigen-binding domain that specifically binds to HER3 where the antibody comprises a $V_L$ comprising one, two, and/or three of the HVRs of the amino acid sequence of SEQ ID NO: 31. In one embodiment, the monospecific antibody comprises an antigen-binding domain that specifically binds to HER3 where the antibody comprises a $V_H$ comprising one, two, and/or three of the HVRs of the amino acid sequence of SEQ ID NO: 32 and a $V_L$ comprising one, two, and/or three of the HVRs of the amino acid sequence of SEQ ID NO: 31. In one embodiment, the monospecific antibody comprises an antigen-binding domain that specifically binds to HER3 where the antibody comprises a $V_H$ comprising all three HVRs of the amino acid sequence of SEQ ID NO: 32 and a $V_L$ comprising all three of the HVRs of the amino acid sequence of SEQ ID NO: 31. In some embodiments, the HVRs are extended HVRs. In one specific embodiment, HVR-H1 comprises the amino acid sequence FSGDWIH (SEQ ID NO: 59), HVR-H2 comprises the amino acid sequence VGEISPAGAYTD (SEQ ID NO: 60), HVR-H3 comprises the amino acid sequence AREAKVSFEAAMDY (SEQ ID NO: 61), HVR-L1 comprises the amino acid sequence DLATDVA (SEQ ID NO: 54), HVR-L2 comprises the amino acid sequence SASF (SEQ ID NO: 56), and HVR-L3 comprises the amino acid sequence SEPEPYT (SEQ ID NO: 57).

In one embodiment, the multispecific antibody comprises an antigen-binding domain that specifically binds to EGFR and HER3 where the antibody comprises a heavy chain comprising the amino acid sequences of SEQ ID NOs: 2, 12, or 14. In one embodiment, the multispecific antibody comprises an antigen-binding domain that specifically binds to EGFR and HER3 where the antibody comprises a light chain comprising the amino acid sequence of SEQ ID NOs: 4, 5, 6, 7, 8, 9, 10, 11, or 13. In one embodiment, the multispecific antibody comprises an antigen-binding domain that specifically binds to EGFR and HER3 where the antibody comprises a heavy chain comprising the amino acid sequence of SEQ ID NO: 2 and a light chain comprising the amino acid sequence of SEQ ID NO: 4. In one embodiment, the multispecific antibody comprises an antigen-binding domain that specifically binds to EGFR and HER3 where the antibody comprises a heavy chain comprising the amino acid sequence of SEQ ID NO: 12 and a light chain comprising the amino acid sequence of SEQ ID NO: 11. In one embodiment, the multispecific antibody comprises an antigen-binding domain that specifically binds to EGFR and HER3 where the antibody comprises a heavy chain comprising the amino acid sequence of SEQ ID NO: 12 and a light chain comprising the amino acid sequence of SEQ ID NO: 13. In one embodiment, the multispecific antibody comprises an antigen-binding domain that specifically binds to EGFR and HER3 where the antibody comprises a heavy chain comprising the amino acid sequence of SEQ ID NO: 14 and a light chain comprising the amino acid sequence of SEQ ID NO: 13.

In some embodiments, the invention provides a multispecific antibody comprising an antigen-binding domain that specifically binds to EGFR and HER2. In some embodiments, the antigen-binding domain does not specifically bind to other targets, including other HER receptors. In one embodiment, the multispecific antibody comprises an antigen-binding domain that specifically binds to EGFR and HER2 where the antibody comprises a heavy chain comprising the amino acid sequence of SEQ ID NO: 2. In one embodiment, the multispecific antibody comprises an antigen-binding domain that specifically binds to EGFR and HER2 where the antibody comprises a light chain comprising the amino acid sequence of SEQ ID NOs: 21, 22, or 23.

In some embodiments, the invention provides a multispecific antibody comprising an antigen-binding domain that specifically binds to EGFR and HER4. In some embodiments, the antigen-binding domain does not specifically bind to other targets, including other HER receptors. In one embodiment, the multispecific antibody comprises an antigen-binding domain that specifically binds to EGFR and HER4 where the antibody comprises a heavy chain comprising the amino acid sequence of SEQ ID NO: 2. In one embodiment, the multispecific antibody comprises an antigen-binding domain that specifically binds to EGFR and HER4 where the antibody comprises a light chain comprising the amino acid sequence of SEQ ID NO: 18.

In one embodiment, the invention provides a monospecific antibody that specifically binds to EGFR. In some embodiments, the antigen-binding domain does not specifically bind to other targets, including other HER receptors. In one embodiment, the monospecific antibody comprises an antigen-binding domain that specifically binds to EGFR where the antibody comprises a heavy chain comprising the amino acid sequence of SEQ ID NO: 2. In one embodiment, the monospecific antibody comprises an antigen-binding domain that specifically binds to EGFR where the antibody comprises a light chain comprising the amino acid sequence of SEQ ID NOs: 1 or 3. In one embodiment, the monospecific antibody comprises an antigen-binding domain that specifically binds to EGFR where the antibody comprises a heavy chain comprising the amino acid sequence of SEQ ID NO: 2 and a light chain comprising the amino acid sequence of SEQ ID NO: 1.

In one embodiment, the monospecific antibody comprises an antigen-binding domain that specifically binds to EGFR where the antibody comprises a heavy chain comprising the amino acid sequence of SEQ ID NO: 2 and a light chain comprising the amino acid sequence of SEQ ID NO: 3.

In one embodiment, the invention provides a monospecific antibody that specifically binds to HER3. In some embodiments, the antigen-binding domain does not specifically bind to other targets, including other HER receptors. In one embodiment, the monospecific antibody comprises an antigen-binding domain that specifically binds to HER3 where the antibody comprises a heavy chain comprising the amino acid sequence of SEQ ID NOs: 16, 17, 19, or 20. In one embodiment, the monospecific antibody comprises an antigen-binding domain that specifically binds to HER3 where the antibody comprises a light chain comprising the amino acid sequence of SEQ ID NOs: 13 or 15. In one embodiment, the monospecific antibody comprises an antigen-binding domain that specifically binds to HER3 where the antibody comprises a heavy chain comprising the amino acid sequence of SEQ ID NOs: 16, 17, 19, or 20 and a light chain comprising the amino acid sequence of SEQ ID NOs: 13 or 15.

In one embodiment, the monospecific antibody comprises an antigen-binding domain that specifically binds to HER3 where the antibody comprises a heavy chain comprising the amino acid sequence of SEQ ID NO: 16 and a light chain comprising the amino acid sequence of SEQ ID NO: 15. In one embodiment, the monospecific antibody comprises an antigen-binding domain that specifically binds to HER3 where the antibody comprises a heavy chain comprising the amino acid sequence of SEQ ID NO: 17 and a light chain comprising the amino acid sequence of SEQ ID NO: 13. In one embodiment, the monospecific antibody comprises an antigen-binding domain that specifically binds to HER3 where the antibody comprises a heavy chain comprising the amino acid sequence of SEQ ID NO: 19 and a light chain comprising the amino acid sequence of SEQ ID NO: 13. In one embodiment, the monospecific antibody comprises an antigen-binding domain that specifically binds to HER3 where the antibody comprises a heavy chain comprising the amino acid sequence of SEQ ID NO: 20 and a light chain comprising the amino acid sequence of SEQ ID NO: 13.

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

In some embodiments, an amino acid sequence having at least 80%, 85%, 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to the original target or targets of the reference sequence. In some embodiments, an amino acid sequence having at least 80%, 85%, 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to the original target or target of the reference sequence and does not specifically bind to any other target, including other HER receptors. In some embodiments, a total of 1 to 10 amino acids have been substituted, inserted, or deleted in the amino acid sequence of a reference sequence. In some embodiments, the substitutions, insertions, or deletions occur in regions outside the HVRs (i.e., in the FRs).

In one embodiment, the multispecific antibody comprises an antigen-binding domain that specifically binds to EGFR and HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25.

In one embodiment, the multispecific antibody comprises an antigen-binding domain that specifically binds to EGFR and HER3 where the antibody comprises a $V_L$ having at least 80%, 85%, 90%, 91%, 92%, 93%, 94%, 95%, 96%, 97%, 98%, or 99% sequence identity to the amino acid sequence of SEQ ID NO: 40 In one embodiment, the multispecific antibody comprises an antigen-binding domain that specifically binds to EGFR and HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25 and a $V_L$ having at least 80%, 85%, 90%, 91%, 92%, 93%, 94%, 95%, 96%, 97%, 98%, or 99% sequence identity to the amino acid sequence of SEQ ID NO: 40.

In one embodiment, the multispecific antibody comprises an antigen-binding domain that specifically binds to EGFR and HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 64. In one embodiment, the multispecific antibody comprises an antigen-binding domain that specifically binds to EGFR and HER3 where the antibody comprises a $V_L$ having at least 80%, 85%, 90%, 91%, 92%, 93%, 94%, 95%, 96%, 97%, 98%, or 99% sequence identity to the amino acid sequence of SEQ ID NO: 26. In one embodiment, the multispecific antibody comprises an antigen-binding domain that specifically binds to EGFR and HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 64 and a $V_L$ having at least 80%, 85%, 90%, 91%, 92%, 93%, 94%, 95%, 96%, 97%, 98%, or 99% sequence identity to the amino acid sequence of SEQ ID NO: 26.

In one embodiment, the multispecific antibody comprises an antigen-binding domain that specifically binds to EGFR and HER3 where the antibody comprises a $V_L$ having the amino acid sequence of at least 80%, 85%, 90%, 91%, 92%, 93%, 94%, 95%, 96%, 97%, 98%, or 99% sequence identity to SEQ ID NO: 29. In one embodiment, the multispecific antibody comprises an antigen-binding domain that specifically binds to EGFR and HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 28 and a $V_L$ having at least 80%, 85%, 90%, 91%, 92%, 93%, 94%, 95%, 96%, 97%, 98%, or 99% sequence identity to the amino acid sequence of SEQ ID NO: 29.

In one embodiment, the multispecific antibody comprises an antigen-binding domain that specifically binds to EGFR and HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 30. In one embodiment, the multispecific antibody comprises an antigen-binding domain that specifically binds to EGFR and HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 30 and a $V_L$ having at least 80%, 85%, 90%, 91%, 92%, 93%, 94%, 95%, 96%, 97%, 98%, or 99% sequence identity to the amino acid sequence of SEQ ID NO: 29.

In one embodiment, the multispecific antibody comprises an antigen-binding domain that specifically binds to EGFR and HER3 where the antibody comprises a $V_L$ having at least 80%, 85%, 90%, 91%, 92%, 93%, 94%, 95%, 96%, 97%, 98%, or 99% sequence identity to any one of the amino acid sequences of SEQ ID NOs: 40, 41, 42, 43, 44, 45, or 46. In one embodiment, the multispecific antibody comprises an antigen-binding domain that specifically binds to EGFR and HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25 and a $V_L$ having at least 80%, 85%, 90%, 91%, 92%, 93%, 94%, 95%, 96%, 97%, 98%, or 99% sequence identity to the amino acid sequence of SEQ ID NOs: 40, 41, 42, 43, 44, 45, or 46.

In one embodiment, the multispecific antibody comprises an antigen-binding domain that specifically binds to EGFR and HER2 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25. In one embodiment, the multispecific antibody comprises an antigen-binding domain that specifically binds to EGFR and HER2 where the antibody comprises a $V_L$ having at least 80%, 85%, 90%, 91%, 92%, 93%, 94%, 95%, 96%, 97%, 98%, or 99% sequence identity to the amino acid sequence of SEQ ID NO: 36. In one embodiment, the multispecific antibody comprises an antigen-binding domain that specifically binds to EGFR and HER2 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25 and a $V_L$ having at least 80%, 85%, 90%, 91%, 92%, 93%, 94%, 95%, 96%, 97%, 98%, or 99% sequence identity to the amino acid sequence of SEQ ID NO: 36. In one embodiment, the multispecific antibody comprises an antigen-binding domain that specifically binds to EGFR and HER2 where the antibody comprises a $V_L$ having at least 80%, 85%, 90%, 91%, 92%, 93%, 94%, 95%, 96%, 97%, 98%, or 99% sequence identity to the amino acid sequence of SEQ ID NO: 37. In one embodiment, the multispecific antibody comprises an antigen-binding domain that specifically binds to EGFR and HER2 where the antibody comprises a $V_H$ domain having at least 80%, 85%, 90%, 91%, 92%, 93%, 94%, 95%, 96%, 97%, 98%, or 99% sequence identity to the amino acid sequence of SEQ ID NO: 25 and a $V_L$ having the amino acid sequence of SEQ ID NO: 37. In one embodiment, the multispecific antibody comprises an antigen-binding domain that specifically binds to EGFR and HER2 where the antibody comprises a $V_L$ having the amino acid sequence of SEQ ID NO: 38. In one embodiment, the multispecific antibody comprises an antigen-binding domain that specifically binds to EGFR and HER2 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25 and a $V_L$ having at least 80%, 85%, 90%, 91%, 92%, 93%, 94%, 95%, 96%, 97%, 98%, or 99% sequence identity to the amino acid sequence of SEQ ID NO: 38.

In one embodiment, the multispecific antibody comprises an antigen-binding domain that specifically binds to EGFR and HER4 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25. In one embodiment, the multispecific antibody comprises an antigen-binding domain that specifically binds to EGFR and HER4 where the antibody comprises a $V_L$ having at least 80%, 85%, 90%, 91%, 92%, 93%, 94%, 95%, 96%, 97%, 98%, or 99% sequence identity to the amino acid sequence of SEQ ID NO: 39. In one embodiment, the multispecific antibody comprises an antigen-binding domain that specifically binds to EGFR and HER4 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25 and a $V_L$ having at least 80%, 85%, 90%, 91%, 92%, 93%, 94%, 95%, 96%, 97%, 98%, or 99% sequence identity to the amino acid sequence of SEQ ID NO: 39.

In one embodiment, the invention provides for a monospecific antibody comprising an antigen-binding domain that specifically binds to EGFR where the antibody comprises a $V_H$ having at least 80%, 85%, 90%, 91%, 92%, 93%, 94%, 95%, 96%, 97%, 98%, or 99% sequence identity the amino acid sequence of SEQ ID NO: 25. In one embodiment, the monospecific antibody comprises an antigen-binding domain that specifically binds to EGFR where the antibody comprises a $V_L$ having at least 80%, 85%, 90%, 91%, 92%, 93%, 94%, 95%, 96%, 97%, 98%, or 99% sequence identity to the amino acid sequence of SEQ ID NO: 24. In one embodiment, the monospecific antibody comprises an antigen-binding domain that specifically binds to EGFR where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 25 and a $V_L$ having at least 80%, 85%, 90%, 91%, 92%, 93%, 94%, 95%, 96%, 97%, 98%, or 99% sequence identity to the amino acid sequence of SEQ ID NO: 24.

In one embodiment, the invention provides for a monospecific antibody comprising an antigen-binding domain that specifically binds to HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 32. In one embodiment, the monospecific antibody comprises an antigen-binding domain that specifically binds to HER3 where the antibody comprises a $V_L$ having at least 80%, 85%, 90%, 91%, 92%, 93%, 94%, 95%, 96%, 97%, 98%, or 99% sequence identity to the amino acid sequence of SEQ ID NO: 31. In one embodiment, the monospecific antibody comprises an antigen-binding domain that specifically binds to HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 32 and a $V_L$ having at least 80%, 85%, 90%, 91%, 92%, 93%, 94%, 95%, 96%, 97%, 98%, or 99% sequence identity to the amino acid sequence of SEQ ID NO: 31.

In one embodiment, the monospecific antibody comprises an antigen-binding domain that specifically binds to HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 33. In one embodiment, the monospecific antibody comprises an antigen-binding domain that specifically binds to HER3 where the antibody comprises a $V_L$ having at least 80%, 85%, 90%, 91%, 92%, 93%, 94%, 95%, 96%, 97%, 98%, or 99% sequence identity to the amino acid sequence of SEQ ID NO:

29. In one embodiment, the monospecific antibody comprises an antigen-binding domain that specifically binds to HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 33 and a $V_L$ having at least 80%, 85%, 90%, 91%, 92%, 93%, 94%, 95%, 96%, 97%, 98%, or 99% sequence identity to the amino acid sequence of SEQ ID NO: 29. In one embodiment, the monospecific antibody comprises an antigen-binding domain that specifically binds to HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 34. In one embodiment, the monospecific antibody comprises an antigen-binding domain that specifically binds to HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 34 and a $V_L$ having at least 80%, 85%, 90%, 91%, 92%, 93%, 94%, 95%, 96%, 97%, 98%, or 99% sequence identity to the amino acid sequence of SEQ ID NO: 29. In one embodiment, the monospecific antibody comprises an antigen-binding domain that specifically binds to HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 35. In one embodiment, the monospecific antibody comprises an antigen-binding domain that specifically binds to HER3 where the antibody comprises a $V_H$ having at least 80%, 85%, 90%, 91%, 92%, 93%, 94%, 95%, 96%, 97%, 98%, or 99% sequence identity to the amino acid sequence of SEQ ID NO: 35 and a $V_L$ having at least 80%, 85%, 90%, 91%, 92%, 93%, 94%, 95%, 96%, 97%, 98%, or 99% sequence identity to the amino acid sequence of SEQ ID NO: 29.

An exemplary alignment showing the Kabat numbering for the heavy chain variable domain and light chain variable domain of several anti-HER antibodies is shown in FIG. 33.

Another aspect of the invention provides for a multispecific antibody comprising an antigen-binding domain that specifically binds to EGFR and HER3 where the antibody comprises a $V_H$ comprising the amino acid sequence of SEQ ID NO: 25 where the $V_H$ of SEQ ID NO: 25 comprises an amino acid substitution at F29($V_H$), T30($V_H$), N32($V_H$), V48($V_H$), P52a($V_H$), S53($V_H$), T57($V_H$), S96($V_H$), or Y100($V_H$), numbered according to the Kabat numbering system. In one embodiment, the antibody comprises more than one of these substitutions. In one embodiment, the antibody comprises all of these substitutions. In one embodiment, the multispecific antibody comprises an antigen-binding domain that specifically binds to EGFR and HER3 where the antibody comprises a $V_H$ comprising the amino acid sequence of SEQ ID NO: 25 where the $V_H$ of SEQ ID NO: 25 comprises one or more amino acid substitutions selected from the group consisting of F29($V_H$)L; T30($V_H$)S; N32($V_H$)D, V48($V_H$)L, P52a($V_H$)A, S53($V_H$)A, T57($V_H$)S, S96($V_H$)A, and Y100($V_H$)F, numbered according to the Kabat numbering system. In one embodiment, the multispecific antibody comprises an antigen-binding domain that specifically binds to EGFR and HER3 where the antibody comprises a $V_H$ comprising the amino acid sequence of SEQ ID NO: 25 where the $V_H$ of SEQ ID NO: 25 comprises the amino acid substitutions F29($V_H$)L, T30($V_H$)S, N32($V_H$)D, P52a($V_H$)A, and S53($V_H$)A, and Y100($V_H$)F, numbered according to the Kabat numbering system.

Another aspect of the invention provides for a multispecific antibody comprising an antigen-binding domain that specifically binds to EGFR and HER3 where the antibody comprises a $V_L$ comprising the amino acid sequence of SEQ ID NO: 58 where the $V_L$ of SEQ ID NO: 58 comprises an amino acid substitution at D28($V_L$), V29($V_L$), S30($V_L$), T31($V_L$), A32($V_L$), V33($V_L$), S50($V_L$), A51($V_L$), F53($V_L$), S91($V_L$), Y92($V_L$), T93($V_L$), T94($V_L$), or P96($V_L$), numbered according to the Kabat numbering system. In one embodiment, the antibody comprises more than one of these substitutions. In one embodiment, the antibody comprises all of these substitutions. In one embodiment, the antibody comprises amino acid insertions between amino acid 31 and amino acid 32.

In one embodiment, the multispecific antibody comprises an antigen-binding domain that specifically binds to EGFR and HER3 where the antibody comprises a $V_L$ comprising the amino acid sequence of SEQ ID NO: 58 where the $V_L$ of SEQ ID NO: 58 comprises one or more amino acid substitutions selected from the group consisting of D28($V_L$)N, V29($V_L$)I, V29($V_L$)L, S30($V_L$)A, A32($V_L$)D, Y92($V_L$)E, T93($V_L$)P, T94($V_L$)E, and P96($V_L$)Y, numbered according to the Kabat numbering system. In one embodiment, the multispecific antibody comprises an antigen-binding domain that specifically binds to EGFR and HER3 where the antibody comprises a $V_L$ comprising the amino acid sequence of SEQ ID NO: 58 where the $V_L$ of SEQ ID NO: 58 comprises the amino acid substitutions D28($V_L$)N, V29($V_L$)I, S30($V_L$)A, A32($V_L$)D, Y92($V_L$)E, T93($V_L$)P, T94($V_L$)E, and P96($V_L$)Y, numbered according to the Kabat numbering system.

In one embodiment, the multispecific antibody comprises an antigen-binding domain that specifically binds to EGFR and HER3 where the antibody comprises a $V_H$ comprising the amino acid sequence of SEQ ID NO: 25 and a $V_L$ comprising the amino acid sequence of SEQ ID NO: 58, where the $V_H$ of SEQ ID NO: 25 comprises an amino acid substitution at F29($V_H$), T30($V_H$), N32($V_H$), V48($V_H$), P52a($V_H$), S53($V_H$), T57($V_H$), S96($V_H$), or Y100($V_H$), and where the $V_L$ of SEQ ID NO: 58 comprises an amino acid substitution at D28($V_L$), V29($V_L$), S30($V_L$), T31($V_L$), A32($V_L$), V33($V_L$), S50($V_L$), A51($V_L$), F53($V_L$), S91($V_L$), Y92($V_L$), T93($V_L$), T94($V_L$), or P96($V_L$), numbered according to the Kabat numbering system. In one embodiment, the antibody comprises more than one of these substitutions. In one embodiment, the antibody comprises all of these substitutions.

In one embodiment, the multispecific antibody comprises an antigen-binding domain that specifically binds to EGFR and HER3 where the antibody comprises a $V_H$ comprising the amino acid sequence of SEQ ID NO: 25 and a $V_L$ comprising the amino acid sequence of SEQ ID NO: 58, where the $V_H$ of SEQ ID NO: 25 comprises one or more amino acid substitutions selected from the group consisting of F29($V_H$)L; T30($V_H$)S; N32($V_H$)D, V48($V_H$)L, P52a($V_H$)A, S53($V_H$)A, T57($V_H$)S, S96($V_H$)A, and Y100($V_H$)F, the $V_L$ of SEQ ID NO: 58 comprises one or more amino acid substitutions selected from the group consisting of D28($V_L$)N, V29($V_L$)I, V29($V_L$)L, S30($V_L$)A, A32($V_L$)D, Y92($V_L$)E, T93($V_L$)P, T94($V_L$)E, and P96($V_L$)Y, numbered according to the Kabat numbering system.

In one embodiment, the multispecific antibody comprises an antigen-binding domain that specifically binds to EGFR and HER3 where the antibody comprises a $V_H$ comprising the amino acid sequence of SEQ ID NO: 25 where the $V_H$ of SEQ ID NO: 25 comprises the amino acid substitutions F29($V_H$)L, T30($V_H$)S, N32($V_H$)D, P52a($V_H$)A, and S53($V_H$)A, and Y100($V_H$)F, and a $V_L$ comprising the amino acid sequence of SEQ ID NO: 58 where the $V_L$ of SEQ ID NO: 58 comprises the amino acid substitutions D28($V_L$)N, V29($V_L$)I, S30($V_L$)A, A32($V_L$)D, Y92($V_L$)E, T93($V_L$)P, T94($V_L$)E, and P96($V_L$)Y, numbered according to the Kabat numbering system.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. (1997) *TIBTECH* 15:26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed. See, for example, Petkova, S. B. et al., *Int'l. Immunol.* 18(12):1759-1769 (2006)).

Other antibody variants having one or more amino acid substitutions are provided. Sites of interest for substitutional mutagenesis include the hypervariable regions, but FR alterations are also contemplated. Conservative substitutions are shown in Table 1 under the heading of "preferred substitutions." More substantial changes, denominated "exemplary substitutions" are provided in Table 4, or as further described below in reference to amino acid classes. Amino acid substitutions may be introduced into an antibody of interest and the products screened, e.g., for a desired activity, such as improved antigen-binding, decreased immunogenicity, improved ADCC or CDC, etc.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu; Asn | Glu |
| Cys (C) | Ser; Ala | Ser |
| Gln (Q) | Asn;Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine, Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Modifications in the biological properties of an antibody may be accomplished by selecting substitutions that affect (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. An exemplary substitutional variant is an affinity matured antibody, which may be conveniently generated using phage display-based affinity maturation techniques. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle.

The phage-displayed variants are then screened for their biological activity (e.g. binding affinity). In order to identify candidate hypervariable region sites for modification, scanning mutagenesis (e.g., alanine scanning) can be performed to identify hypervariable region residues contributing significantly to antigen-binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and variants with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Immunoconjugates

The invention also provides immunoconjugates (interchangeably referred to as "antibody-drug conjugates," or "ADCs") comprising an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope, such as $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu (i.e., a radioconjugate).

Immunoconjugates have been used for the local delivery of cytotoxic agents, i.e., drugs that kill or inhibit the growth or proliferation of cells, in the treatment of cancer (Lambert, J. (2005) *Curr. Opinion in Pharmacology* 5:543-549; Wu et al (2005) *Nature Biotechnology* 23(9):1137-1146; Payne, G. (2003) i 3:207-212; Syrigos and Epenetos (1999) *Anticancer Research* 19:605-614; Niculescu-Duvaz and Springer (1997) *Adv. Drug Deliv. Rev.* 26:151-172; U.S. Pat. No. 4,975,278) Immunoconjugates allow for the targeted delivery of a drug moiety to a tumor, and intracellular accumulation therein, where systemic administration of unconjugated drugs may result in unacceptable levels of toxicity to normal cells as well as the tumor cells sought to be eliminated (Baldwin et al., *Lancet* (Mar. 15, 1986) pp. 603-05; Thorpe (1985) "Antibody Carriers Of Cytotoxic Agents In Cancer Therapy: A Review," in *Monoclonal Antibodies '84: Biological And Clinical Applications* (A. Pinchera et al., eds) pp. 475-506. Both polyclonal antibodies and monoclonal antibodies have been reported as useful in these strategies (Rowland et al., (1986) *Cancer Immunol. Immunother.* 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791), maytansinoids (EP 1391213; Liu et al., (1996) *Proc. Natl. Acad. Sci. USA* 93:8618-8623), and calicheamicin (Lode et al (1998) *Cancer Res.* 58:2928; Hinman et al (1993) *Cancer Res.* 53:3336-3342). The toxins may exert their cytotoxic effects by mechanisms including tubulin binding, DNA binding, or topoisomerase inhibition. Some cytotoxic drugs tend to be inactive or less active when conjugated to large antibodies or protein receptor ligands.

Trastuzumab-DM1 (or T-DM1) has been shown to be efficacious in trastuzumab-sensitive and trastuzumab-insensitive models of HER2-overexpressing cancer. (U.S. Pat. No. 7,097,840). ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111In or 90Y radioisotope bound by a thiourea linker-chelator (Wiseman et al (2000) *Eur. Jour. Nucl. Med.* 27(7):766-77; Wiseman et al (2002) *Blood* 99(12):4336-42; Witzig et al (2002) *J. Clin. Oncol.* 20(10): 2453-63; Witzig et al (2002) *J. Clin. Oncol.* 20(15):3262-69). Although ZEVALIN has activity against B-cell non-Hodgkin's Lymphoma (NHL), administration results in severe and prolonged cytopenias in most patients. MYLO-TARG™ (gemtuzumab ozogamicin, Wyeth Pharmaceuticals), an antibody-drug conjugate composed of a huCD33 antibody linked to calicheamicin, was approved in 2000 for the treatment of acute myeloid leukemia by injection (*Drugs of the Future* (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody-drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and other cancers. MLN-2704 (Millennium Pharm., BZL Biologics, Immunogen Inc.), an antibody-drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) *Nature Biotechnol.* 21(7):778-784) and are under therapeutic development.

In certain embodiments, an immunoconjugate comprises an antibody and a chemotherapeutic agent or other toxin. Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

Maytansine and Maytansinoids

In some embodiments, the immunoconjugate comprises an antibody (full length or fragments) conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses 3×105 HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Auristatins and Dolastatins

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schroder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. Nos. 5,635,483; 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 1 5:859-863. See also Doronina (2003) Nat Biotechnol 21(7): 778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, 1I, 2I, 3I, N-acetyl-1I, PSAG and I1 (Hinman et al., Cancer Research 53:3336-3342 (1993), Lode et al., Cancer Research 58:2925-2928 (1998) and the aforementioned U.S. patents to American Cyanamid). Another antitumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99}m$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds expressly contemplate, but are not limited to, ADC prepared with cross-linker reagents: BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-STAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC), an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)_p \quad\quad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC"), and N-Succinimidyl (4-iodo-acetyl)aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Recombinant Methods and Compositions

Antibodies may be produced using recombinant methods and compositions, e.g., as described in U.S. Pat. No. 4,816,567. In one embodiment, isolated nucleic acid encoding an anti-HER antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-HER antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-HER antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in E. coli.) After expression, the antibody may be isolated from the bacterial cell paste in a soluble fraction and can be further purified. In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., J. Gen Virol. 36:59 (1977)); baby hamster kidney cells (BHK); mouse sertoli cells (TM4 cells as described, e.g., in Mather, Biol. Reprod. 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383: 44-68 (1982); MRC 5 cells; and FS4 cells. Other useful mammalian host cell lines include Chinese hamster ovary (CHO) cells, including DHFR-CHO cells (Urlaub et al., Proc. Natl. Acad. Sci. USA 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Therapeutic Uses

The antibodies and antibody fragments described herein can be used for the treatment of cancer, including pre-cancerous, non-metastatic, metastatic, and cancerous tumors (e.g., early stage cancer), or for the treatment of a subject at risk for developing cancer, for example, breast cancer. The antibodies and antibody fragments can also be used to treat or prevent non-malignant diseases, such as neurodegenerative disorders, psychiatric disorders, or autoimmune diseases.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin (including melanoma). Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma.

In one embodiment, the multispecific antibodies specifically bind EGFR and at least one other HER receptor, such as HER2 or HER3 or HER4, and find utility in the prevention and/or treatment of solid tumors, in particular colorectal, lung (such as non-small cell lung cancer and squamous cell carcinoma), head and neck, ovarian, skin, pancreatic, and/or breast tumors.

The multispecific antibodies also find use in reducing or preventing resistance to HER pathway targeted treatment. A significant limitation in using treatments that target the HER pathway is the resistance many cancer patients exhibit to the therapeutic effects of the treatment. Some cancer patients show no response to HER pathway targeted treatment. Other cancer patients may show an initial response but then become resistant to the treatment. A cancer is resistant to a treatment if the cancer has progressed while receiving the treatment (refractory) or if the cancer has progressed within 12 months after completing a treatment regimen (relapse).

In one embodiment, the HER pathway targeted treatment comprises treatment with antibodies that target the HER pathway (for example, EGFR antibodies, HER2 antibodies, HER3 antibodies, and/or HER4 antibodies). In another embodiment, the HER pathway targeted treatment comprises treatment with a chemotherapeutic agent.

Dosages and Formulations

The antibody or antibody fragment compositions herein will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody or antibody fragment to be administered will be governed by such considerations, and is the minimum amount necessary to prevent, ameliorate, or treat a cancer. The antibody or antibody fragment need not be, but is optionally formulated with one or more agents currently used to prevent or treat cancer or a risk of developing a cancer. The effective amount of such other agents depends on the amount of antibody or antibody fragment present in the formulation, the type of disorder or treatment, and other factors discussed above. These are generally used in the same dosages and with administration routes as used hereinbefore or about from 1 to 99% of the heretofore employed dosages. Generally, alleviation or treatment of a cancer involves the lessening of one or more symptoms or medical problems associated with the cancer. The therapeutically effective amount of the drug can accomplish one or a combination of the following: reduce (by at least 10%, 20%, 30%, 40%, 50%, 60%, 70%, 80%, 90%, 100% or more) the number of cancer cells; reduce or inhibit the tumor size or tumor burden; inhibit (i.e., to decrease to some extent and/or stop) cancer cell infiltration into peripheral organs; reduce hormonal secretion in the case of adenomas; reduce vessel density; inhibit tumor metastasis; reduce or inhibit tumor growth; and/or relieve to some extent one or more of the symptoms associated with the cancer. In some embodiments, the antibody or antibody fragment is used to prevent the occurrence or reoccurrence of cancer in the subject.

In one embodiment, the present invention can be used for increasing the duration of survival of a human patient susceptible to or diagnosed with a cancer. Duration of survival is defined as the time from first administration of the drug to death. Duration of survival can also be measured by stratified hazard ratio (HR) of the treatment group versus control group, which represents the risk of death for a patient during the treatment.

In yet another embodiment, the treatment of the present invention significantly increases response rate in a group of human patients susceptible to or diagnosed with a cancer who are treated with various anti-cancer therapies. Response rate is defined as the percentage of treated patients who responded to the treatment. In one aspect, the combination treatment of the invention using an antibody or antibody fragment and surgery, radiation therapy, or one or more chemotherapeutic agents significantly increases response rate in the treated patient group compared to the group treated with surgery, radiation therapy, or chemotherapy alone, the increase having a Chi-square p-value of less than 0.005.

Additional measurements of therapeutic efficacy in the treatment of cancers are described in U.S. Patent Application Publication No. 20050186208.

Therapeutic formulations are prepared using standard methods known in the art by mixing the active ingredient having the desired degree of purity with optional physiologically acceptable carriers, excipients or stabilizers (Remington's Pharmaceutical Sciences (20.sup.th edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The antibodies and antibody fragments described herein are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with HER (e.g. EGFR, HER2, HER3, HER4 etc.) antagonism. An ex vivo strategy can also be used for therapeutic applications. Ex vivo strategies involve transfecting or transducing cells obtained from the subject with a polynucleotide encoding an antibody or antibody fragment. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the antibody or antibody fragment is administered locally, e.g., by direct injections, when the disorder or location of the tumor permits, and the injections can be repeated periodically. The antibody or antibody fragment can also be delivered systemically to the subject or directly to the tumor cells, e.g., to a tumor or a tumor bed following surgical excision of the tumor, in order to prevent or reduce local recurrence or metastasis.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 20 mg/kg (e.g. 0.1 mg/kg-15 mg/kg) of antibody can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 20 mg/kg. Thus, one or more doses of about 0.5 mg/kg, 2.0 mg/kg, 4.0 mg/kg, 10 mg/kg, 12 mg/kg, 15 mg/kg, or 20 mg/kg (or any combination thereof) may be administered to the patient. Such doses may be administered intermittently, e.g. every week, every two weeks, or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Combination Therapy

An antibody of the invention may be combined in a pharmaceutical combination formulation, or dosing regimen as combination therapy, with a second compound having anti-cancer properties. The second compound of the pharmaceutical combination formulation or dosing regimen may have complementary activities to the antibody of the combination such that they do not adversely affect each other. In one embodiment, the multispecific antibody is used in combination with another anti-HER antibody, such as HERCEPTIN®, pertuzumab, and/or cetuximab. Antibodies of the invention can also be used in combination with radiation therapy.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an antibody of the invention may also have a therapeutically effective amount of a chemotherapeutic agent such as a tubulin-forming inhibitor, a topoisomerase inhibitor, a DNA intercalator, or a DNA binder.

Other therapeutic regimens may be combined with the administration of an anticancer agent identified in accordance with this invention. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

Examples of such combination therapy include combinations with chemotherapeutic agents such as erlotinib (TARCEVA®, Genentech/OSI Pharm.), bortezomib (VELCADE®, Millenium Pharm.), fulvestrant (FASLODEX®, AstraZeneca), sutent (SU11248, Pfizer), letrozole (FEMARA®, Novartis), imatinib mesylate (GLEEVEC®, Novartis), PTK787/ZK 222584 (Novartis), oxaliplatin (Eloxatin®, Sanofi), 5-FU (5-fluorouracil), leucovorin, Rapamycin (Sirolimus, RAPAMUNE®, Wyeth), lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; antifolate antineoplastic such as pemetrexed (ALIMTA® Eli Lilly), aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics, calicheamicin, calicheamicin gamma1I and calicheamicin omegal1; dynemicin, including dynemicin A; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhône-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Such combination therapy also includes: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON•toremifene; (ii) aromatase inhibitors that inhibit the enzyme aromatase, which regulates estrogen production in the adrenal glands, such as, for example, 4(5)-imidazoles, aminoglutethimide, MEGACE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in abherant cell proliferation, such as, for example, PKC-alpha, Ralf and H-Ras; (vii) ribozymes such as a VEGF expression inhibitor (e.g., ANGIOZYME® ribozyme) and a HER2 expression inhibitor; (viii) vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; (ix) anti-angiogenic agents such as bevacizumab (AVASTIN®, Genentech); and (x) pharmaceutically acceptable salts, acids or derivatives of any of the above.

Preparation and dosing schedules for such chemotherapeutic agents may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, Md.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Articles of Manufacture and Kits

Another embodiment of the invention is an article of manufacture containing materials useful for the treatment of cancers. The article of manufacture comprises a container and a label or package insert on or associated with the container. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is a multispecific antibody or antibody fragment antibody of the invention. The label or package insert indicates that the composition is used for treating the particular condition. The label or package insert will further comprise instructions for administering the antibody composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In one embodiment, the package insert indicates that the composition is used for treating a solid tumor, such as, for example, colorectal, lung and/or breast cancer.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for purification or immunoprecipitation of HER receptors from cells. For isolation and purification of EGFR and/or HER2 and/or HER3 and/or HER4, the kit can contain an EGFR/HER2 and/or EGFR/HER3 and/or EGFR/HER4 antibody coupled to beads (e.g., SEPHAROSE® beads). Kits can be provided which contain the antibodies for detection and quantitation of the desired HER receptor in vitro, e.g., in an ELISA or a Western blot. As with the article of manufacture, the kit comprises a container and a label or package insert on or associated with the container. The container holds a composition comprising at least one multispecific antibody or antibody fragment of the invention. Additional containers may be included that contain, e.g., diluents and buffers or control antibodies. The label or package insert may provide a description of the composition as well as instructions for the intended in vitro or diagnostic use.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

EXAMPLES

Example 1

Isolation and Characterization of Antibodies Binding Human EGFR

Materials

Enzymes and M13-KO7 helper phage were purchased from New England Biolabs. *E. coli* XL1-Blue was from Stratagene. Bovine serum albumin (BSA), ovalbumin, and Tween 20 were purchased from Sigma. Neutravidin, casein and Superblock were purchased from Pierce. anti-M13 conjugated horse-radish peroxidase (HRP) was purchased from Amersham Pharmacia. Maxisorp immunoplates were purchased from NUNC (Roskilde, Denmark). Tetramethylbenzidine (TMB) substrate was purchased from Kirkegaard and Perry Laboratories (Gaithersburg, Md.).

Library Construction

Phage displayed antibody libraries were generated based on human antibody framework from humanized 4D5 (h4D5, trastuzumab), where side chain and length diversity were incorporated into heavy chain complementarity determining regions (CDR1, CDR2, CDR3) in the first library (Library 1), and into heavy chain CDRs and light chain CDR3 in the second library (Library 2) still focusing on the diversification in heavy chain as described (Lee et al., J. Mol. Biol, 340: 1073-1093 (2004)). Libraries were constructed as described (Lee et al., J. Mol. Biol, 340: 1073-1093 (2004)) except that the degenerate oligonucleotides used were modified modestly.

Sorting of the Two Libraries.

Library 1 and Library 2 were directly subjected to target (hEGFR-ECD-Fc (human EGFR extracellular domain fused to an Fc region of human IgG1) and EGFRvIII-Fc) binding selection. EGFRvIII-Fc protein is a variant of EGFR missing most of domain II (E1-P353 (not including the signal peptide)) fused to an Fc region of hIgG1. See Kuan, C-T, et al., Endocrine-Related Canc. 8: 83-96 (2001); Bigner, S H, et al., Cancer Research, 50: 8017-8022 (1990). 96-well Nunc Maxisorp plates were coated with 100 µl/well of target antigen (hEGFR-ECD-Fc, EGFRvIII-Fc) (5 µg/ml) in PBS (0.05M Sodium Carbonate buffer, pH9.6) at 4 C overnight or room temperature for 2 hours. The plates were blocked with alternating blocking agents. Phage solutions of $10^{13}$ phage/ml (3-5 OD/ml) were incubated with the coated antigens for 18 h in the first round of selection. Phage input was decreased in each round of selection as following: $1^{st}$ round 3-5 O.D/ml, $2^{nd}$ round 3 O.D/ml, $3^{rd}$ round 0.5~1 O.D/ml and $4^{th}$ round input 0.1~0.5 O.D/ml. The diluted phage was incubated for 30 minutes on ice. 1 µM of an Fc-Fusion protein was added to the blocked phage from $3^{rd}$ round to remove Fc binders. Following incubation of the phage solutions (100 µl/well to 8 target antigen-coated wells and 2 uncoated wells) on the immunoplates to allow binding to the immobilized antigen (overnight for $1^{st}$ round, 2 hours for remaining rounds), immunoplates were washed at least ten times continuously with PBS and 0.05% Tween 20. Bound phage was eluted with 100 ul/well of 100 mM HCl at room temperature for 20 minutes. The eluted phage (from coated wells) and background phage (from uncoated wells) were neutralized by adding 1/10 volume 1M Tris pH 11.0 and BSA to final 0.1%. The recovery of phage per antigen-coated immunoplate well was calculated and compared to that of a blocked well without coated antigen to study the enrichment of phage clones displaying Fabs that specifically bound the target antigen. Eluted phage were amplified in E. coli and used for further rounds of selection.

High-throughput Characterization of hEGFR Binding Clones

Random clones from round 4 were selected for screening and assayed using phage ELISA in which binding to target and anti-gD was compared to binding of non-relevant proteins (BSA, HER2, an anti-EGFR antibody, trastuzumab).

384-well format immunoplates were coated with 1 µg/ml of target, anti-gD and non-relevant proteins at 4° C. overnight or room temperature for 2 hours and blocked 1 h with 1% BSA in PBS. Phagemid clones in E. coli XL1-Blue were grown in 150 ul of 2YT broth supplemented with carbenicillin and M13-KO7 helper phage; the cultures were grown with shaking overnight at 37° C. in a 96-well format. Culture supernatants containing phage were diluted five fold in PBST (PBS with 0.05% Tween 20 and 0.5% (w/v) BSA). 30 µl of mixture was added to each quadrant of 384-well coated plate and incubated at room temperature for 1 hour. The plate was washed with PBT (PBS with 0.05% Tween 20) and incubated for 30 minutes with anti-M13 antibody horse-radish peroxidase conjugate diluted 5000-fold to 1 nM in PBST. The plates were washed, developed with TMB substrate for approximately five minutes, quenched with 1.0 M $H_3PO_4$, and read spectrophotometrically at 450 nm.

The clones that bound the anti-gD antibody and target but not the non-specific proteins were considered specific positives. VH library enabled the isolation of specific binders for both EGFR-ECD-Fc and EGFRvIII-Fc.

Solution Binding Competition ELISA

The binding affinity of selected binding clones was determined by solution binding competition ELISA.

Selected phagemid clones in E. coli XL1-Blue were grown in 20 ml of 2YT broth supplemented with carbenicillin, Kanamycin and M13-KO7 helper phage; the cultures were grown with shaking overnight at 30° C. Supernatant of phage was purified by double precipitation in 20% PEG/2.5M NaCl, resuspended in PBS, and read spectrophotometrically at 268 nM for concentration determination (in OD/ml).

Purified phage was titered on immunoplates coated with 1 µg/ml of hEGFR-ECD-Fc to determine optimal concentration for solution competition ELISA.

The dilution that gave a 1 OD/ml signal at 450 nM was used in the solution binding assay in which phage were first incubated with increasing concentration of antigen (hEGFR-ECD) for one hour and then transferred to antigen-coated immunoplates for 15 minutes to capture unbound phage. $IC_{50}$ was calculated as the concentration of antigen in solution-binding stage that inhibited 50% of the phage from binding to immobilized antigen. The solution binding competition ELISA was performed at room temperature. The $IC_{50}$ values for selected clones ranged from 36.2 nM to >1000 nM.

Conversion of Phage Displaying F(ab)zip to Human IgG

To accurately determine affinity, specificity and other properties, selected clones were expressed as free hIgG.

The variable domains of light chain and heavy chain were cloned into vectors previously designed for transient human IgG expression in mammalian cells. (Leet et al., J. Mol. Biol. 23:340:1073-1093 (2004)).

The $V_L$ region of phagemid DNA was digested with restriction enzymes, which cleaved the DNA upstream of the region encoding for CDR L1 (EcoRV) and downstream of the region encoding for CDR L3 (KpnI).

The $V_H$ region of phagemid DNA was digested with restriction enzymes, which cleaved the DNA upstream of the region encoding for CDR H1 (ApaI) and downstream of the region encoding for CDR H3 (BsiwI).

Secreted free IgG were purified with protein A affinity chromatography and tested in direct binding ELISA on hEGFR-coated immunoplates.

Comparison of Anti-hEGFR Epitopes

The ability of the isolated anti-EGFR antibodies to compete with another anti-hEGFR antibody known to bind to domain III of EGFR was studied in order to determine the epitopes recognized by the anti-hEGFR antibodies.

The assays were done in a competitive ELISA format. For the competitive ELISA, EGFR-ECD-Fc was immobilized on Maxisorp immunoplates at 2 mg/ml. A fixed concentration of the anti-EGFR antibody (or an unspecific antibody control) was captured by coated EGFR-ECD-Fc and the purified selected anti-EGFR phage-Fabs were added, and detected with α-M13-conjugated HRP. Antibodies that were blocked from binding EGFR-ECD-Fc coated plates are likely to share over-lapping epitopes.

For the TGF-α competitive ELISA, EGFR-ECD-Fc was captured first by coated anti-human Fc antibody, then a fixed concentration of TGF-α was captured by EGFR-ECD-Fc. The purified phage-Fabs were added, and detected with α-M13-conjugated HRP.

Finally, the binding of selected clones to constructs with exposed and deleted domains of EGFR was assessed to confirm previous competitive ELISA. Clone designated D1 competes with the anti-EGFR antibody and is likely to bind EGFR at domain III.

Example 2

Characterization of Antibodies Against Human Epidermal Growth Factor Receptor

Inhibition of Ligand Binding order to determine if selected anti-EGFR antibody D1 inhibits $^{125}$I-EGF binding to H1666 cells (ATCC CRL-5885, Manassas, Va.), the purified IgGs version of D1 was tested in a ligand binding assay as follows. H1666 cells were plated in 12 well plates. The next day growth medium was removed and cells were pretreated with 200 nM antibody for 2 hours at room RT. 20 µl/well of radiolabelled EGF was added (use conc. below Kd of cell line) and cells were treated for an additional 2 hours at room temperature. Cells were washed with binding buffer and solubilized, transferred and samples were counted using an iso Data γ-counter. Unlabelled EGF was used as a cold competitor. The results demonstrate that D1 inhibits $^{125}$I-EGF ligand binding to H1666 cells.

Inhibition of TGF-α Induced EGFR Phosphorylation in Stably Transfected EGFR-NR6 Cells To determine if anti-EGFR antibody D1 selectively blocks TGF-α induced EGFR phosphorylation, stably transfected EGFR-NR6 cells were serum starved for 2-3 hours and pre-incubated with various concentrations of D1 for 2 hours. Cells were stimulated with 1 nM TGF-α. Whole cell lysates were subjected to SDS-PAGE analysis, and immunoblots were probed with anti-phosphotyrosine and anti-EGFR as a loading control. A commercially available anti-EGFR antibody was used as a positive control. The data demonstrated that D1 inhibits TGF-α induced EGFR phosphorylation in a cell based assay.

Example 3

Affinity Maturation of D1

Library Construction

Two phage-displayed libraries (L3/H3 and L3/H1H2 libraries) were created using oligonucleotide-directed mutagenesis as described (Lee et al., Blood, 108, 3103-3111, 2006). The library template vectors contained a stop codon (TAA) embedded in CDR-L3, which was repaired during the mutagenesis reaction using degenerate oligonucleotides that annealed over the sequences encoding CDR-L3 (all libraries), CDR-H3 (L3/H3 library), CDR-H2 and CDR H1 (L3/H1H2 library). The library mutagenesis reactions were performed according to the method of Kunkel et al (Methods Enzymol. 1987; 154:367-82). The oligonucleotides were combined in different ratios to fine-tune the diversity to reflect the amino acid frequency in natural repertoire at selected positions. The mutagenesis products were pooled into one reaction per library and electroporated in to E. coli SS320 cells and grown supplemented with KO7 helper phage as described (Lee et al., 2004, supra).

Library Sorting and Screening

For affinity improvement selection, phage libraries were subjected to plate sorting against hEGFR-ECD-Fc for the first round, followed by three rounds of solution sorting.

Three rounds of solution sorting were performed with increasing stringency of selection Immunoplates were coated with 5 ug/ml Neutravidin overnight at 4° C. and blocked with Superblock (Pierce) and PBST. 3-5 OD/ml of propagated phage was pre-incubated with 100 nM of biotinylated EGFR-ECD in Superblock, then diluted 10× and added to blocked immunoplates for 5-10 minutes. Plates were washed 8 times, the phage were eluted and propagated for next round of solution sorting, decreasing phage input (0.5 OD/ml) and concentration of biotinylated EGFR-ECD down to 1 nM.

High Throughput Affinity Screening ELISA (Single Spot Competition)

Random clones from last round of solution sorting were picked for screening and assayed using phage single point competition ELISA in which binding to target of phage supernatant pre-incubated (or not) with hEGFR-ECD is compared.

Phagemid clones in E. coli XL1-Blue were grown in 150 ul of 2YT broth supplemented with carbenicillin and M13-KO7 helper phage; the cultures were grown with shaking overnight at 37° C. in a 96-well format. Culture supernatants containing phage were diluted five fold in PBST (PBS with 0.05% Tween 20 and 0.5% (w/v) BSA) with or without 5 nM EGFR-EC). The OD reduction (%) was calculated by the following equation:

$OD_{450nm}$ reduction (%)=($OD_{450nm}$ of wells with competitor)/($OD_{450nm}$ of well with no competitor)* 100

Clones with OD reduction greater that 25% were selected for solution binding competition ELISA.

Solution Binding Competition ELISA

The binding affinity of selected binding clones by single spot ELISA was determined by solution binding competition ELISA as described above.

The phage IC50s of one clone selected from D1 parent clone affinity maturation (D1.5) was determined as described above. The IC50 for D1.5 was 0.39 nM. D1.5 was reformatted into mIgG2A for further characterization, using same restriction site described above and vectors designed for transient murine IgG expression in mammalian cells.

Example 4

Characterization of Anti-EGFR Improved Antibodies as Free mIgG

BIAcore Measurement

Surface plasmon resonance assays on a BIAcore™-2000 was used to determine the affinity of anti-EGFR mIgG2A. Immobilized mIgG D1.5 on CM5 chips at ~150 response units (RU) were used in the BIAcore assays. Increasing concentration from 12.5 nM to 200 nM of EGFR-ECD were injected at 30 µl/min at 25° C. Binding responses were corrected by subtracting RU from a blank flow cell. For kinetics analysis, 1:1 Languir model of simultaneous fitting of $k_{on}$ and $k_{off}$ was used. The KD determined by this method for D1.5 was 1.2 nM.

Epitope Mapping

The binding of selected clones to constructs with exposed and deleted domains of EGFR was assessed to confirm inherited binding epitope from parent clones. D1.5, the affinity improved clone selected from D1 sorting, binds EGFR at domain III.

Inhibition of TGF-α Induced EGFR Phosphorylation in EGFR-NR6 Cells

D1.5 was tested to determine if it inhibited TGF-α induced EGFR phosphorylation with higher potency compared to the parental clone. The antibodies were tested on EGFR-NR6 cells and the assay was performed as described above in Example 2. A commercially available anti-EGFR antibody was used as a positive control.

The results demonstrate that D1.5 showed a greater inhibition of ligand induced EGFR phosphorylation when compared with parent clone D1.

Inhibition of Cell Proliferation in H1666 Cells

An assay was performed to determine whether D1.5 inhibits cell proliferation of a NSCLC cancer cell line, H1666, that expresses EGFR, HER2 and HER3 at moderate levels. H1666 cells (ATCC CRL-5885, Manassas, Va.) were seeded in 96 well plates at a density of 5000 cells. The following day cells were simultaneously treated with various concentrations of antibody (up to 50 ug/ml) in 1% serum containing medium. After 3 days Alamar Blue was added and fluorescence was detected using a fluorometer. The results were expressed in RFUs.

The results demonstrate that D1.5 showed a greater inhibition of cell growth than D1.

A431 Xenograft Study

An A431 xenograft model was used to validate the in-vivo efficacy of affinity matured anti-EGFR antibody D1.5. A431 cells are EGFR amplified and respond very well to anti-EGFR agents. The study was conducted in nu/nu mice and a commercially available anti-EGFR antibody was used as a reference.

In a first step, the cross-reactivity of D1.5 with murine EGFR was assessed in a competitive ELISA. Immunoplates were coated with hEGFR-ECD-Fc. Serial dilutions of mEGFR-ECD-Fc were incubated with fixed concentration of D1.5. The results show that D1.5 cross-reacted with murine EGFR. To assess the dosing needed for the in vivo efficacy study, D1.5 was first injected at a single dose (50 mg/kg) and serum IgG concentration were measured by ELISA. D1.5 was cleared more rapidly and diminishing concentrations were seen after seven days post injection. The efficacy study (A431 xenograft model) revealed that D1.5 inhibited tumor growth completely. D1.5 was as effective as the anti-EGFR antibody at 50 mg/kg. Its reduced potency in the lower dose group (25 mg/kg) was due to the faster clearance of the antibody. (FIG. 1.)

Example 5

Light Chain Library Design and Screening for Bispecific Antibodies

Libraries Design and Construction

Libraries based on a D1.5 template were designed for diversifying the amino acid composition and CDR length of antibody light chain. A subset of the randomized positions were tailored to represent amino acids which are part of the natural repertoire at these sites, whereas the remaining sites were randomized to include all 20 naturally occurring amino acids. In addition, randomized positions in CDR L3 were tailored and biased toward the native sequence of the template because this CDR is considered important for the binding of D1.5. For CDR L1, each length was a mix of three oligonucleotides containing codons for positions 28-33. For longer L1, NNK was inserted in between position 30 and 31.

| | Positions | | | | | |
|---|---|---|---|---|---|---|
| | 28 | 29 | 30 | 31 | 32 | 33 |
| CDR-L1 | $G_{70}A_{70}C_{70}$ | RTT | NNK | NNK | TAC | STA |
| | $G_{70}A_{70}C_{70}$ | RTT | NNK | NNK | DGG | STA |
| | $G_{70}A_{70}C_{70}$ | RTT | NNK | NNK | NMT | STA |

For CDR L2, four oligonucleotides were mixed 1:1:2:10.

| | 50 | 51 | 52 | 53 |
|---|---|---|---|---|
| CDR-L2 | NKK | GST | TCC | NNK |
| | TGG | GST | TCC | NNK |
| | KGG | GST | TCC | TMT |
| | NKK | GST | TCC | TMT |

N=A/C/G/T, D=A/G/T, V=A/C/G, B=C/G/T, H=A/C/T, K=G/T, M=A/C, R=A/G, S=G/C, W=A/T, Y=C/T.

*$G_{70}A_{70}C_{70}$ allows 70% of the designated nucleotide and 10% each of the other three to encode approximately 50% Glu and 50% of the other amino acids. See US Patent Publication No. 20080069820 and Bostrom, J. et al., Science 323:1610-1614 (2009).

The diversity for CDR L3 is derived from the mixture of the following oligonucleotides. D1.5 CDR_L3 oligonucleotides

F693
(SEQ ID: 70)
ACTTATTAC TGT CAG CAA 878 NNK 776 RST CCT TAC ACG TTC GGA

F694
(SEQ ID: 71)
ACTTATTAC TGT CAG CAA 878 TAC 776 RST CCT TAC ACG TTC GGA

F695
(SEQ ID: 72)
ACTTATTAC TGT CAG CAA DGG NNK 776 577 CCT TAC ACG TTC GGA

F696
(SEQ ID: 73)
ACTTATTAC TGT CAG CAA KMT NNK 776 577 CCT TAC ACG TTC GGA

F697
(SEQ ID: 74)
ACTTATTAC TGT CAG CAA 878 NNK 776 NNK CCT TAC ACG TTC GGA

F698
(SEQ ID: 75)
ACTTATTAC TGT CAG CAA DGG NNK NNK RST CCT TAC ACG TTC GGA

F699
(SEQ ID: 76)
ACTTATTAC TGT CAG CAA KMT NNK NNK RST CCT TAC ACG TTC GGA

5=70% A, 6=70% G, 7=70% C, 8=70% T (10% for the rest of three nucleotides)

In all of the libraries the heavy chain was held constant with the parent clone sequence. All library templates contained a stop codon embedded in CDR L1 preventing the presence of template light chain among the phage-displayed antibody library members.

Libraries were constructed by mutagenesis method (Kunkel mutagenesis) using the single strand DNA template containing stop codon to anneal with the sets of oligonucleotides for three CDR L1, L2 and L3 simultaneously. Library DNA from mutagenesis were transformed into bacterial cell strain SS320 by electroporation and grown up with helper phage KO7. Single colonies from constructed libraries were evaluated for display levels by the detection of gD Tag at the c-terminus of light chain and for the retention of binding for primary antigen (EGFR) in a single spot ELISA format. An average of 35% of evaluated single colonies from D1.5 libraries, show a high level of display and retained EGFR binding property.

Library Sorting and Screening for the Isolation of Dual Specific Clones

The libraries were subject to an initial round of binding selection with anti-gD antibody as the capture target to eliminate clones in which the Fab gene had been deleted or were not expressed, and binding selection with hEGFR-ECD-Fc, followed by 4 rounds of plated antigen selection (HER2-ECD, HER2-ECD-Fc, HER2-I-III-Fc, HER3-ECD-Fc, HER4-ECD-Fc (in each case the Fc in the fusion constructs is the complement binding fragment from hIgG1). Alternatively, they were directly subjected to target binding selection without pre-selection with anti-gD and hEGFR-ECD-Fc.

Each round of plate selection was performed as previously described in Example 3. Random clones from round 3 and 4 were selected for screening and assayed using phage ELISA in which binding to target and anti-gD was compared to binding of a non-relevant protein (BSA) for checking non-specific binding. Clones that bound the anti-gD antibody and target but not the non-targeted protein controls (such as bovine serum albumin, other IgGs) were considered specific positives.

The light chain variable domain regions of the positive clones were amplified by PCR and sequenced. The DNA sequence analysis of the positive specific binders revealed 1 unique binder for both EGFR and HER2 (D1.5-201 (SEQ ID NO: 36)), 7 unique binders for both EGFR and HER3 (D1.5-100 (SEQ ID NO: 40), D1.5-103 (SEQ ID NO: 41), D1.5-113 (SEQ ID NO: 42), D1.5-115 (SEQ ID NO: 43), D1.5-116 (SEQ ID NO: 44), D1.5-121 (SEQ ID NO: 45), D1.5-122 (SEQ ID NO: 46)), 1 unique binder for both EGFR and HER4 (D1.5-400, (SEQ ID NO: 39)).

Eight out of the nine bispecific clones retained the proline at position 93 in HVR L3, Since the adoption of proline at this position (with tyrosine at position 96) dramatically increased D1.5 affinity for EGFR compared to its parent clone D1, it is likely that it is a contributor in retention of binding for EGFR.

Evaluation of Bispecific hEGFR/HER2, hEGFR/HER3, hEGFR/HER4 Phage Clones Specificity.

To determine if the nine clones with dual activities were specific to their cognate targets, their binding to a panel of antigens in a direct plate ELISA format was evaluated.

2 µg/ml of several proteins were coated on immunoplates overnight at 4° C. The plates were blocked with 1% BSA in PBST, and a dilution of phage-Fab supernatant grown as described in Example 1 was applied to the plate for 30 minutes.

Figure 2:
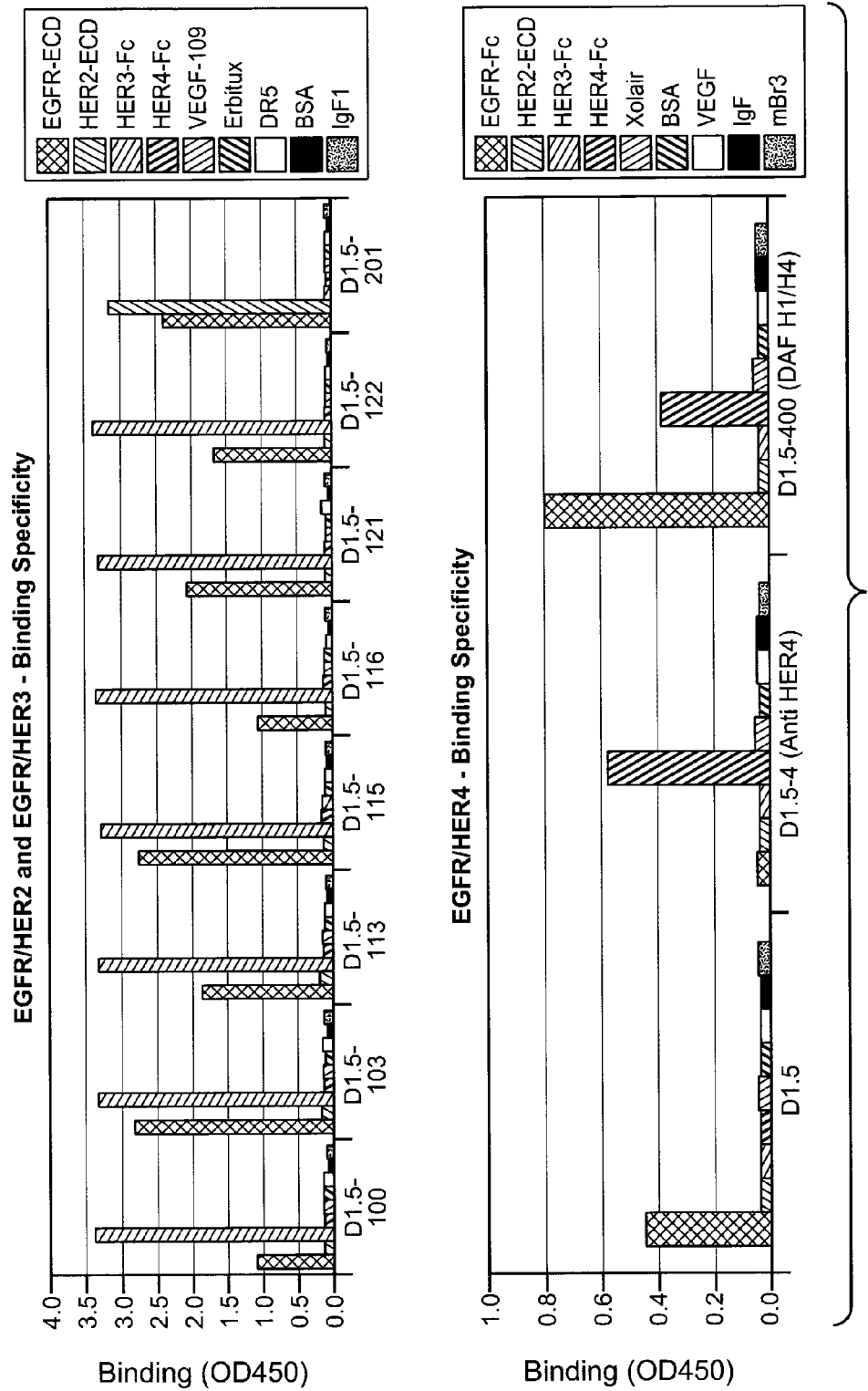
FIG. 2 shows the binding specificity of clones with dual specificity.

The plates were washed and binding signals recorded and analyzed as described in Example 1. The results show that all clones with dual specificities were specific to their cognate target. Clones D1.5-4 and parent clone D1.5 were used as control. (FIG. 2.)

Example 6

Characterization of Antibodies with Dual Specificity as Free mIgG

All clones with dual specificity were reformatted into mIgG2A for further characterization, using same restriction site described above, and vectors previously designed for transient murine IgG expression in mammalian cells.

Inhibition of TGF-α1 Induced EGFR Phosphorylation in EGFR-NR6 Cells

Figure 3:
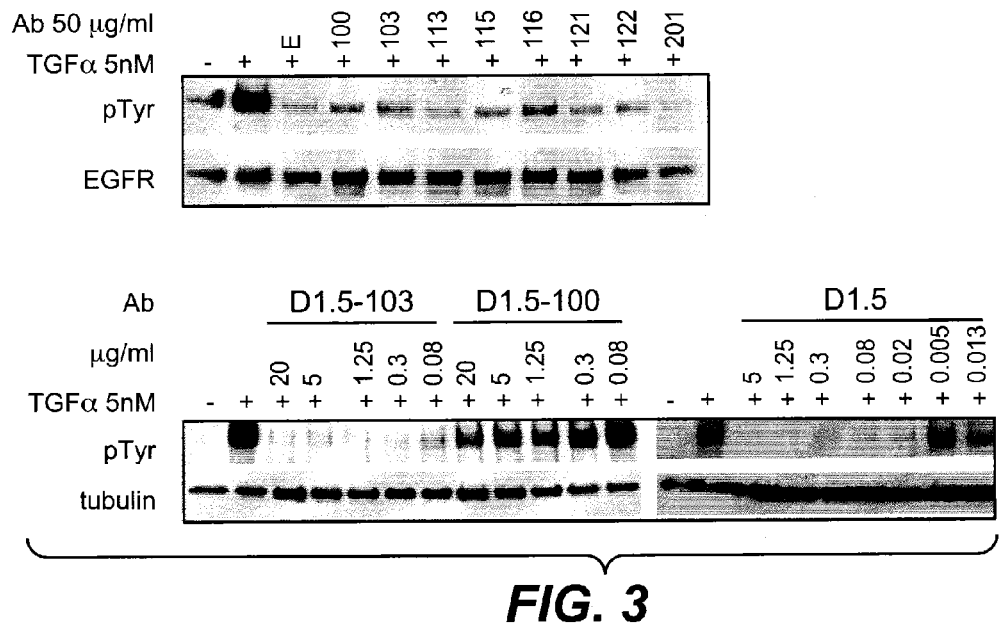
FIG. 3 shows the inhibition of TGF-α-induced EGFR phosphorylation using selected antibodies having dual specificity (anti-EGFR/HER3 and anti-EGFR/HER2 antibodies).

To determine if the seven selected antibodies with dual specificity block TGF-α induced EGFR phosphorylation, stably transfected EGFR-NR6 cells were treated as described in Example 2. The data in FIG. 3 demonstrate that EGFR/HER3 and EGFR/HER2 antibodies inhibited TGF-α induced EGFR phosphorylation at high concentration. A commercially available anti-EGFR antibody was used as a positive control.

A dose response on clones D1.5-100 and D1.5-103 showed that clone D1.5-100 lost its parent clone's (D1.5) high potency to inhibit EGFR phosphorylation. D1.5-103, however, had a similar potency to D1.5 in this assay.

Inhibition of Heregulin Binding to HER3 by Anti-EGFR/HER3 Antibodies

To determine whether the selected anti-EGFR/HER3 antibodies could inhibit heregulin binding to HER3-ECD-Fc protein, purified IgGs were tested in a radiolabeled ligand binding assay.

Figure 4:
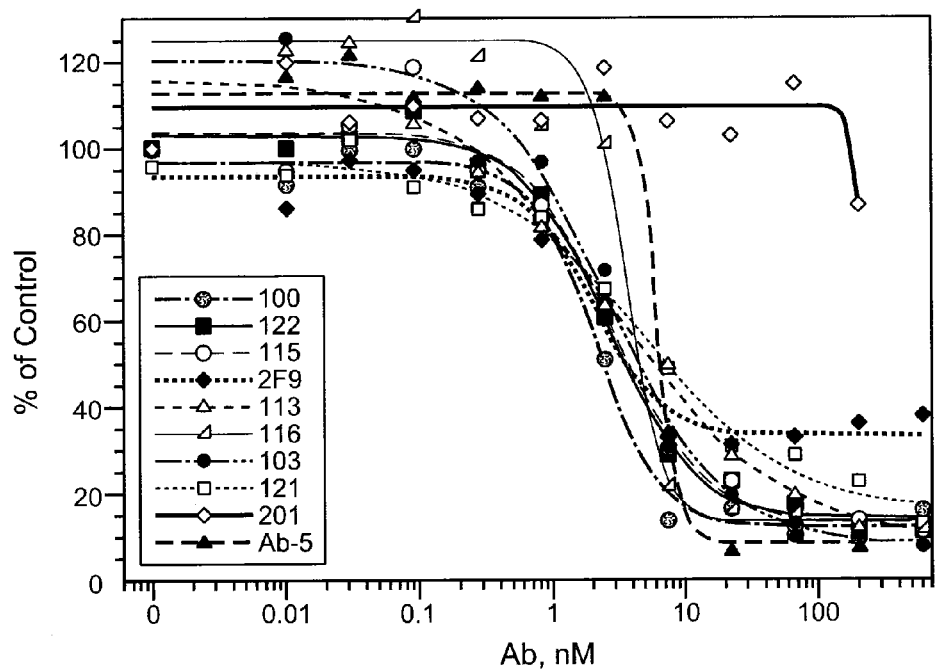
FIG. 4 shows that anti-EGFR/HER3 antibodies block heregulin binding to HER3-ECD-Fc.

Binding assays were performed in Nunc break-apart strip wells. Plates were coated at 4° C. overnight with 100 µl of 5 mg/mL goat anti-human Ab in 50 mM carbonate buffer (pH 9.6). Plates were rinsed twice with wash buffer (PBS/0.005% Tween20) and blocked with 100 µl 1% BSA/PBS for 30 min. Buffer was removed and each well was incubated with 200 ng of HER3-ECD-Fc in 1% BSA/PBS for 1.5 h. Plates were rinsed three times with wash buffer and antibodies in 1% BSA/PBS were pre-bound to HER3-IgG at 4° C. overnight. $^{125}$I-HRG was added and plates were incubated for 2 hours at room temperature. Plates were rinsed three times and individual wells were counted using a 100 Series Iso Data γ-counter. (FIG. 4.) The results demonstrate that all seven antibodies with dual specificity for EGFR and HER3 can inhibit heregulin binding to HER3-ECD-Fc.

Inhibition of Heregulin Binding to HER4 by Anti-EGFR/HER4 Antibody

To determine whether the selected anti-EGFR/HER4 antibody D1.5-400 could inhibit heregulin binding to HER4-ECD-Fc a ligand binding assay as described above was performed. 25 ng HER4-ECD-Fc was used instead of HER3-ECD-Fc. The results demonstrate that D1.5-400 inhibited heregulin binding to HER4.

Inhibition of Heregulin Induced HER2/HER3 Phosphorylation in MCF7 Cells.

Figure 5:
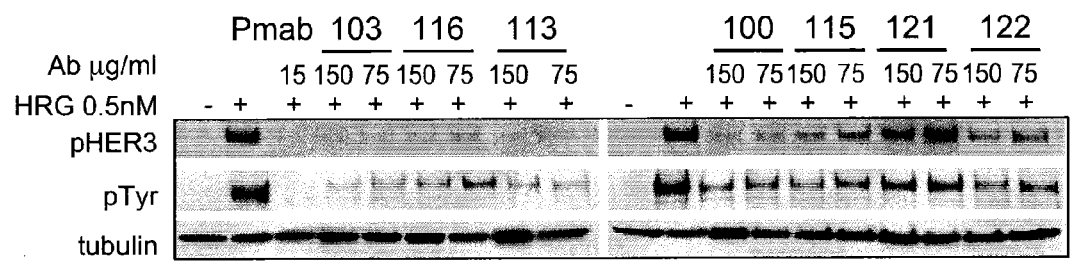
FIG. 5 shows the inhibition of HRG-induced receptor phosphorylation in MCF7 cells by anti-EGFR/HER3 bispecific antibodies.

To determine whether the seven selected antibodies with dual specificity for EGFR and HER3 could inhibit heregulin induced HER2/HER3 phosphorylation in MCF7 cells, they were tested in a receptor phosphorylation assay: MCF-7 cells (ATCC HTB 22, Manassas, Va.) were plated in 12 well plates. Following serum starvation, cells were incubated with indicated antibodies (75 ug/ml or 150 ug/ml) for 2 hours. Cells were stimulated with 0.5 nM HRG for 8 minutes and total cell lysates were run on SDS-PAGE and Western blots were probed with anti-phospho-HER3, anti-pTyr or anti-tubulin as loading control. (FIG. 5.) The results demonstrate that all anti-EGFR/HER3 antibodies inhibited heregulin induced HER2/HER3 phosphorylation at high concentration. Pertuzumab (Pmab) was used as a positive control.

Inhibition of MDA-175 Cell Proliferation

Figure 6:
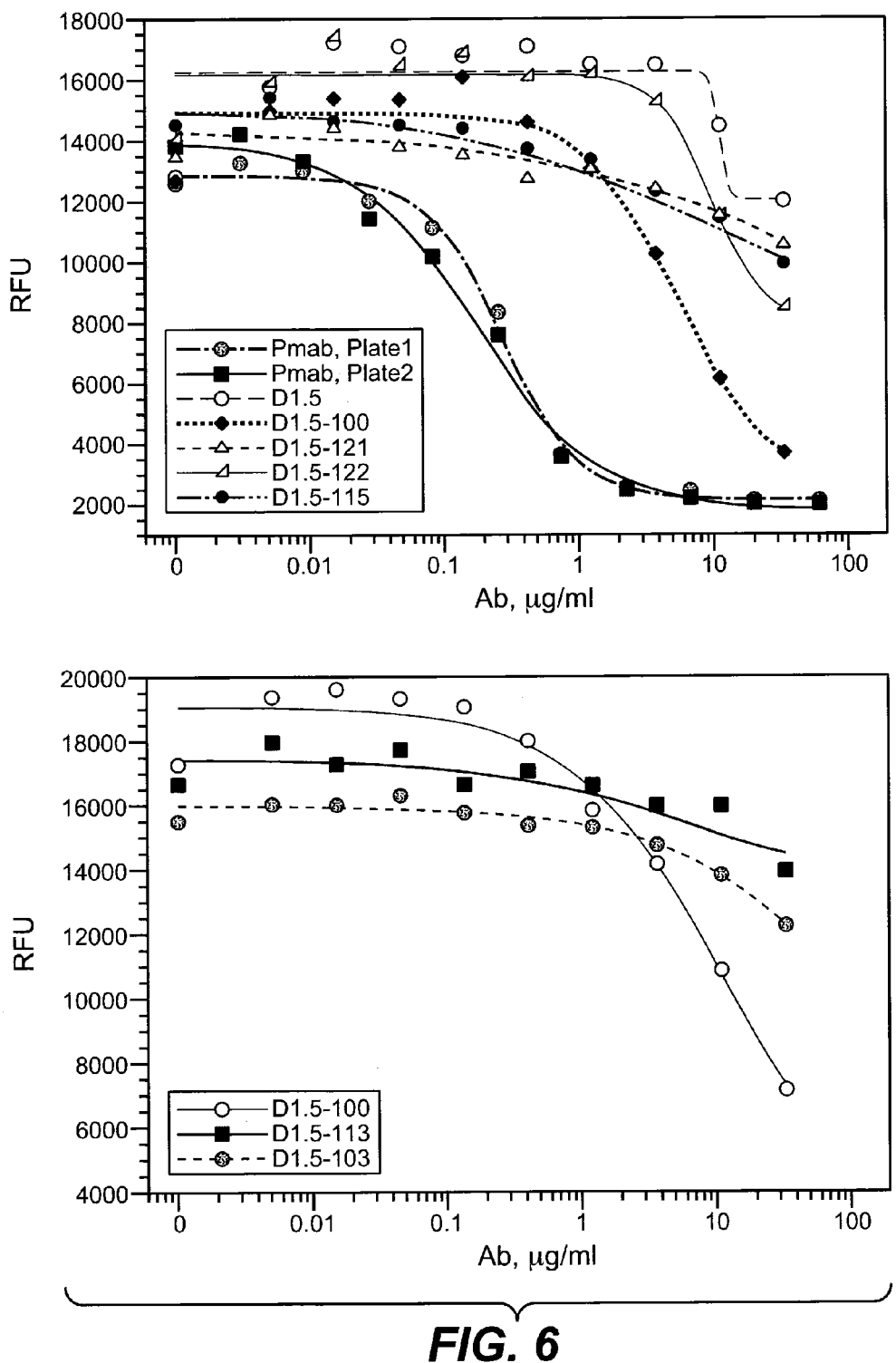
FIG. 6 shows the inhibition of cellular proliferation of MDA-175 cells by anti-EGFR/HER3 antibodies.

To determine the growth inhibitory potential of anti-EGFR/HER3 antibodies on HRG driven cell growth, MDA-175 cells (ATCC HTB 25, Manassas, Va.) (20000 cells/well) were plated in 96 well plates. The following day cells were simultaneously treated with various concentrations of antibody (up to 50 ug/ml) in 1% serum containing medium. After either 4 days or 5 days, Alamar Blue was added and fluorescence was detected using a fluorometer. The results were expressed in RFUs. MDA-175 cells were chosen since their growth is the result of an autocrine stimulation by HRG. The anti-EGFR/HER3 antibody D1.5-100, and clone D1.5-122 showed inhibition of MDA-175 cell growth. Pertuzumab (Pmab) was used as a positive control. (FIG. 6.)

Example 7

Mutagenesis Mapping Study of D1.5-100 and D1.5-103, Anti-hEGFR/HER3 Bi-Specific Antibodies An alanine and homolog shotgun scanning analysis was performed using combinatorial phage displayed libraries (Vajdos et al., J. Biol. Biol. 320:415-28 (2002)) to investigate the interaction between each antibody with its two antigens, EGFR and HER3.

Binding selections on the antigens (hEGFR and HER3) to isolate functional clones followed by DNA sequencing enabled calculations of wild-type/mutant ratios at each varied position. These ratios were then used to determine the contribution of each scanned side-chain to EGFR and HER3 binding.

The results enabled mapping of the functional paratope for binding EGFR and HER3.

D1.5-100 and D1.5-103 Shotgun Libraries Design

Solvent exposed residues in the CDRs were scanned using phage-displayed libraries in which the wild type residues were allowed to vary as either alanine or wild type (Alanine Scan) or as a homolog residue or wild type (Homolog Scan). The nature of the genetic code required some other substitutions to be included in the library in addition to Wt/Alanine or Wt/Homolog residues. Separate heavy chain and light chain alanine and homolog scanning libraries were constructed. The degeneracy ranged from $1.3 \times 10^5$ to $7.5 \times 10^7$.

Construction of Shotgun Scanning Libraries

Libraries were constructed as previously described except that a single Fab was expressed on the surface of bacteriophage fused to C-terminal domain of the M13 gene-3 minor coat protein, after removal of leucine zipper from original plasmid by kunkel mutagenesis (Oligo F220: TCT TGT GAC AAA ACT CAC AGT GGC GGT GGC TCT GGT). (SEQ ID NO: 77)

The light chain alanine and homolog scanning library had stop codons in HVR-L1, HVR-L2 and HVR-L3 and the heavy chain alanine and homolog libraries contained stop codons in each heavy chain HVRs. The libraries were constructed by previously described methods (Sidhu et al., J. Mol. Biol. 338:299-310 (2004)), using Kunkel mutagenesis (Kunkel et al., 1987, supra) on the respective stop templates. Alanine scanning libraries are phage displayed libraries that allow selected side chains to vary as wild-type or alanine. Homolog scan means that the phage displayed libraries allow selected side chains to vary as wild-type or similar amino acids.

Library Selection

NUNC 96-well Maxisorp immunoplates were coated with 5 mg/ml capture target (EGFR-ECD-Fc, HER3-ECD-Fc or Protein-L) and blocked with 1% BSA (w/v) in PBS. Phage from the above-described libraries were propagated with KO7 helper phage (NEB) as described (Lee et al., 2004, supra). The library phage solutions were added to the coated plates at a concentration of $10^{13}$ phage particles/ml and incubated for 1-2 h in RT. The plates were washed 8 times with PBST and followed by elution of bound phage with 0.1 M HCl for 30 min. Enrichment after each round of selection was determined as described previously. After 2 rounds of target selection, a number of random clones from each library were selected for sequencing as described (Sidhu et al., 2004, supra).

The DNA sequences of binding clones were used to determine wild-type/mutation ratios at each varied position. The ratios were used to assess binding contribution to antigen of each selected side chain. Dividing wt/mut ratio from antigen selection by wt/mut ratio from display selection provides quantitative estimate of each mutation's effect on antigen-binding affinity (Function ratio $F_{wt/mut}$). If the ratio is greater than 1, the mutation is deleterious. If the ratio is less than 1, the mutation is beneficial. 2500 clones were sequenced.

Figure 7:
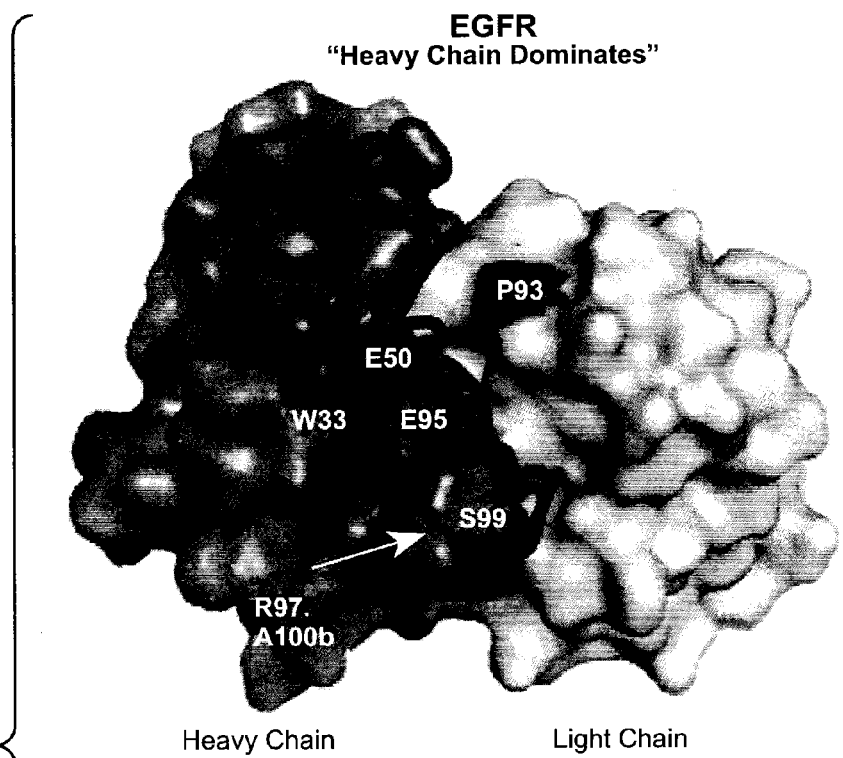
FIG. 7 is an image showing the D1.5-100 hot spots mapped on 4D5-Fv structure.
Figure 7:
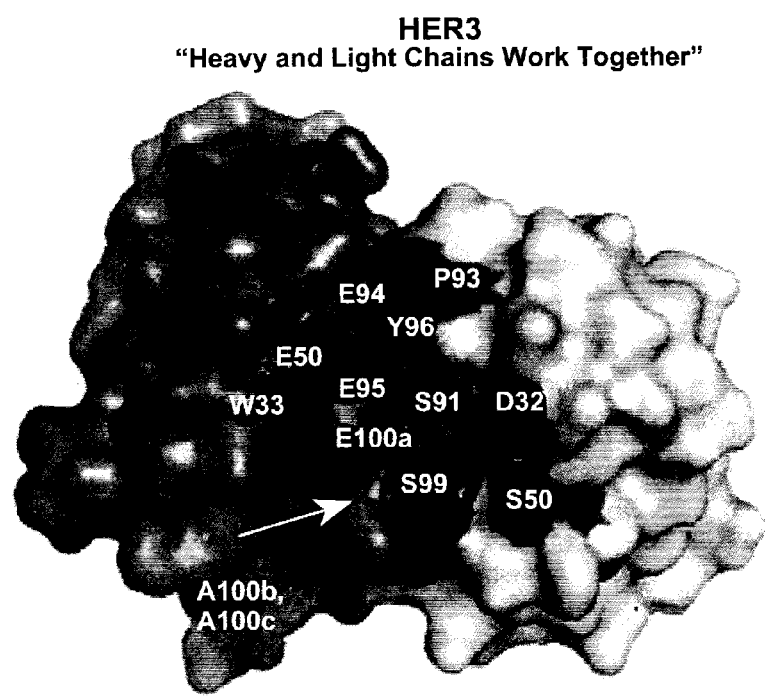

Based on the alanine and homolog scan results, hot spots of the antibody D1.5-100 for the binding of EGFR and HER3 were mapped on the structure of known anti-HER2 antibody 4D5-Fv. As shown in FIG. 7 the mapping suggests that for EGFR binding, the heavy chain dominates, and heavy and light chains work together for the binding of HER3. Acidic (E, D) residues play an important role in binding both EGFR and HER3, and especially HER3.

Affinity Maturation

Figure 8:
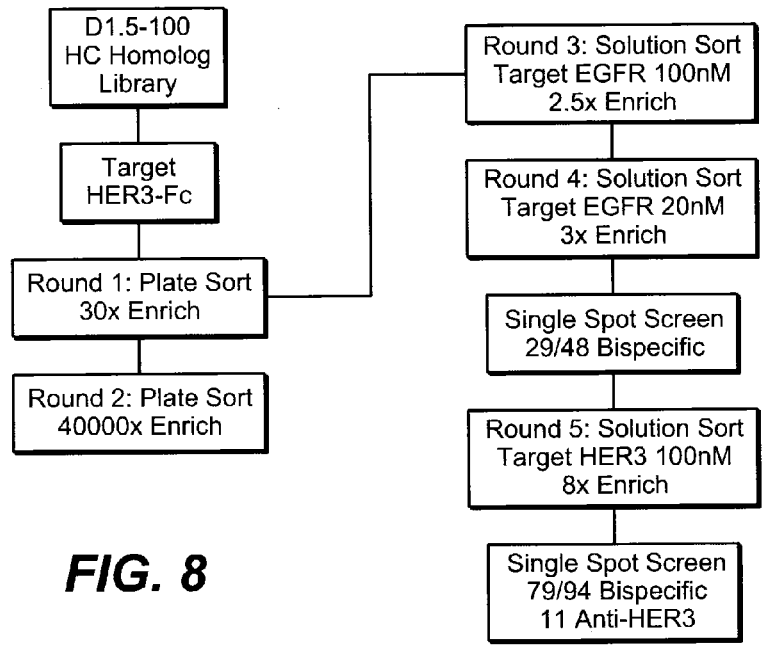
FIG. 8 outlines a strategy for affinity maturation of D1.5-100 EGFR-HER3 antibody using shotgun libraries.

FIG. 8 illustrates affinity maturation of D1.5-100, using the shotgun libraries described above. In this affinity maturation strategy, D1.5-100 heavy chain homolog library was sorted as previously described. After two rounds of plate sorting was performed on HER3-ECD-Fc coated plates, and three rounds of solution alternating targets were sorted (EGFR-ECD and HER3-ECD-Fc) under increasing stringency. Single clones were picked and assessed in a single spot ELISA to isolate clones that retained dual binding activity. Among the clones assessed, 79 of 94 show binding for both EGFR/HER3, while 11 lost EGFR binding and show specific binding for HER3.

Isolation of Clones by Single Spot Competition

Single colonies from the last round of sort were picked and phage were grown as described in Example 1. 384 wells were coated with EGFR-ECD-Fc at 1 μl/ml. For each colony grown, 25 μl of phage supernatant or ELISA buffer were incubated with 25 μl of EGFR-ECD (50 nM) and HER3-ECD-Fc (10 nM). 4 μl of incubation was added to EGFR-ECD-Fc coated plate, and the plate was washed eight times. 60 μl of 1/5000 anti-M13-HRP conjugates antibody was added, the plate was washed eight times and developed with TMB+$H_3PO_4$.

Eight unique clones were selected that show greater inhibition than D1.5-100 for EGFR and HER3, using the following single spot competition protocol:

1. Single colonies from last round of sort were picked and phage growth as previously described;
2. 384 wells plate was coated with EGFR-ECD-Fc at 1 μg/ml;
3. For each colony grown, 25 μl of phage supernatant or ELISA buffer were incubated with 25 μl of EGFR-ECD (50 nM) and HER3-ECD-Fc (10 nM);
4. 4 μl of incubation was added to EGFR-ECD-Fc coated plate;
5. Plate was washed 8 times;
6. Added 60 μl of 1/5000 anti-M13-HRP conjugates antibody;
7. Plate was washed 8 times;
8. Plate was developed with TMB+$H_3PO_4$.

8 unique clones were selected that show greater inhibition than D1.5-100 for both EGFR and HER3 (DL6, SEQ ID NO: 63; DL7, SEQ ID NO: 64; DL8, SEQ ID NO: 65; DL9, SEQ ID NO: 66; DL10, SEQ ID NO: 67; DL11, SEQ ID NO: 28; DL12, SEQ ID NO: 68; DL13, SEQ ID NO: 69). For anti- HER3 antibodies, 7 unique clones were selected that show greater inhibition than D1.5-100 for HER3.

Characterization of Affinity-matured Bispecific and Anti-HER3 Antibodies

Figure 9:
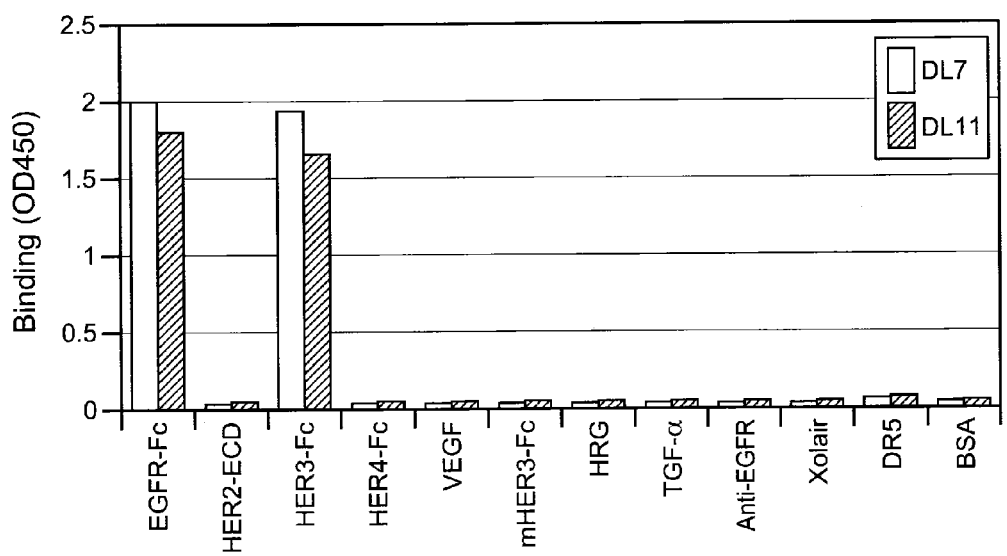
FIG. 9 shows that two selected affinity matured antibodies (DL7 and DL11) are specific for both EGFR and HER3.

Specificity of binding of selected affinity matured bispecific antibodies was assessed by direct binding to a panel of various proteins as described in Example 5. As shown in FIG. 9, the selected antibodies showed specificity of binding for both EGFR and HER3.

IC50 values were calculated for two selected bispecific antibodies (DL7 and DL11) as described in Example 1 and compared to D1.5-100 parent clone. Both selected bispecific antibodies show similar affinity for HER3-ECD-Fc and increased affinity for EGFR. DL1.5-100 had an IC50 of 44 nM for EGFR-ECD, 0.1 nM for HER3-FC; DL7 had an IC50 of 6.1 nM for EGFR-ECD, 0.25 nM for HER3-FC; DL11 had an IC50 of 5.7 nM for EGFR-ECD, 0.43 nM for HER3-FC.

The specificity of binding of selected anti-HER3 antibodies was assessed by direct binding to a panel of various proteins as previously described. The selected antibodies (DL3.5, DL3.6, DL3.7) show binding specificity for HER3 only.

Phage IC50 values were calculated for selected antibodies as described above and compared to the D1.5-100 parent clone. All antibodies (DL3.1-3.7) show increased affinity for HER3-ECD-Fc with IC50s of between 1 and 3.8 nM. The parent DL1.5-100 had an IC50 of 4.6 nM.

Binding of selected bispecific antibodies and anti-HER3 antibodies was compared to the binding of HER3 domain III protein (N-term His tag) using the competition ELISA described above. EGFR/HER3 and monospecific anti-HER3 antibodies have similar affinities for HER3 ECD-Fc and HER3 domain III constructs (Phage IC50).

Selected affinity matured bispecific antibodies and anti-HER3 antibodies were reformatted into mIgG2A and validated in a competition ELISA, as described above. mIgG2A bispecific antibodies show increased affinity for both EGFR-ECD and HER3 domain III compared to the D1.5-100 parent clone.

Using BIAcore 300 for the kinetic analysis of affinity matured EGFR/HER3 antibodies DL7 and DL11, and anti-HER3 specific antibodies DL3.6 and DL3.7, purified mIgG2A of each antibody (DL1.5-100, DL7, DL11, DL3.6, DL3.7) was coupled onto a CM5 chip, and several dilutions of antigen (EGFR-ECD, HER3 domainIII, HER3-ECD) were flowed over the coated chip under the conditions described in Example 4. The CM5 chip was regenerated between each injection of antigen. Finally, KD was determined using a 1:1 binding analysis with mass transfer. The affinity matured EGFR/HER3 antibodies DL7 and DL11 have improved KD (M) for both targets.

In order to assess the inhibitory function of affinity matured antibodies DL7, DL11 and parental antibody D1.5 on EGFR, EGFR-NR6 cells that only express EGFR were pretreated with various amounts of antibodies (up to 20 ug/ml) for one hour and, subsequently, phosphorylation of EGFR was induced by TGF (5 nM). Inhibition of receptor phosphorylation by the antibodies was detected using an anti-Phosphotyrosine antibody. Inhibitions of MAPK activation was also seen in a dose dependent manner. Antibody DL11 was more potent than DL7 in inhibiting EGFR and ERK1/2 phosphorylation. (FIG. 10A.)

The inhibitory function of DL7, DL11 and monospecific anti-HER3 antibody DL3.6 on HER3 transactivation was compared. (FIG. 10B.) MCF-7 cells that express HER2, HER3 and EGFR were pretreated with indicated amounts of antibody (up to 50 ug/ml) for one hour, and activation of HER3 and transphosphorylation of HER3 was induced by HRG. Inhibition of HER3 phosphorylation was detected using an anti-phospho HER3 antibody. Inhibition of downstream signaling molecules, ERK1/2 as well as Akt, was seen in a dose dependent manner. DL11 again was more potent than DL7.

Figure 11A:
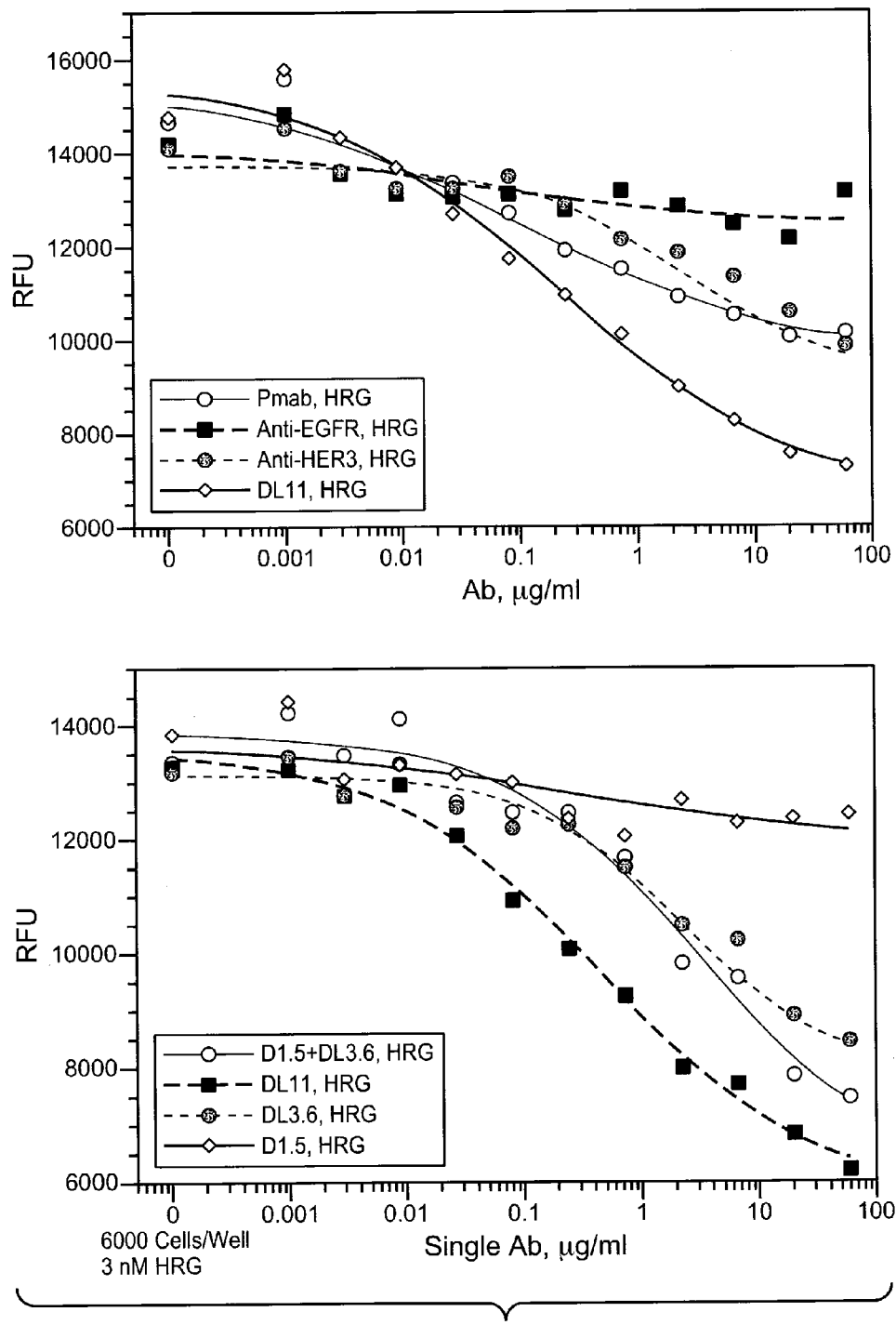
FIG. 11A) Provides graphs showing the comparison of growth inhibitory function of DL11 compared to pertuzumab, an anti-EGFR antibody, and an anti-HER3 antibody, or DL3.6, D1.5, or the combination of D1.5 plus DL3.6 on H1666 cells, a NSCLC cell line that expresses HER2, HER3, EGFR and EGFR ligands, growth stimulated with HRG. B) Provides graphs showing the comparison of growth inhibitory function of DL11 compared to pertuzumab, an anti-EGFR antibody and an anti-HER3 antibody, or DL3.6, D1.5 or the combination of D1.5 plus DL3.6 on H1666 HSCLC line, growth stimulated with HRG and TGF.

The growth inhibitory function of DL11 was compared to that of a commercially available anti-EGFR antibody, pertuzumab, and an anti-HER3 antibody, or to that of DL3.6, D1.5, or the combination of D1.5 plus DL3.6. H1666 cells (ATCC CRL-5885, Manassas, Va.) (an NSCLC cell line that expresses HER2, HER3, EGFR and EGFR ligands) (6000 cells/well) were growth stimulated with HRG (3 nM). The antibodies were tested in a dose dependent manner and growth inhibitory characteristics compared to all other monospecific antibodies. As shown in FIG. 11A, DL11 inhibited cell growth to a greater extent than the monospecific antibodies, or combinations thereof.

Figure 11B:
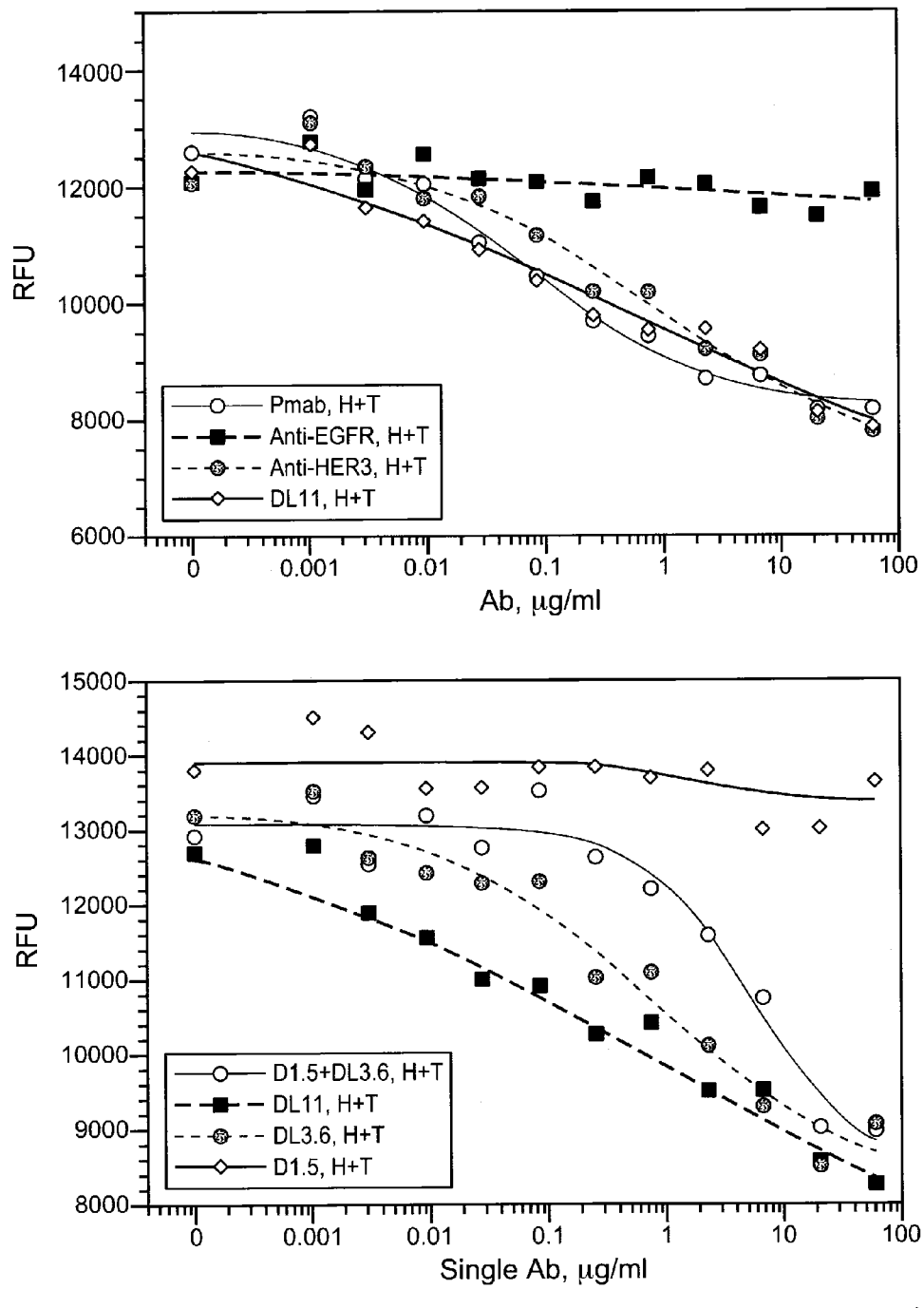

Similar results were obtained when the assay was repeated using H1666 cells growth stimulated with HRG (3 nM)+ TGFα (6 nM). (FIG. 11B).

Figure 12A:
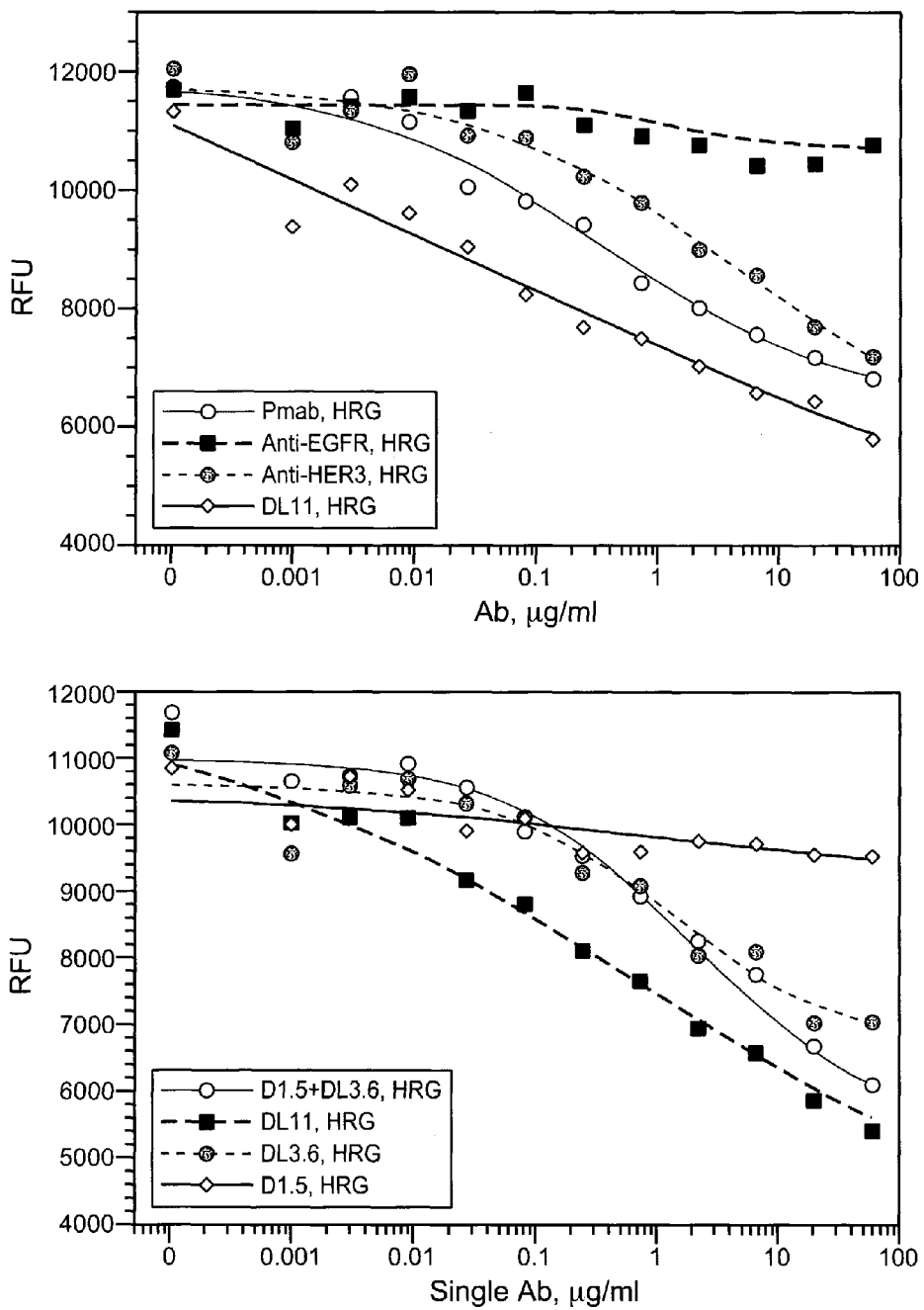
FIG. 12A) Provides graphs showing inhibition of the proliferation of HCA-7 cells, a colorectal cancer cell line that expresses HER2, HER3 and EGFR by DL11 as compared to pMab, an anti-EGFR antibody, and anti-HER3 antibody. Cell growth was stimulated with HRG. B) Provides graphs showing inhibition of HCA-7 cell growth as in FIG. 12A except that cell growth was stimulated with HRG plus TGF.

The growth inhibitory function of DL11 was compared to pertuzumab, an anti-EGFR antibody, and an anti-HER3 antibody, or DL3.6, D1.5 or to the combination of D1.5 plus DL3.6 in HCA-7 cells. HCA-7 is a colorectal cell line that expresses HER2, HER3 and EGFR. Cell growth was stimulated with HRG (3 nM) in the presence of 1% serum. The antibodies were tested in a dose dependent manner and cell viability was detected after 3 days, using Alamar Blue reagent. As shown in FIG. 12A, DL11 showed superior growth inhibitory characteristics compared to all other treatments.

Figure 12B:
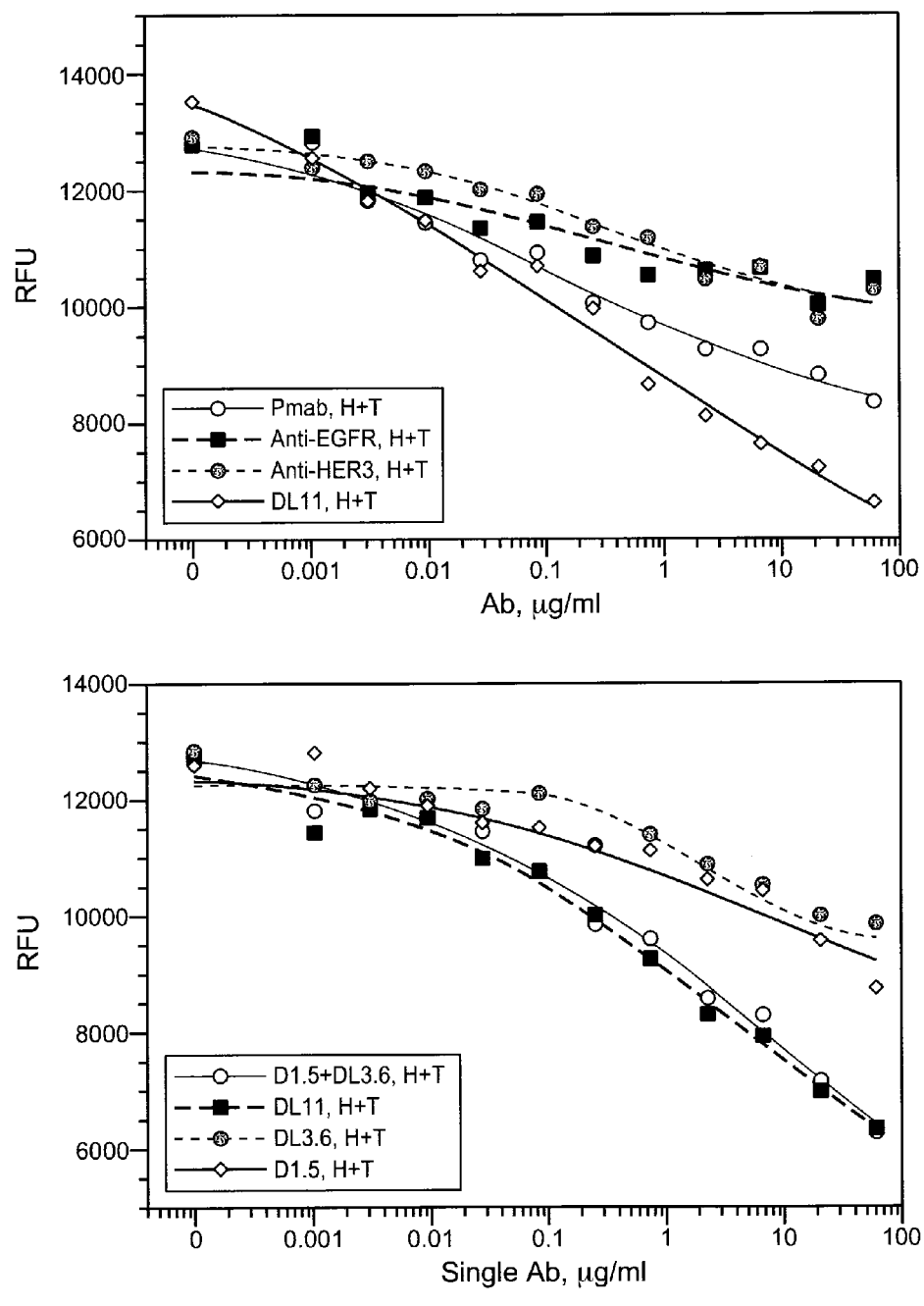

Inhibition of HCA-7 cell growth was investigated as described in connection with FIG. 12A, except growth was stimulated with HRG (3 nM) plus TGFα (5 nM). As shown in FIG. 12B, DL11 showed superior growth inhibitory characteristics compared to all other treatments.

Figure 13:
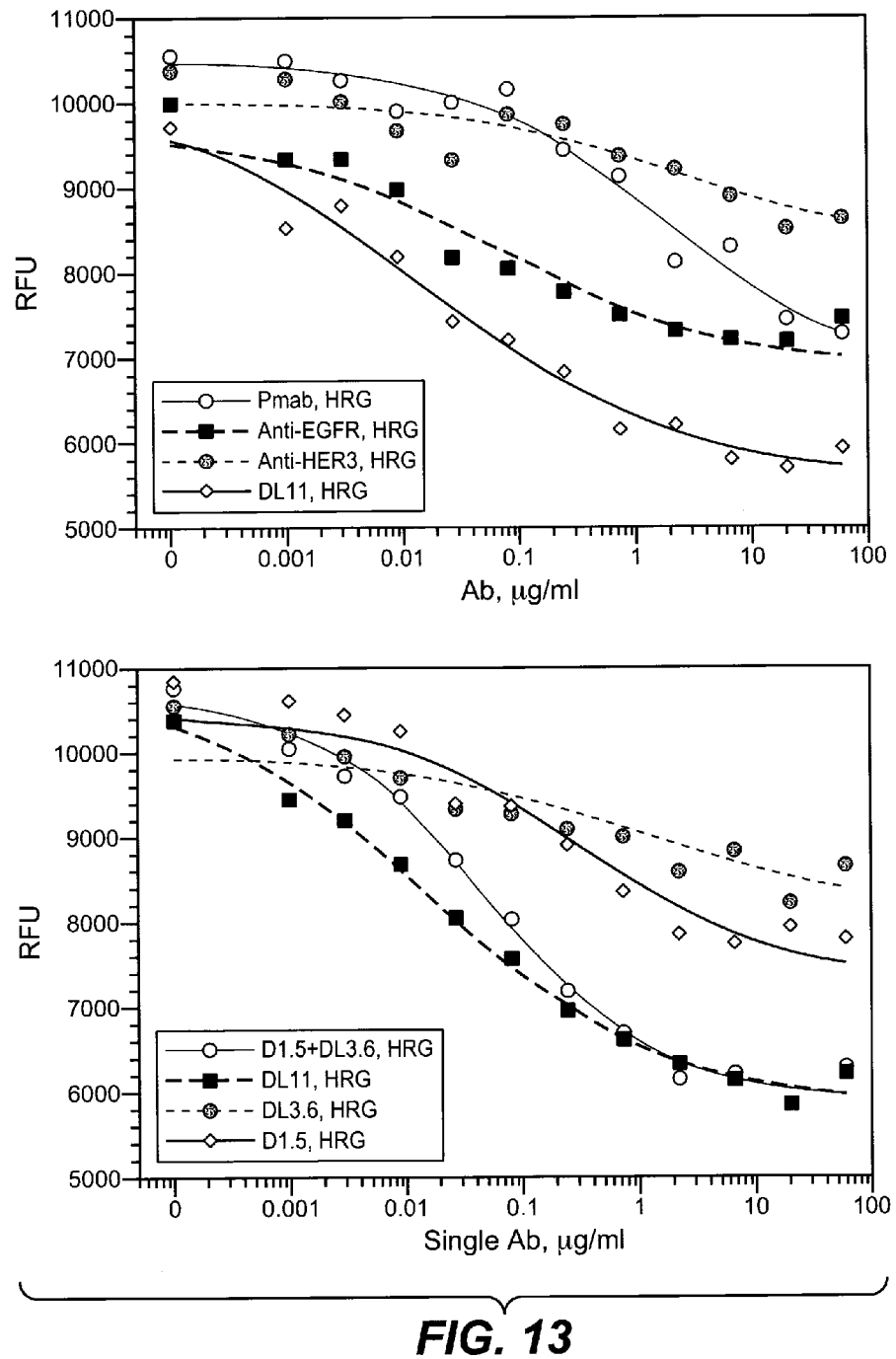
FIG. 13 shows inhibition of the proliferation of Calu-3 cells, a NSCLC line that overexpresses HER2 and has normal levels of HER3 and EGFR. Cell growth was stimulated with HRG and antibodies were tested in a dose dependent manner.

Inhibition of Calu-3 growth by DL11 as compared to an anti-EGFR antibody, pertuzumab, and an anti-HER3 antibody was investigated The NSCLC cell line Calu-3 (ATCC HTB-55, Manassas, Va.) over-expresses HER2 and has normal levels of HER3 and EGFR. Cell growth (10,000 cells/well) was stimulated with HRG (3 nM) in the presence of 1% serum, and antibodies were tested in a dose dependent manner. As shown in FIG. 13, DL11 showed superior activity compared to the monospecific antibodies.

Example 8

Mutagenesis Mapping Study of D1.5-201 and D1.5-201-2, Anti-hEGFR/HER2 Bi-specific Antibodies For affinity maturation of D1.5-201, a light chain soft/homolog library was designed on selected amino acids. Some soft residues were soft randomized, where wild-type residue frequency was 50%. Some residues were randomized using codons encoding for wild-type residue or homolog residue. Some homolog randomization allows 1 or 2 extra residues besides wild-type and homolog. Finally, some residues were unchanged.

Figure 14:
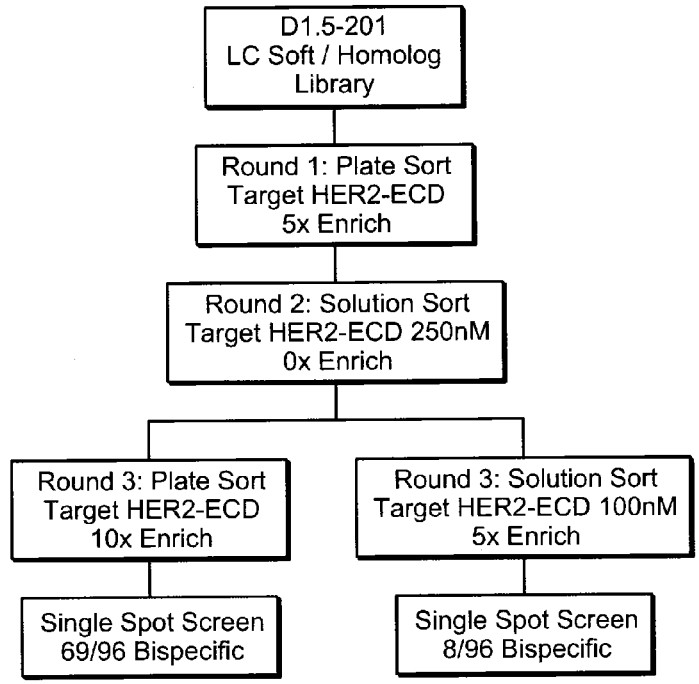
FIG. 14 outlines a sorting strategy for the affinity maturation of D1.5-201.

FIG. 14 illustrates another sorting strategy for the affinity maturation of D1.5-201. In this strategy, D1.5-201 light chain soft/homolog library was sorted as previously described. After three rounds of alternating plate/solution sorting was performed on HER2/ECD under increasing stringency, single clones were picked and assessed in a single spot ELISA to isolate clones that retained dual binding activity for EGFR and HER2. Among the clones assessed, 77/192 show binding for both EGFR and HER2.

The sequences of light chain variable region for the selected affinity matured EGFR/HER2 bispecific antibodies were determined (D1.5-201 (SEQ ID NO: 36, D1.5-201-2 (SEQ ID NO: 37, D1.5-201-3 SEQ ID NO: 38). Phage IC50 were calculated for two selected affinity matured bispecific antibodies (D1.5-201-2, D1.5-201-3) as previously described and compared to D1.5-201 parent clone. Both affinity matured bispecific antibodies show increased affinity for HER2-ECD and EGFR-ECD.

Example 9

DL11 Affinity Maturation

DL11 was further affinity matured as described above resulting in two additional bispecific antibodies with specificity for EGFR and HER3 (DL11b and DL11f) and two antibodies specific for HER3 (DL3-11fb and DL3-11f). The heavy chain and light chain amino acid sequence of DL11b are shown in SEQ ID NOs: 12 and 13, respectively. The heavy chain and light chain amino acid sequence of DL11f are shown in SEQ ID NOs: 14 and 13, respectively. The heavy chain and light chain amino acid sequence of DL3-11b are shown in SEQ ID NOs: 19 and 13, respectively and the heavy chain and light chain amino acid sequence of DL3-11f are shown in SEQ ID NOs: 20 and 13, respectively.

Biacore Affinity Assay

The binding affinities for DL11b and DL11f their EGFR and HER3 targets were determined in the following Biocore assay. Both DL11b and DL11f showed improved affinity for their targets as compared to DL11.

Measurements were done using surface plasmon resonance on a BIAcore™ 2000 instrument (GE Healthcare, BIAcore Life Sciences, Piscataway, N.J.). cDNAs encoding the extracellular domains (ECDs) of human EGFR (amino acids 1-637) and human HER3 (amino acids 1-640) were cloned into a mammalian expression vector containing sequences encoding the Fc region of human IgG1 to generate human Fc fusion protein. Recombinant human EGFR-IgG1 (2.65 mg/ml), human HER3-IgG1 (3.35 mg/ml) were produced by transiently transfecting Chinese hamster ovary cells and were purified via protein A affinity chromatography. cDNA encoding the extracellular domain of human EGFR (amino acids 1-637) was cloned into a mammalian expression vector containing a N-terminal flag sequence.

The binding affinities for DL11f as both a Fab and IgG antibody were determined. For the Fab assay, the DL11f Fab was the analyte and was flowed over a CM5 chip where the different ligands—human EGFR-Fc and human HER3-Fc—were first captured using the BIAcore human Antibody Capture Kit (BR-1008-39, Lot 10020611). A 2-fold dilution series of DL11f Fab was injected in a range of 0.244-250 nM in PBS, 0.05% Tween20 at a flow rate of 30 µl/minute at 25° C. Between each injection of Fc fusion ligands and analyte, 3M Magnesium chloride was used to regenerate the sensor chip (5 µl at a flow rate of 10 µl/mn). To determine the affinity constants of DL11f Fab to human EGFR and human HER3 Fc fusion proteins, the signal from the reference cell was subtracted from the observed test sensorgram. Kinetic constants were calculated by non-linear regression fitting of the data according to a 1:1 Langmuir binding model using BIAcore evaluation software (GE Healthcare), version 4.1, supplied by the manufacturer. Two replicates of a representative concentration of DL11f Fab (125 nM) gave very similar fitting and kinetics constants for all Fc fusions proteins. DL11f Fab bound to human EGFR-Fc with a KD value of 1.92 nM and to human HER3-Fc with a KD value of 0.39 nM.

A second experimental condition was explored to obtain binding kinetics from DL11f as IgG. Here, DL11f human IgG1 was immobilized on the sensor chip CM5, and monomeric human EGFR-ecd and human HER3-ecd were used as the analyte. A 2-fold dilution series of human EGFR-ecd and human HER3-ecd was injected in a range of 0.244-250 nM in PBS, 0.05% Tween20 at a flow rate of 30 µl/minute at 25° C. Binding kinetics were determined as for the Fab. DL11f bound to human EGFR-ecd, and human HER3-Fc with $K_D$ values of 19.9 nM and 2.63 nM respectively. In both experiments, we observed that DL11f antibody has a consistent 5-8 fold higher affinity for HER3 than for EGFR. The weaker affinities found in experiment 2 for both receptors when compared to experiment 1 could be due to a difference between having EGFR ecd or HER3 ecd as analytes in solution and the receptor as Fc fusion immobilized on the flow cell chip. It is possible that these multi-domain receptors as free ECD may encounter more entropic penalty for binding energy when in solution thus resulting in weaker affinity.

DL11b showed similar binding affinities for EGFR and HER3 as DL11f under similar conditions in a separate Biacore analysis.

DL3-11b and DL3-11f lost the ability to specifically bind to EGFR while retaining the ability to specifically bind to HER3.

Inhibition of MDA-175 Cell Proliferation

Figure 15:
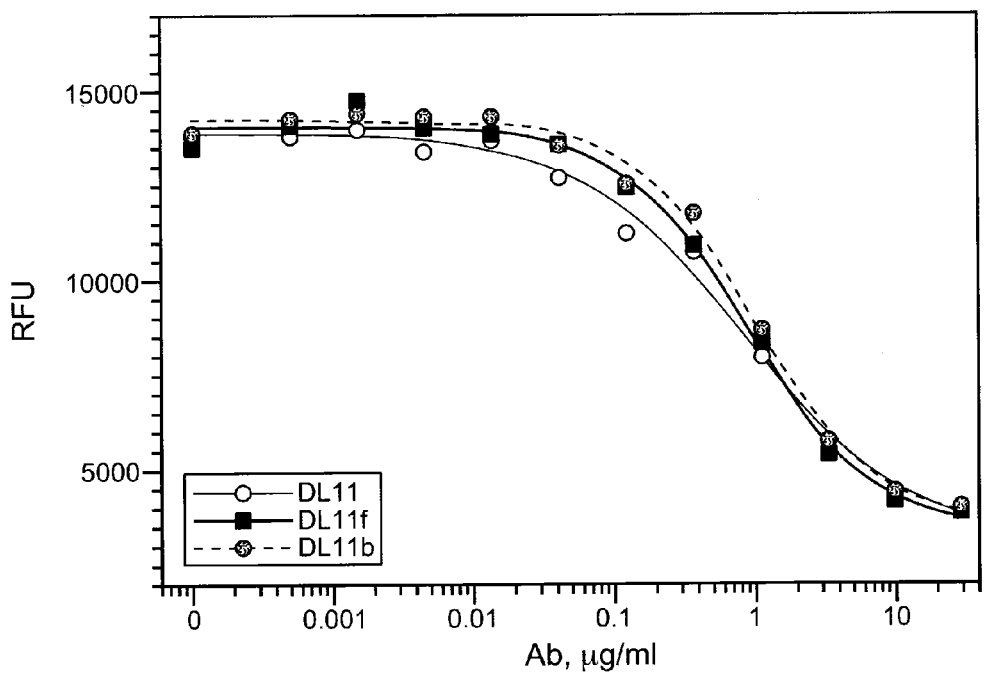
FIG. 15 shows inhibition of MDA-175 cell proliferation by DL11, DL11b and DL11f.

Inhibition of MDA-175 cell proliferation by DL11b and DL11f was investigated as described above. Both DL11b and DL11f inhibited proliferation of MDA-175 cells to a similar degree as the DL11 antibody. FIG. 15. The IC50s of DL11, DL11f, and DL11b were all around 0.8-1.0 ug/ml.

Inhibition of Heregulin Induced HER3 Phosphorylation in MCF7 Cells.

Figure 16:
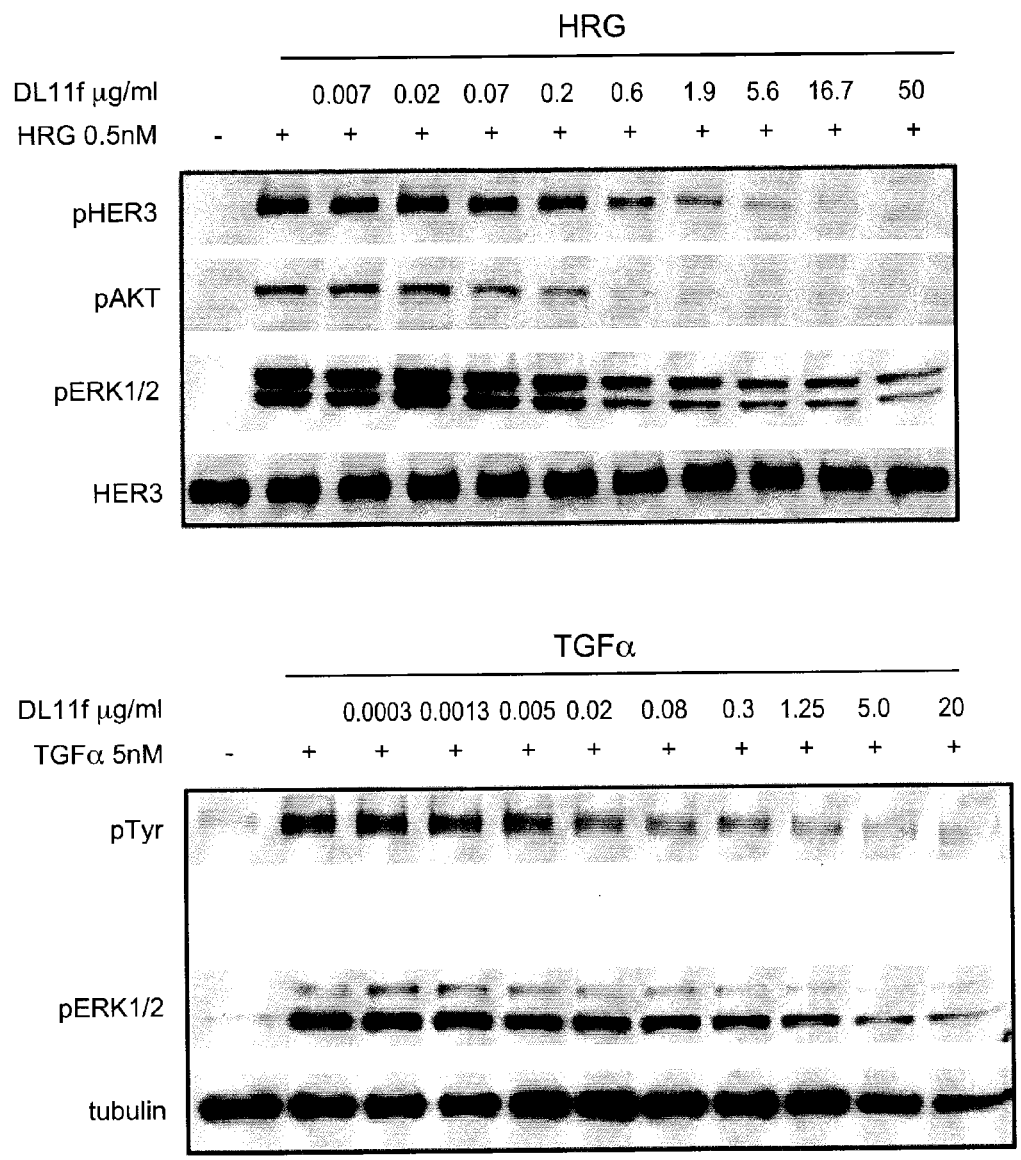
FIG. 16 shows that DL11f inhibits heregulin-induced HER3 phosphorylation and TGFα-induced EGFR phosphorylation.

To determine whether DL11f could inhibit heregulin induced HER3 phosphorylation in MCF7 cells, a receptor phosphorylation assay was performed as described Example 6. The results demonstrate that DL11f inhibited heregulin induced HER3 phosphorylation in a dose dependent manner. FIG. 16.

Inhibition of TGF-α Induced EGFR Phosphorylation in Stably Transfected EGFR-NR6 Cells To determine if DL11f selectively blocks TGF-α induced EGFR phosphorylation, a receptor phosphorylation assay was performed as described in Example 2. The data in FIG. 16 demonstrate that DL11f inhibits TGF-α induced EGFR phosphorylation in a dose dependent manner in this cell based assay.

DL11 and DL11f Inhibit Tumor Growth in an in vivo Model

A HCA-7 tumor transplant model assay was used to determine the effect of DL11 and DL11f on in vivo tumor growth. The assay was performed as follows.

SCID beige mice (Charles River Laboratories, San Diego, Calif. were transplanted subcutaneously with HCA-7 tumor pieces. When tumors reached a mean volume of 100 to 250 mm3, mice with similarly sized tumors were randomized into treatment cohorts (n=9/group) as follows: Vehicle (PBS), Pertuzumab (10 mg/kg), D1.5 (25 mg/kg), D1.5+DL3.6 (25 mg/kg each), DL11 (25 mg/kg), or DL11f (25 mg/kg). Treatments were administered intraperitoneally, beginning with a 2× loading dose (20 or 50 mg/kg) on the day of randomization and continuing weekly for a total of three treatments. Tumors were measured with calipers twice a week for the duration of the study. Mice were housed in standard rodent microisolator cages. Environmental controls for the animal rooms were set to maintain a temperature of approximately 70° F., a relative humidity of approximately 40%-60%, and an approximate 14-hour light/10-hour dark cycle. Mice were maintained according to the ILAR Guide for the Care and Use of Laboratory Animals, and the study was reviewed and approved by the Institutional Animal Care and Use Committee (IACUC) at Genentech.

Figure 17:
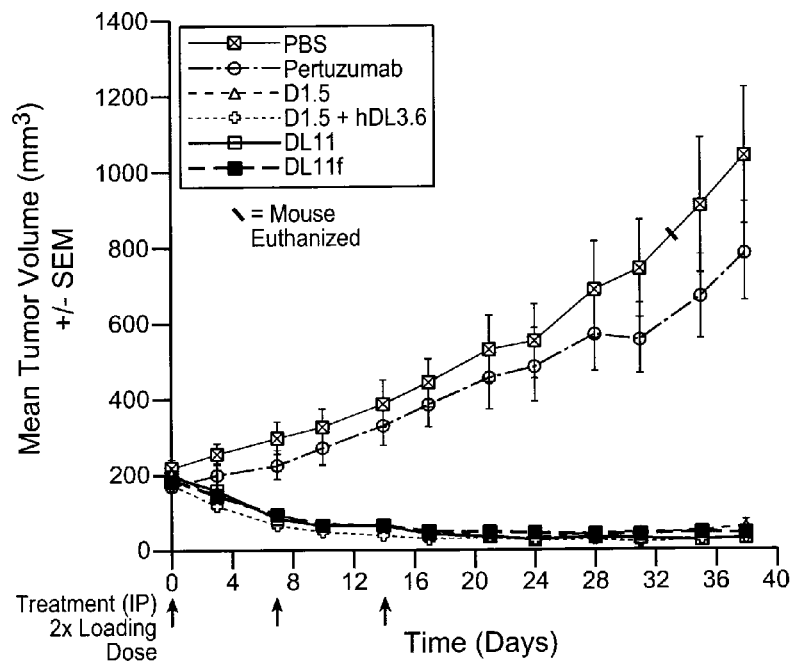
FIG. 17 is a graph showing inhibition of tumor growth in an HCA-7 tumor transplant model by DL11 and DL11f.

DL11 and DL11f were equally effective in reducing mean tumor volume in this xenograft model. FIG. 17.

DL11f is Active in a Non-small Lung Cell Cancer Model

The antibodies were tested in mice with established tumors derived from the human NSCLC line H358 (ATCC CRL-5807, Manassas, Va.). $5 \times 10^6$ H358 cells were inoculated subcutaneously with matrigel in CB17 SCID mice. Animals with similarly sized tumors were randomized into treatment cohorts (n=9/group) as follows: Vehicle (DL11f formulation buffer), D1.5 (25 mg/kg), DL3.11b (25 mg/kg), DL11f (30 mg/kg), or D1.5+DL3.11b (25 mg/kg each). Treatments were administered intraperitoneally, beginning with a 2× loading dose (50 or 60 mg/kg) on the day of randomization and continuing weekly for a total of four treatments. Tumors were measured with calipers twice a week for the duration of the study.

Figure 18:
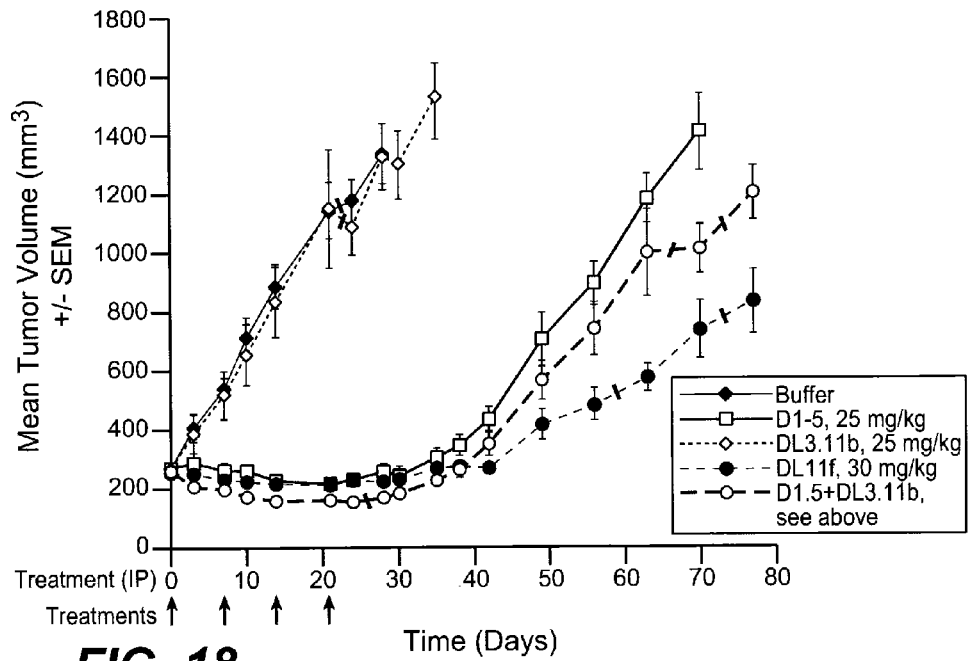
FIG. 18 is a graph showing inhibition of tumor growth in an H358 NSCLC xenograft model by DL11f.

As shown in FIG. 18, the bispecific antibody DL11f is active in this NSCLC model and is more effective in inhibiting tumor growth than a combination of an anti-EGFR specific and an anti-HER3 specific antibody (D1.5+DL3.11b).

Example 10

DL3.6 Affinity Maturation

DL3.6 was further affinity matured as described above resulting in additional anti-HER3 antibodies. DL3.6b exhibited an increase in affinity for its target as compared to parent antibody DL3.6. The heavy and light chain amino acid sequences of DL3.6b are shown in SEQ ID NOs: 17 and 13, respectively.

Figure 19:
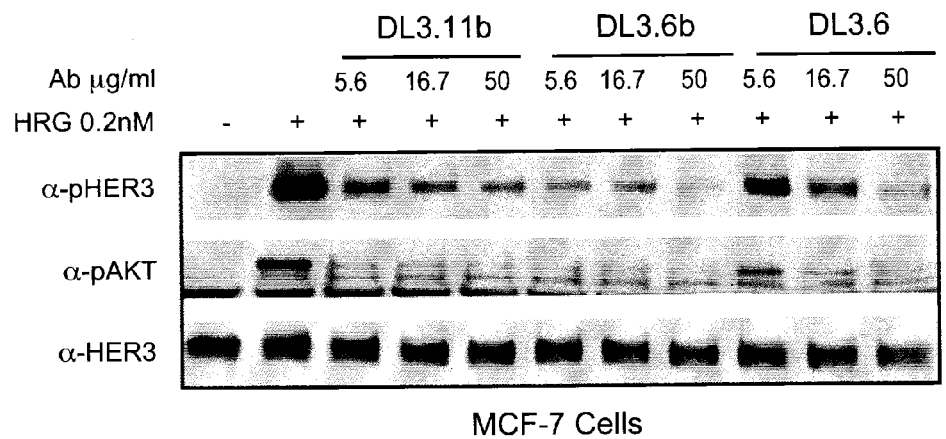
FIG. 19 shows inhibition of HRG induced HER3 phosphorylation by DL3-11b, DL3.6b and DL3.6.
Figure 20:
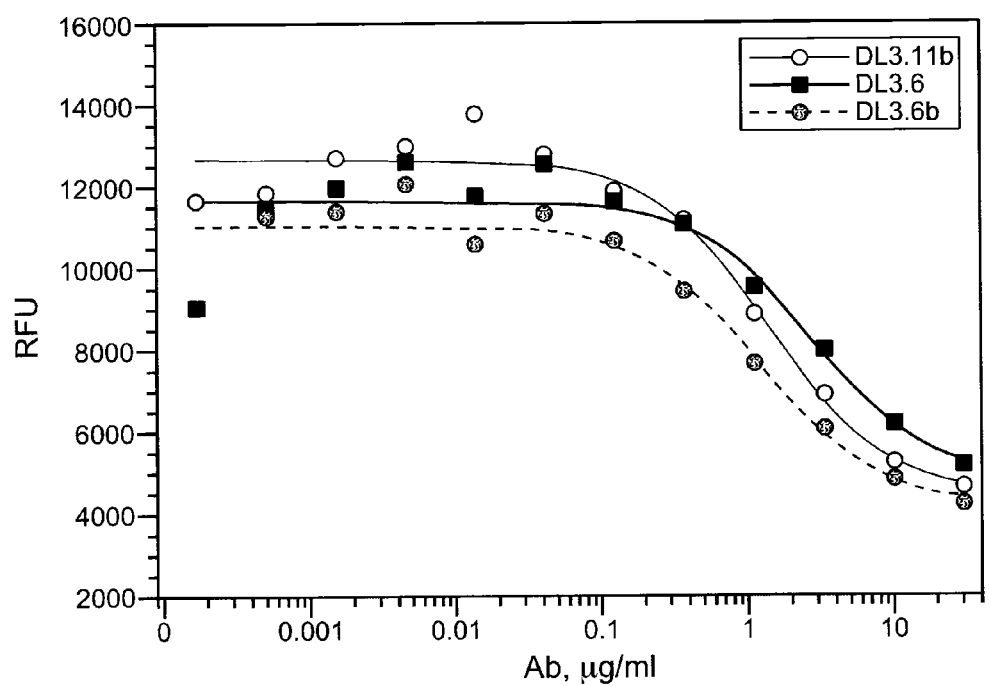
FIG. 20: Inhibition of MDA-175 cell proliferation by DL3-11b, DL3.6b and DL3.6

As shown in FIGS. 19 and 20, DL3-11b, DL3.6, and DL3.6 b inhibited HRG induced HER3 phosphorylation and MDA-175 cell proliferation. Assays were performed as described above.

Example 11

In vivo Activity in Fadu Xenograft Model, a Head and Neck Squamous Cell Carcinoma Model DL11f, a commercially available anti-EGFR antibody, and an anti-HER3 antibody were tested in mice with established tumors derived from Fadu cells (ATCC HTB-43, Manassas, Va.) $5 \times 10^6$ FaDu cells were inoculated subcutaneously in CB 17 SCID mice. Animals with similarly sized tumors were randomized into treatment cohorts (n=9/group) as follows: Vehicle (DL11f formulation buffer), anti-EGFR antibody (25 mg/kg), anti-HER3 antibody (50 mg/kg), and DL11f (25 mg/kg). Treatments were administered intraperitoneally, beginning with a 2× loading dose (50 or 100 mg/kg respectively) on the day of randomization and continuing weekly for a total of four treatments. Tumors were measured with calipers twice a week for the duration of the study.

Figure 21:
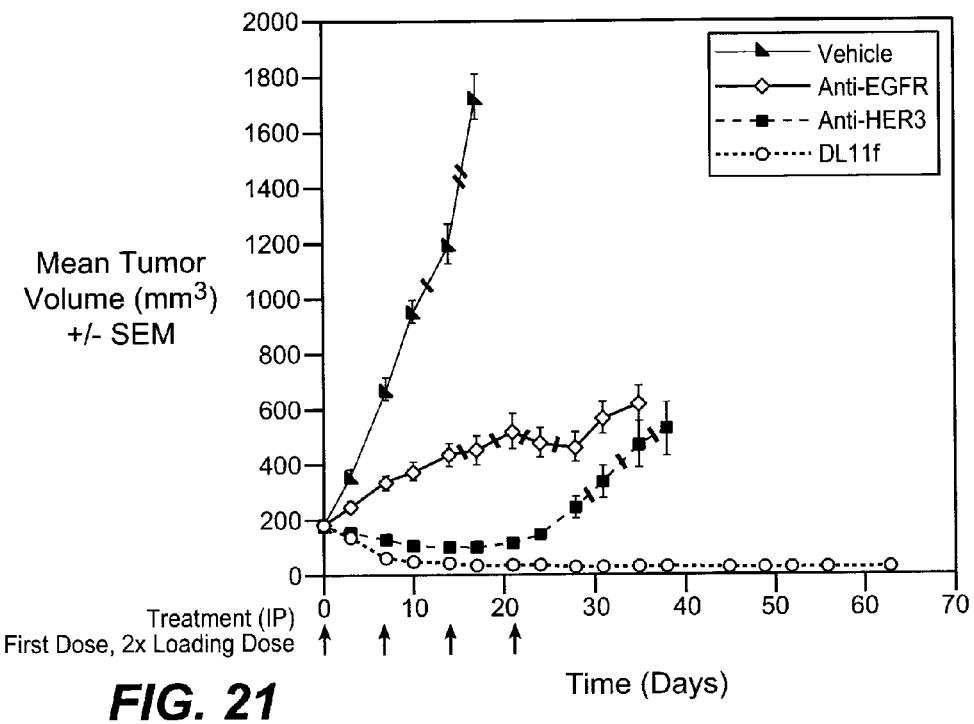
FIG. 21 is a graph showing inhibition of tumor growth in FaDu cancer model by DL11f.

As shown in FIG. 21, DL11f is active in the FaDu head and neck cancer model and is more effective in inhibiting tumor growth than either an anti-EGFR specific or an anti-HER3 specific antibody.

Example 12

In vivo Activity in BxPC3 Xenograft Model, a HER3 Driven Pancreatic Model

DL11f, an anti-EGFR antibody, pertuzumab, and an anti-HER3 antibody were tested in mice with established tumors derived from the pancreatic cell line BxPC3 (ATCC CRL-1687, Manassas, Va.). $10 \times 10^6$ BxPC3 cells were inoculated subcutaneously in CB17 SCID mice. Animals with similarly sized tumors were randomized into treatment cohorts (n=8/group) as follows: Vehicle (DL11f formulation buffer), anti-EGFR antibody (25 mg/kg), pertuzumab (25 mg/kg), anti-HER3 antibody (50 mg/kg), and DL11f (25 mg/kg), Treatments were administered intraperitoneally, beginning with a 2× loading dose (50 or 100 mg/kg) on the day of randomization and continuing weekly for a total of four treatments. Tumors were measured with calipers twice a week for the duration of the study.

Figure 22:
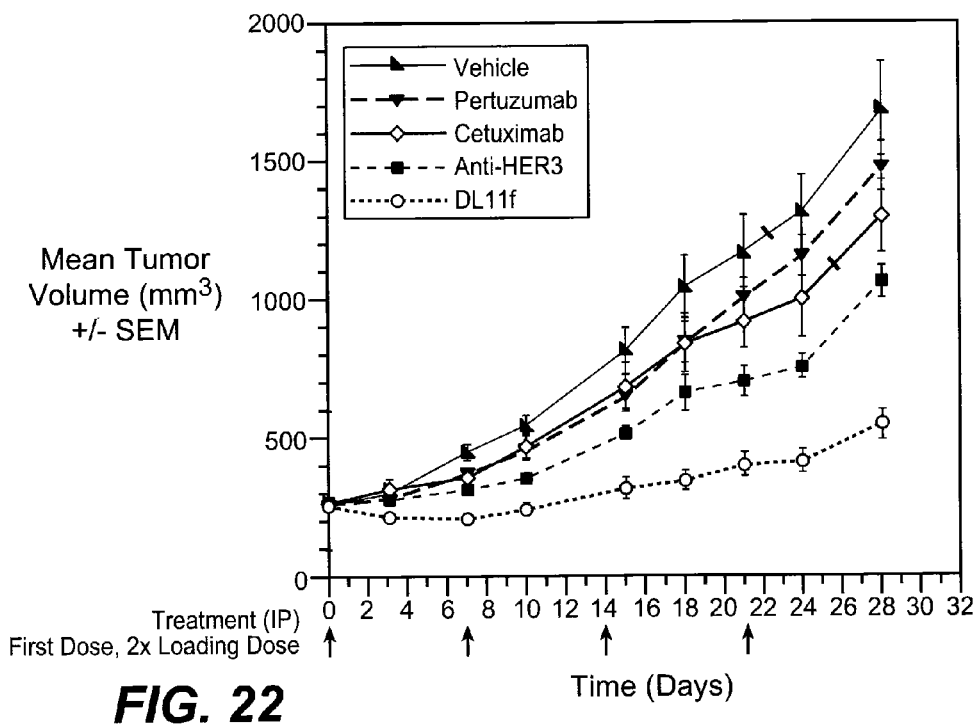
FIG. 22 is a graph showing inhibition of tumor growth in BxPC3 pancreatic cancer model by DL11f.

DL11f is active in the BxPC3 pancreatic cancer model and is more effective in delaying tumor growth than either an anti-EGFR specific or an anti-HER3 specific antibody. (FIG. 22.)

Example 13

In vivo Activity in NSCLC Calu-3 Xenograft Model

DL11f, a commercially available anti-EGFR antibody, and an anti-HER3 antibody were tested in mice with established tumors derived from the NSCLC line Calu-3 (ATCC HTB-55, Manassas, Va.). $5 \times 10^6$ Calu-3 cells were inoculated subcutaneously in SCID Beige mice. Animals with similarly sized tumors were randomized into treatment cohorts (n=9/group) as follows: Vehicle (DL11f formulation buffer), anti-EGFR antibody (25 mg/kg), anti-HER3 antibody (25 mg/kg), and DL11f (25 mg/kg), Treatments were administered intraperitoneally, beginning with a 2× loading dose (50) on the day of randomization and continuing weekly (anti-HER3 biweekly) for a total of four (eight) treatments. Tumors were measured with calipers twice a week for the duration of the study.

Figure 23:
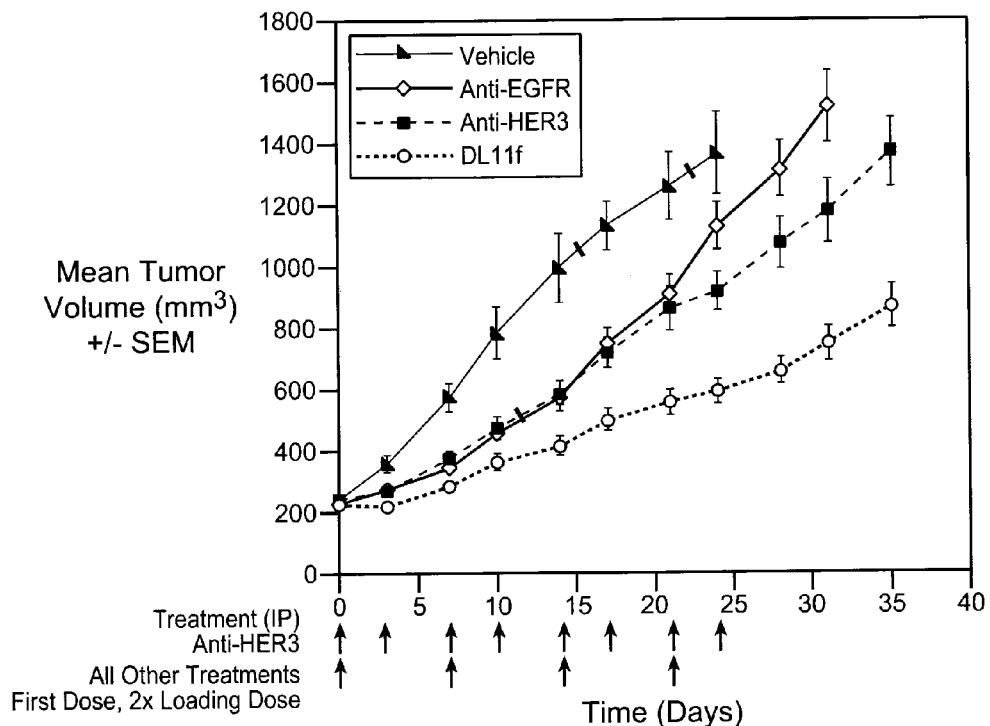
FIG. 23 is a graph showing inhibition of tumor growth in Calu-3 non-small cell lung cancer model by DL11f.

DL11f is active in the Calu-3 non-small cell lung cancer model and is more effective in delaying tumor growth than either an anti-EGFR specific or an anti-HER3 specific antibody. (FIG. 23.)

Example 14

In vivo Activity in Epidermal A431 Xenograft Model

DL11f, a commercially available anti-EGFR antibody, and an anti-HER3 antibody were tested in mice with established tumors derived from the epidermoid cell line A431 (ATCC CRL-2592, Manassas, Va.). $5 \times 10^6$ A431 cells were inoculated subcutaneously in SCID Beige mice. Animals with similarly sized tumors were randomized into treatment cohorts (n=8/group) as follows: Vehicle (DL11f formulation buffer), an anti-EGFR antibody (12.5 mg/kg), anti-HER3 (50 mg/kg), and DL11f (12.5 and 25 mg/kg), Treatments were administered once intraperitoneally on the day of randomization. Tumors were measured with calipers twice a week for the duration of the study.

Figure 24:
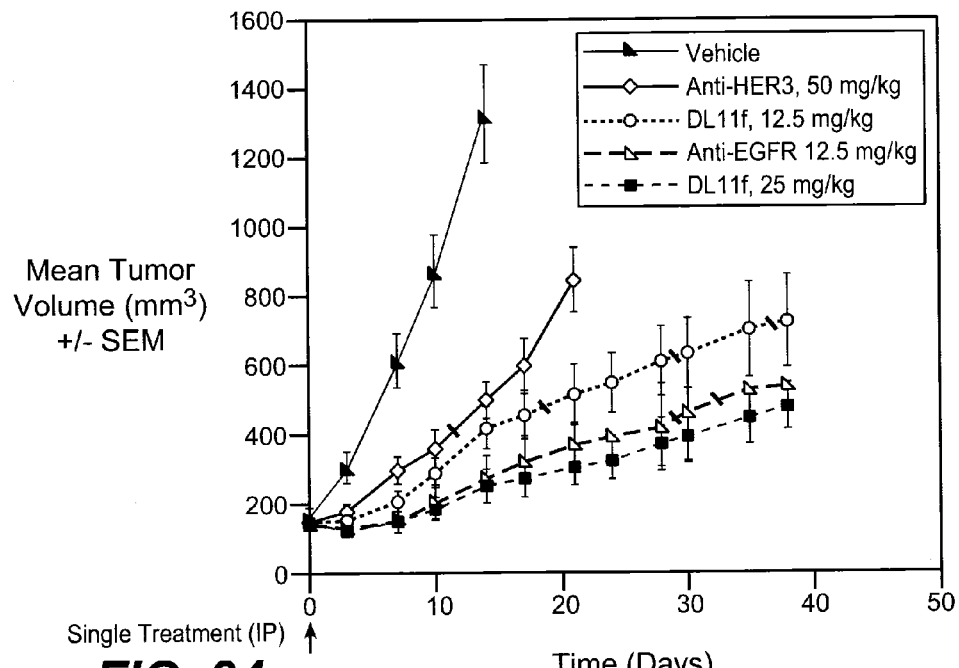
FIG. 24 is a graph showing inhibition of tumor growth in A431 epidermal cancer model by DL11f.

Due to the faster clearance of DL11f compared to the anti-EGFR antibody in mice, DL11f was dosed at 2× concentration compared to the anti-EGFR antibody in order to achieve comparable exposure levels. Taken together, DL11f inhibits tumor growth in the A431 epidermal cancer model as well as the anti-EGFR antibody. (FIG. 24.)

Example 15

In vivo Activity in Nude Mice Bearing Xenografts of the Patient-derived Breast Cancer MAXF449

DL11f, a commercially available anti-EGFR antibody, and an anti-HER3 antibody were tested at Oncotest GmbH, Freiburg, Germany. Oncotest passages patient tumors, like the mammary cancer MAXF 449, as subcutaneous xenografts in nude mice, following direct transplantation of tumors from donor patients. According to Oncotest's protocols, animals with similarly sized tumors were randomized into treatment cohorts (n=10/group) as follows: DL11f (30 mg), anti-EGFR antibody (30 mg/kg), anti-HER3 (60 mg/kg) and Vehicle (DL11f formulation buffer). Treatments were administered intraperitoneally, beginning with a 2× loading dose (60 or 120 mg/kg respectively) on the day of randomization and continuing weekly for a total of four treatments.

Figure 25:
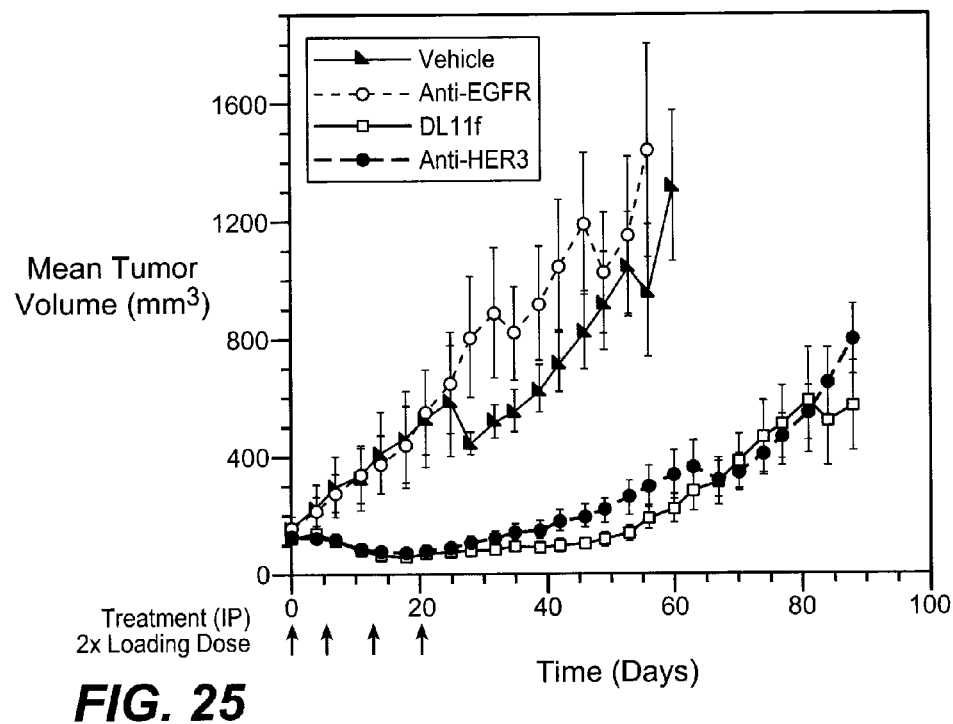
FIG. 25 is a graph showing inhibition of tumor growth in MAXF44 breast cancer model by DL11f.

DL11f and anti-HER3 inhibits tumor growth in the MAXF44 breast cancer model whereas the anti-EGFR antibody has no effect (FIG. 25).

Example 16

In vivo Activity in Prostate DU145 XenoGraft Model

Figure 26:
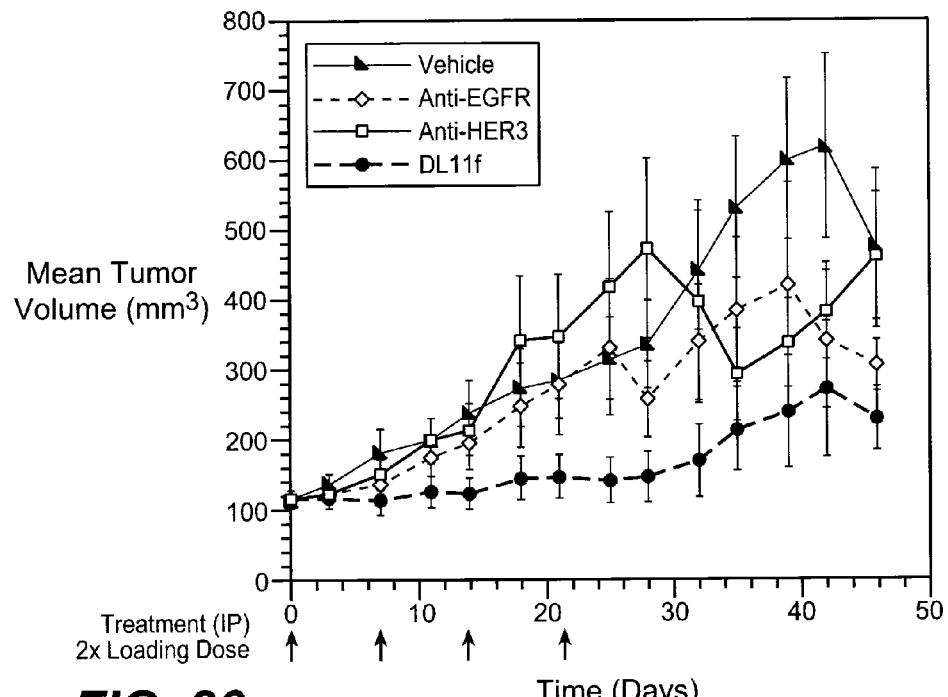
FIG. 26 is a graph showing inhibition of tumor growth in DU145 prostate cancer model by DL11f.

DL11f, a commercially available anti-EGFR antibody, and an anti-HER3 antibody were tested at Piedmont Research Center, Morrisville according to Piedmont's protocols. Animals with similarly sized tumors were randomized into treatment cohorts (n=10/group) as follows: DL11f (25 mg), anti-EGFR antibody (25 mg/kg), anti-HER3 (50 mg/kg) and Vehicle (DL11f formulation buffer). Treatments were administered intraperitoneally, beginning with a 2× loading dose (50 or 100 mg/kg respectively) on the day of randomization and continuing weekly for a total of four treatments. DL11f is active in DU145 prostate cancer model and is more effective in inhibiting tumor growth than either an anti-EGFR specific or an anti-HER3 specific antibody. (FIG. 26.)

Example 17

In vivo Activity in Nude Mice Bearing Xenografts of the Patient-derived Ovarian Cancer OVXF550

DL11f, a commercially available anti-EGFR antibody, and an anti-HER3 antibody were tested at Oncotest GmbH, Freiburg, Germany. Oncotest passages patient tumors, like the ovarian cancer OVXF550, as subcutaneous xenografts in nude mice, following direct transplantation of tumors from donor patients. According to Oncotest's protocols animals with similarly sized tumors were randomized into treatment cohorts (n=10/group) as follows: DL11f (30 mg), anti-EGFR antibody (30 mg/kg), anti-HER3 antibody (60 mg/kg) and Vehicle (DL11f formulation buffer). Treatments were administered intraperitoneally, beginning with a 2× loading dose (60 or 120 mg/kg respectively) on the day of randomization and continuing weekly for a total of five treatments.

Figure 27:
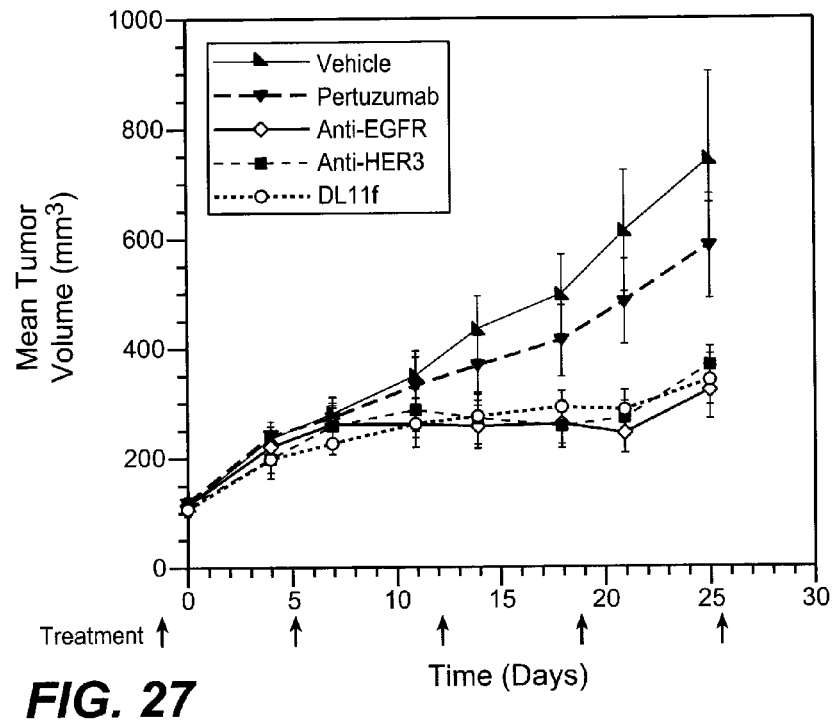
FIG. 27 is a graph showing inhibition of tumor growth in OVXF550 ovarian cancer model by DL11f.

DL11f is active in the OVFX550 ovarian cancer model. (FIG. 27.)

Example 18

Figure 28:
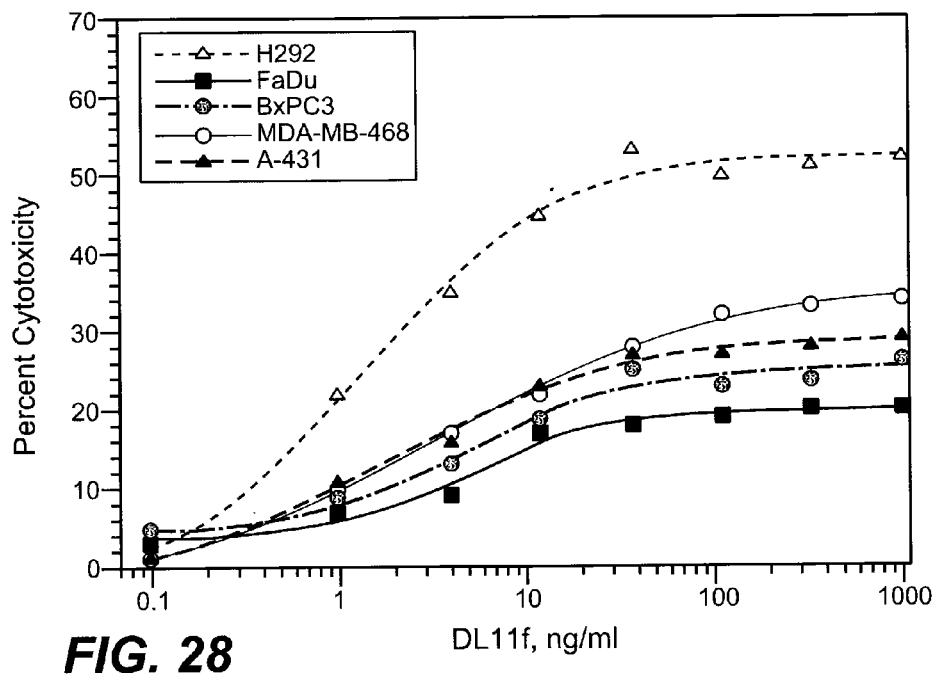
FIG. 28 shows that DL1 if induces ADCC in several cell lines.

DL11f Mediates Antibody Dependent Cellular Cytotoxicity (ADCC) in vitro and in vivo DL11f mediates ADCC in vitro. A431, H292 (ATCC CRL-1848, Manassas, Va.), FaDu, BxPC3 and MDA 468 (ATCC HTB-132, Manassas, Va.) cells (all from ATCC) were plated in 96 well plates in the presence of indicated concentrations of antibodies. After pre-incubation for 30 minutes at 37° C. isolated peripheral blood mononuclear cells (PBMC) were added and the incubation continued for 4 more hours at 37° C. After 4 hours, the plates were centrifuged and the supernatants were harvested. The LDH activity in the supernatants was determined according to the Promega CytoTox-One homogeneous membrane integrity assay procedure. To determine the percentage cell mediated cytotoxicity the average absorbance were calculated and the background was subtracted. As shown in FIG. 28, DL11f mitigates ADCC in EGFR expressing cell lines in a dose dependent manner.

Figure 29:
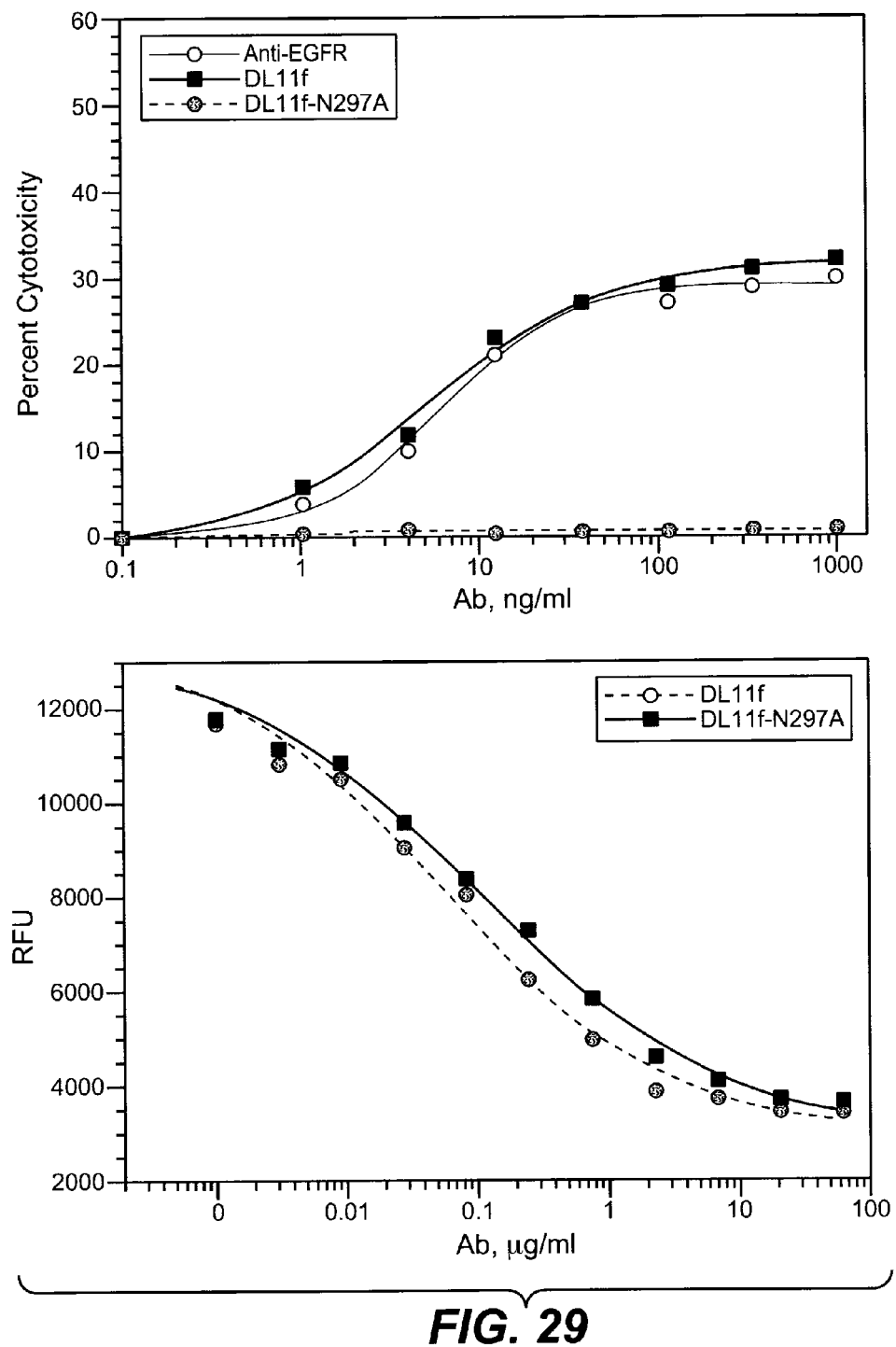
FIG. 29 shows that DL11f-N297A lacks ADCC activity.

An amino acid substitution of N297A was introduced into DL11f to delete the effector function. N297 is required for FcRγ and/or complement binding. DL11f-N297A exhibits a lack of ADCC in vitro. As expected, the growth inhibitory function of DL11f in vitro is not affected by the mutation. (FIG. 29.)

Figure 30:
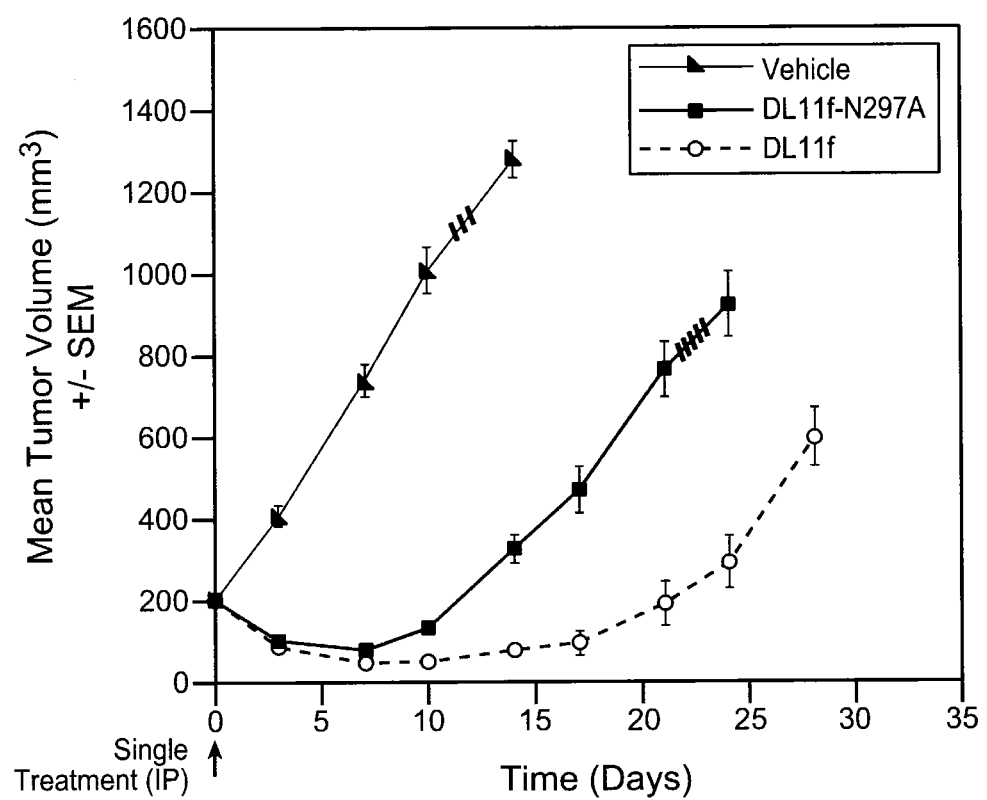
FIG. 30 shows inhibition of tumor growth in H292 NSCLC cancer model by DL11f and DL11f-N297A.

DL11f and DL11f-N297A were tested in mice with established tumors derived from the NSCLC cell line H292 (ATCC CRL-1848, Manassas, Va.). $5 \times 10^6$ A431 cells were inoculated subcutaneously in C.B17-SCID mice. Animals with similarly sized tumors were randomized into treatment cohorts (n=10/group) as follows: Vehicle (DL11f formulation buffer), DL11f (6 mg/kg) and DL11f-N297A (6 mg/kg). Treatments were administered once intraperitoneally on the day of randomization. Tumors were measured with calipers twice a week for the duration of the study. Initially, DL11f and DL11f N297A inhibited tumor growth equivalently by inhibiting HER pathway signaling. But as doses diminished DL11f exhibited prolonged anti-tumor activity compared to DL11f N297A due to its ADCC capability. (FIG. 30.)

Example 19

DL11f is Less Toxic than Cetuximab in Cynomolgus Monkeys

A study was conducted to determine the relative toxicity of DL11f and cetuximab. Cynomolgus monkeys were assigned into three Groups and dosed with either DL11f or cetuximab (Capital Wholesale Drug, Columbus, Ohio) once weekly for six weeks as follows:

Group 1: Cetuximab 25 mg/kg;
Group 2: DL11f 25 mg/kg;
Group 3: DL11f 12.5 mg/kg.

All 3 cetuximab dosed animals developed skin lesions between the 3rd and 4th dose, indicating toxicity. This result was expected based on prior Cynomolgus studies conducted during FDA approval of cetuximab. None of the DL11f dosed animals showed signs of toxicity at this point in the study.

One of the animals receiving the 25 mg/kg dose of DL11f developed a skin lesion one week following the 6th dose. This lesion measured approximately 4 cm×7 cm and was very mild and limited to a smaller area when compared to lesions observed in the cetuximab treated animals.

Based on the analysis of toxicokinetic parameters in this toxicology study, exposure of cetuximab and DL11f were similar in the animals dosed at 25 mg/kg of each test compound.

A second, larger scale study was performed under the following conditions.

Cynomolgus monkeys were assigned into six Groups and dosed, by intravenous administration, with either DL11f or a vehicle control once weekly for twelve weeks as follows:

| Group 1: | 10 monkeys (5 male/5 female) - | Vehicle Control |
|---|---|---|
| Group 2: | 10 monkeys (5 male/5 female) | DL11f 5 mg/kg |

| Group 3: | 10 monkeys (5 male/5 female) | DL11f 15 mg/kg |
| Group 4: | 10 monkeys (5 male/5 female) | DL11f 30 mg/kg |
| Group 5: | 4 monkeys (2 male/2 female) | Vehicle Control |
| Group 6: | 4 monkeys (2 male/2 female) | DL11f 30 mg/kg |

None of the animals exhibited any apparent skin toxicities during the study or during the recovery period following the final dosing with the DL11f.

A single dose, IV administration PK study was also conducted in cynomolgus monkeys. In this study, 3 monkeys per group were dosed intravenously with 1, 10, or 30 mg/kg of DL11f. The PK over the dose range explored were non-linear, consistent with a saturable clearance as has been seen with other EGFR-targeting antibodies.

All patents, patent applications, patent application publications, and other publications cited or referred to in this specification are herein incorporated by reference in their entirety to the same extent as if each independent patent, patent application, patent application publication or publication was specifically and individually indicated to be incorporated by reference.

The invention claimed is:

1. A method of treating an individual having cancer comprising administering to the individual an effective amount of a multispecific antibody comprising an antigen-binding domain that specifically binds to EGFR and HER3, wherein the antibody comprises (a) HVR-H1 comprising the amino acid sequence of LSGDWIH (SEQ ID NO: 48); (b) HVR-H2 comprising the amino acid sequence of VGEISAAGGYTD (SEQ ID NO: 51); and (c) HVR-H3 comprising the amino acid sequence of ARESRVSFEAAMDY (SEQ ID NO: 53); and (d) HVR-L1 comprising the amino acid sequence of NIATDVA (SEQ ID NO: 55); (e) HVR-L2 comprising the amino acid sequence of SASF (SEQ ID NO: 56); and (f) HVR-L3 comprising the amino acid sequence of SEPEPYT (SEQ ID NO: 57), and wherein the cancer comprises cells that express EGFR and HER3.

2. The antibody of claim 1, wherein the cancer is selected from the group consisting of breast cancer, colorectal cancer, pancreatic cancer, head and neck cancer, melanoma, ovarian cancer, prostate cancer, and non-small lung cell cancer.

3. The method of claim 1, wherein the antibody comprises (a) a heavy chain variable domain having at least 95% sequence identity to the amino acid sequence of SEQ ID NO: 30; (b) a light chain variable domain having at least 95% sequence identity to the amino acid sequence of SEQ ID NO: 29; or (c) a heavy chain variable domain as in (a) and a light chain variable domain as in (b).

4. The method of claim 1, wherein the antibody comprises a heavy chain variable domain comprising SEQ ID NO: 30.

5. The method of claim 1, wherein the antibody comprises a light chain variable domain sequence comprising SEQ ID NO: 29.

6. The method of claim 1, wherein the antibody is a full length IgG1 antibody.

7. The method of claim 6, wherein the antibody exhibits ADCC activity.

8. The method of claim 1, wherein the antibody is conjugated with a cytotoxic agent.

9. A method of treating an individual having cancer comprising administering to the individual an effective amount of a multispecific antibody comprising an antigen-binding domain that specifically binds to EGFR and HER3, wherein the antibody comprises a heavy chain variable domain sequence comprising SEQ ID NO: 30 and a light chain variable domain sequence comprising SEQ ID NO: 29, and wherein the cancer comprises cells that express EGFR and HER3.

10. The method of claim 9, wherein the antibody is a full length IgG1 antibody.

11. The method of claim 10, wherein the antibody exhibits ADCC activity.

12. The method of claim 9, wherein the antibody is conjugated with a cytotoxic agent.

13. The antibody of claim 9, wherein the cancer is selected from the group consisting of breast cancer, colorectal cancer, pancreatic cancer, head and neck cancer, melanoma, ovarian cancer, prostate cancer, and non-small lung cell cancer.

* * * * *

SEQUENCE LISTING

```
<160> NUMBER OF SEQ ID NOS: 79

<210> SEQ ID NO 1
<211> LENGTH: 214
<212> TYPE: PRT
<213> ORGANISM: Artificial Sequence
<220> FEATURE:
<223> OTHER INFORMATION: synthetic

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 228
<212> TYPE: PRT
<213> ORGANISM: Artificial Sequence
<220> FEATURE:
<223> OTHER INFORMATION: synthetic

<400> SEQUENCE: 2
```

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Thr Gly Asn
            20                  25                  30

Trp Ile His Trp Val Arg Gln Ala Pro Gly Lys Gly Leu Glu Trp Val
            35                  40                  45

Gly Glu Ile Ser Pro Ser Gly Gly Tyr Thr Asp Tyr Ala Asp Ser Val
    50                  55                  60

Lys Gly Arg Phe Thr Ile Ser Ala Asp Thr Lys Asn Thr Ala Tyr
65                  70                  75                  80

Leu Gln Met Asn Ser Leu Arg Ala Glu Asp Thr Ala Val Tyr Tyr Cys
            85                  90                  95

Ala Arg Glu Ser Arg Val Ser Tyr Glu Ala Ala Met Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His
225

<210> SEQ ID NO 3
<211> LENGTH: 214
<212> TYPE: PRT
<213> ORGANISM: Artificial Sequence
<220> FEATURE:
<223> OTHER INFORMATION: synthetic

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Thr Pro Tyr
            85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125
```

```
Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 4
<211> LENGTH: 214
<212> TYPE: PRT
<213> ORGANISM: Artificial Sequence
<220> FEATURE:
<223> OTHER INFORMATION: synthetic

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Leu Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 5
<211> LENGTH: 220
<212> TYPE: PRT
<213> ORGANISM: Artificial Sequence
<220> FEATURE:
<223> OTHER INFORMATION: synthetic

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Leu Gly Asp Ser
            20                  25                  30

Glu Asn Gly Tyr Ala Asp Val Ala Trp Tyr Gln Gln Lys Pro Gly Lys
        35                  40                  45

Ala Pro Lys Leu Leu Ile Tyr Glu Gly Ser Ser Leu Tyr Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ala Ala Pro Ser Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 6
<211> LENGTH: 220
<212> TYPE: PRT
<213> ORGANISM: Artificial Sequence
<220> FEATURE:
<223> OTHER INFORMATION: synthetic

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Leu Ala Ser
            20                  25                  30

His Asp Gly Thr Pro Trp Val Ala Trp Tyr Gln Gln Lys Pro Gly Lys
        35                  40                  45

Ala Pro Lys Leu Leu Ile Tyr Asp Ala Ser Tyr Leu Tyr Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Thr Phe Ala Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140
```

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 7
<211> LENGTH: 214
<212> TYPE: PRT
<213> ORGANISM: Artificial Sequence
<220> FEATURE:
<223> OTHER INFORMATION: synthetic

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Phe Pro Asp
            20                  25                  30

Val Ala Trp Tyr Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ala Pro Thr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 8
<211> LENGTH: 214
<212> TYPE: PRT
<213> ORGANISM: Artificial Sequence
<220> FEATURE:
<223> OTHER INFORMATION: synthetic

<400> SEQUENCE: 8

Asp Ile Gln Met Thr Gln Ser Pro Ser Ser Leu Ser Ala Ser Val Gly

```
            1               5                  10                 15
Asp Arg Val Thr Ile Thr Cys Arg Ala Ser Gln Ala Ile Ala Ser Asp
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 9
<211> LENGTH: 214
<212> TYPE: PRT
<213> ORGANISM: Artificial Sequence
<220> FEATURE:
<223> OTHER INFORMATION: synthetic

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Asp
                20                  25                  30

Leu Ala Trp Tyr Gln Gln Lys Pro Gly Lys Ala Pro Lys Leu Leu Ile
            35                  40                  45

Tyr Ser Ala Ser Tyr Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Pro Glu Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
```

```
                145                 150                 155                 160
        Glu Ser Val Thr Glu Gln Asp Ser Lys Asp Ser Thr Tyr Ser Leu Ser
                        165                 170                 175

Ser Thr Leu Thr Leu Ser Lys Ala Asp Tyr Glu Lys His Lys Val Tyr
                        180                 185                 190

Ala Cys Glu Val Thr His Gln Gly Leu Ser Ser Pro Val Thr Lys Ser
                        195                 200                 205

Phe Asn Arg Gly Glu Cys
                        210

<210> SEQ ID NO 10
<211> LENGTH: 214
<212> TYPE: PRT
<213> ORGANISM: Artificial Sequence
<220> FEATURE:
<223> OTHER INFORMATION: synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Ser Asp
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Pro Glu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 11
<211> LENGTH: 214
<212> TYPE: PRT
<213> ORGANISM: Artificial Sequence
<220> FEATURE:
<223> OTHER INFORMATION: synthetic

<400> SEQUENCE: 11

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Leu Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 228
<212> TYPE: PRT
<213> ORGANISM: Artificial Sequence
<220> FEATURE:
<223> OTHER INFORMATION: synthetic

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Leu
        35                  40                  45

Gly Glu Ile Ser Ala Ala Gly Gly Tyr Thr Asp Tyr Ala Asp Ser Val
 50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His
225

<210> SEQ ID NO 13
<211> LENGTH: 214
<212> TYPE: PRT
<213> ORGANISM: Artificial Sequence
<220> FEATURE:
<223> OTHER INFORMATION: synthetic

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 228
<212> TYPE: PRT
<213> ORGANISM: Artificial Sequence
<220> FEATURE:
<223> OTHER INFORMATION: synthetic

<400> SEQUENCE: 14

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45

Gly Glu Ile Ser Ala Ala Gly Gly Tyr Thr Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His
225

<210> SEQ ID NO 15
<211> LENGTH: 214
<212> TYPE: PRT
<213> ORGANISM: Artificial Sequence
<220> FEATURE:
<223> OTHER INFORMATION: synthetic

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Leu Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 228
<212> TYPE: PRT
<213> ORGANISM: Artificial Sequence
<220> FEATURE:
<223> OTHER INFORMATION: synthetic

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Asp
            20                  25                  30

Trp Ile His Trp Val Arg Gln Ala Pro Gly Lys Gly Leu Glu Trp Val
        35                  40                  45

Gly Glu Ile Ser Pro Ala Gly Ala Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Lys Val Ser Phe Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His
225

<210> SEQ ID NO 17
<211> LENGTH: 228
<212> TYPE: PRT
<213> ORGANISM: Artificial Sequence
<220> FEATURE:
<223> OTHER INFORMATION: synthetic

<400> SEQUENCE: 17

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asp
            20                  25                  30

Trp Ile His Trp Val Arg Gln Ala Pro Gly Lys Gly Leu Glu Trp Val
        35                  40                  45

Gly Glu Ile Ser Pro Ala Gly Ala Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Lys Val Ser Phe Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His
225
```

<210> SEQ ID NO 18
<211> LENGTH: 216
<212> TYPE: PRT
<213> ORGANISM: Artificial Sequence
<220> FEATURE:
<223> OTHER INFORMATION: synthetic

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Leu Phe Tyr
            20                  25                  30

Gly Asn Val Ala Trp Tyr Gln Gln Lys Pro Gly Lys Ala Pro Lys Leu
        35                  40                  45

Leu Ile Tyr Asp Gly Ser Tyr Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Ser Tyr Pro Ala
                85                  90                  95

Pro Tyr Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
```

```
            115                 120                 125
Ser Gly Thr Ala Ser Val Val Cys Leu Leu Asn Asn Phe Tyr Pro Arg
            130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
            195                 200                 205

Lys Ser Phe Asn Arg Gly Glu Cys
            210                 215
```

<210> SEQ ID NO 19
<211> LENGTH: 228
<212> TYPE: PRT
<213> ORGANISM: Artificial Sequence
<220> FEATURE:
<223> OTHER INFORMATION: synthetic

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Leu
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Lys Val Ser Phe Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His
225
```

<210> SEQ ID NO 20
<211> LENGTH: 228
<212> TYPE: PRT

<213> ORGANISM: Artificial Sequence
<220> FEATURE:
<223> OTHER INFORMATION: synthetic

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Lys Val Ser Phe Glu Ala Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His
225
```

<210> SEQ ID NO 21
<211> LENGTH: 218
<212> TYPE: PRT
<213> ORGANISM: Artificial Sequence
<220> FEATURE:
<223> OTHER INFORMATION: synthetic

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Val Trp Gly Gly
            20                  25                  30

Tyr Ile Ala Pro Val Ala Trp Tyr Gln Gln Lys Pro Gly Lys Ala Pro
        35                  40                  45

Lys Leu Leu Ile Tyr Asp Gly Ser Tyr Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Leu
                85                  90                  95
```

```
Pro Thr Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 22
<211> LENGTH: 218
<212> TYPE: PRT
<213> ORGANISM: Artificial Sequence
<220> FEATURE:
<223> OTHER INFORMATION: synthetic

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Ser Ile Ala Gly Ala
            20                  25                  30

Tyr Tyr Ala Pro Val Ala Trp Tyr Gln Gln Lys Pro Gly Lys Ala Pro
        35                  40                  45

Lys Leu Leu Ile Tyr Asp Gly Tyr Phe Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Leu
                85                  90                  95

Pro Ser Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 23
<211> LENGTH: 218
```

```
<212> TYPE: PRT
<213> ORGANISM: Artificial Sequence
<220> FEATURE:
<223> OTHER INFORMATION: synthetic

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Trp Ala Ala
            20                  25                  30

Tyr Phe Ala Pro Val Ala Trp Tyr Gln Gln Lys Pro Gly Lys Ala Pro
        35                  40                  45

Lys Leu Leu Ile Tyr Asp Gly Ser Tyr Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Leu
                85                  90                  95

Pro Ser Pro Tyr Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 24
<211> LENGTH: 108
<212> TYPE: PRT
<213> ORGANISM: Artificial Sequence
<220> FEATURE:
<223> OTHER INFORMATION: synthetic

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Thr Pro Tyr
                85                  90                  95

Thr Phe Gly Gln Gly Thr Lys Val Glu Ile Lys Arg
            100                 105
```

<210> SEQ ID NO 25
<211> LENGTH: 121
<212> TYPE: PRT
<213> ORGANISM: Artificial Sequence
<220> FEATURE:
<223> OTHER INFORMATION: synthetic

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asn
            20                  25                  30

Trp Ile His Trp Val Arg Gln Ala Pro Gly Lys Gly Leu Glu Trp Val
        35                  40                  45

Gly Glu Ile Ser Pro Ser Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Tyr Glu Ala Ala Met Asp Tyr Trp Gly
            100                 105                 110

Gln Gly Thr Leu Val Thr Val Ser Ser
        115                 120

<210> SEQ ID NO 26
<211> LENGTH: 108
<212> TYPE: PRT
<213> ORGANISM: Artificial Sequence
<220> FEATURE:
<223> OTHER INFORMATION: synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Leu Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg
            100                 105

<210> SEQ ID NO 27
<211> LENGTH: 108
<212> TYPE: PRT
<213> ORGANISM: Artificial Sequence
<220> FEATURE:
<223> OTHER INFORMATION: synthetic

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Leu Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg
            100                 105

<210> SEQ ID NO 28
<211> LENGTH: 121
<212> TYPE: PRT
<213> ORGANISM: Artificial Sequence
<220> FEATURE:
<223> OTHER INFORMATION: synthetic

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Leu
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser
        115                 120

<210> SEQ ID NO 29
<211> LENGTH: 108
<212> TYPE: PRT
<213> ORGANISM: Artificial Sequence
<220> FEATURE:
<223> OTHER INFORMATION: synthetic

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg
            100                 105

<210> SEQ ID NO 30
<211> LENGTH: 121
<212> TYPE: PRT
<213> ORGANISM: Artificial Sequence
<220> FEATURE:
<223> OTHER INFORMATION: synthetic

<400> SEQUENCE: 30

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
            35                  40                  45

Gly Glu Ile Ser Ala Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser
            115                 120

<210> SEQ ID NO 31
<211> LENGTH: 108
<212> TYPE: PRT
<213> ORGANISM: Artificial Sequence
<220> FEATURE:
<223> OTHER INFORMATION: synthetic

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Leu Ala Thr Asp
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg
            100                 105

<210> SEQ ID NO 32
<211> LENGTH: 121
<212> TYPE: PRT
<213> ORGANISM: Artificial Sequence
<220> FEATURE:
<223> OTHER INFORMATION: synthetic

<400> SEQUENCE: 32

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Asp
            20                  25                  30

Trp Ile His Trp Val Arg Gln Ala Pro Gly Lys Gly Leu Glu Trp Val
        35                  40                  45

Gly Glu Ile Ser Pro Ala Gly Ala Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Lys Val Ser Phe Glu Ala Ala Met Asp Tyr Trp Gly
            100                 105                 110

Gln Gly Thr Leu Val Thr Val Ser Ser
            115                 120

<210> SEQ ID NO 33
<211> LENGTH: 121
<212> TYPE: PRT
<213> ORGANISM: Artificial Sequence
<220> FEATURE:
<223> OTHER INFORMATION: synthetic

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asp
            20                  25                  30

Trp Ile His Trp Val Arg Gln Ala Pro Gly Lys Gly Leu Glu Trp Val
        35                  40                  45

Gly Glu Ile Ser Pro Ala Gly Ala Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Lys Val Ser Phe Glu Ala Ala Met Asp Tyr Trp Gly
            100                 105                 110

Gln Gly Thr Leu Val Thr Val Ser Ser
            115                 120

<210> SEQ ID NO 34
<211> LENGTH: 121
<212> TYPE: PRT
<213> ORGANISM: Artificial Sequence
<220> FEATURE:
<223> OTHER INFORMATION: synthetic

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Leu
        35                  40                  45

Gly Glu Ile Ser Ala Ala Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Lys Val Ser Phe Glu Ala Ala Met Asp Tyr Trp Gly
            100                 105                 110

Gln Gly Thr Leu Val Thr Val Ser Ser
        115                 120

<210> SEQ ID NO 35
<211> LENGTH: 121
<212> TYPE: PRT
<213> ORGANISM: Artificial Sequence
<220> FEATURE:
<223> OTHER INFORMATION: synthetic

<400> SEQUENCE: 35

Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ser Lys Val Ser Phe Glu Ala Ala Met Asp Tyr Trp Gly
            100                 105                 110

Gln Gly Thr Leu Val Thr Val Ser Ser
        115                 120

<210> SEQ ID NO 36
<211> LENGTH: 112
<212> TYPE: PRT
<213> ORGANISM: Artificial Sequence
<220> FEATURE:
<223> OTHER INFORMATION: synthetic

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Val Trp Gly Gly
            20                  25                  30

Tyr Ile Ala Pro Val Ala Trp Tyr Gln Gln Lys Pro Gly Lys Ala Pro
        35                  40                  45

Lys Leu Leu Ile Tyr Asp Gly Ser Tyr Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Leu
                85                  90                  95

Pro Thr Pro Tyr Thr Phe Gly Gln Gly Thr Lys Val Glu Ile Lys Arg
            100                 105                 110

```
<210> SEQ ID NO 37
<211> LENGTH: 112
<212> TYPE: PRT
<213> ORGANISM: Artificial Sequence
<220> FEATURE:
<223> OTHER INFORMATION: synthetic

<400> SEQUENCE: 37
```

Asp Ile Gln Met Thr Gln Ser Pro Ser Ser Leu Ser Ala Ser Val Gly
1               5                   10                  15

Asp Arg Val Thr Ile Thr Cys Arg Ala Asn Gln Ser Ile Ala Gly Ala
            20                  25                  30

Tyr Tyr Ala Pro Val Ala Trp Tyr Gln Gln Lys Pro Gly Lys Ala Pro
        35                  40                  45

Lys Leu Leu Ile Tyr Asp Gly Tyr Phe Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Leu
                85                  90                  95

Pro Ser Pro Tyr Thr Phe Gly Gln Gly Thr Lys Val Glu Ile Lys Arg
            100                 105                 110

```
<210> SEQ ID NO 38
<211> LENGTH: 112
<212> TYPE: PRT
<213> ORGANISM: Artificial Sequence
<220> FEATURE:
<223> OTHER INFORMATION: synthetic

<400> SEQUENCE: 38
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Trp Ala Ala
            20                  25                  30

Tyr Phe Ala Pro Val Ala Trp Tyr Gln Gln Lys Pro Gly Lys Ala Pro
        35                  40                  45

Lys Leu Leu Ile Tyr Asp Gly Ser Tyr Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Arg Leu
                85                  90                  95

Pro Ser Pro Tyr Thr Phe Gly Gln Gly Thr Lys Val Glu Ile Lys Arg
            100                 105                 110

```
<210> SEQ ID NO 39
<211> LENGTH: 110
<212> TYPE: PRT
<213> ORGANISM: Artificial Sequence
<220> FEATURE:
<223> OTHER INFORMATION: synthetic

<400> SEQUENCE: 39
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Leu Phe Tyr
            20                  25                  30

Gly Asn Val Ala Trp Tyr Gln Gln Lys Pro Gly Lys Ala Pro Lys Leu
        35                  40                  45

```
Leu Ile Tyr Asp Gly Ser Tyr Leu Tyr Ser Gly Val Pro Ser Arg Phe
        50                  55                  60

Ser Gly Ser Gly Ser Gly Thr Asp Phe Thr Leu Thr Ile Ser Ser Leu
 65              70                  75                      80

Gln Pro Glu Asp Phe Ala Thr Tyr Tyr Cys Gln Gln Ser Tyr Pro Ala
                85                  90                  95

Pro Tyr Thr Phe Gly Gln Gly Thr Lys Val Glu Ile Lys Arg
            100                 105                 110
```

<210> SEQ ID NO 40
<211> LENGTH: 108
<212> TYPE: PRT
<213> ORGANISM: Artificial Sequence
<220> FEATURE:
<223> OTHER INFORMATION: synthetic

<400> SEQUENCE: 40

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Asp Leu Ala Thr Asp
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg
            100                 105
```

<210> SEQ ID NO 41
<211> LENGTH: 114
<212> TYPE: PRT
<213> ORGANISM: Artificial Sequence
<220> FEATURE:
<223> OTHER INFORMATION: synthetic

<400> SEQUENCE: 41

```
Asp Ile Gln Met Thr Gln Ser Pro Ser Ser Leu Ser Ala Ser Val Gly
 1               5                   10                  15

Asp Arg Val Thr Ile Thr Cys Arg Ala Ser Gln Ala Leu Gly Asp Ser
             20                  25                  30

Glu Asn Gly Tyr Ala Asp Val Ala Trp Tyr Gln Gln Lys Pro Gly Lys
         35                  40                  45

Ala Pro Lys Leu Leu Ile Tyr Glu Gly Ser Ser Leu Tyr Ser Gly Val
 50                  55                  60

Pro Ser Arg Phe Ser Gly Ser Gly Ser Gly Thr Asp Phe Thr Leu Thr
 65              70                  75                      80

Ile Ser Ser Leu Gln Pro Glu Asp Phe Ala Thr Tyr Tyr Cys Gln Gln
                85                  90                  95

Ala Ala Pro Ser Pro Tyr Thr Phe Gly Gln Gly Thr Lys Val Glu Ile
            100                 105                 110

Lys Arg
```

<210> SEQ ID NO 42

```
<211> LENGTH: 114
<212> TYPE: PRT
<213> ORGANISM: Artificial Sequence
<220> FEATURE:
<223> OTHER INFORMATION: synthetic

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Leu Leu Ala Ser
            20                  25                  30

His Asp Gly Thr Pro Trp Val Ala Trp Tyr Gln Gln Lys Pro Gly Lys
        35                  40                  45

Ala Pro Lys Leu Leu Ile Tyr Asp Ala Ser Tyr Leu Tyr Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Ser Thr Phe Ala Pro Tyr Thr Phe Gly Gln Gly Thr Lys Val Glu Ile
            100                 105                 110

Lys Arg

<210> SEQ ID NO 43
<211> LENGTH: 108
<212> TYPE: PRT
<213> ORGANISM: Artificial Sequence
<220> FEATURE:
<223> OTHER INFORMATION: synthetic

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Glu Ile Phe Pro Asp
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ala Pro Thr Pro Tyr
                85                  90                  95

Thr Phe Gly Gln Gly Thr Lys Val Glu Ile Lys Arg
            100                 105

<210> SEQ ID NO 44
<211> LENGTH: 108
<212> TYPE: PRT
<213> ORGANISM: Artificial Sequence
<220> FEATURE:
<223> OTHER INFORMATION: synthetic

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ala Ser Asp
            20                  25                  30

Val Ala Trp Tyr Gln Gln Lys Pro Gly Lys Ala Pro Lys Leu Leu Ile
```

```
                35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Glu Pro Glu Pro Tyr
                85                  90                  95

Thr Phe Gly Gln Gly Thr Lys Val Glu Ile Lys Arg
            100                 105

<210> SEQ ID NO 45
<211> LENGTH: 108
<212> TYPE: PRT
<213> ORGANISM: Artificial Sequence
<220> FEATURE:
<223> OTHER INFORMATION: synthetic

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Gly Ser Asp
            20                  25                  30

Leu Ala Trp Tyr Gln Gln Lys Pro Gly Lys Ala Pro Lys Leu Leu Ile
        35                  40                  45

Tyr Ser Ala Ser Tyr Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Pro Glu Pro Tyr
                85                  90                  95

Thr Phe Gly Gln Gly Thr Lys Val Glu Ile Lys Arg
            100                 105

<210> SEQ ID NO 46
<211> LENGTH: 108
<212> TYPE: PRT
<213> ORGANISM: Artificial Sequence
<220> FEATURE:
<223> OTHER INFORMATION: synthetic

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Ser Asp
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asp Pro Glu Pro Tyr
                85                  90                  95

Thr Phe Gly Gln Gly Thr Lys Val Glu Ile Lys Arg
            100                 105

<210> SEQ ID NO 47
<211> LENGTH: 7
```

```
<212> TYPE: PRT
<213> ORGANISM: Artificial Sequence
<220> FEATURE:
<223> OTHER INFORMATION: synthetic

<400> SEQUENCE: 47

Phe Thr Gly Asn Trp Ile His
1               5

<210> SEQ ID NO 48
<211> LENGTH: 7
<212> TYPE: PRT
<213> ORGANISM: Artificial Sequence
<220> FEATURE:
<223> OTHER INFORMATION: synthetic

<400> SEQUENCE: 48

Leu Ser Gly Asp Trp Ile His
1               5

<210> SEQ ID NO 49
<211> LENGTH: 12
<212> TYPE: PRT
<213> ORGANISM: Artificial Sequence
<220> FEATURE:
<223> OTHER INFORMATION: synthetic

<400> SEQUENCE: 49

Val Gly Glu Ile Ser Pro Ser Gly Gly Tyr Thr Asp
1               5                   10

<210> SEQ ID NO 50
<211> LENGTH: 12
<212> TYPE: PRT
<213> ORGANISM: Artificial Sequence
<220> FEATURE:
<223> OTHER INFORMATION: synthetic

<400> SEQUENCE: 50

Leu Gly Glu Ile Ser Ala Ala Gly Gly Tyr Thr Asp
1               5                   10

<210> SEQ ID NO 51
<211> LENGTH: 12
<212> TYPE: PRT
<213> ORGANISM: Artificial Sequence
<220> FEATURE:
<223> OTHER INFORMATION: synthetic

<400> SEQUENCE: 51

Val Gly Glu Ile Ser Ala Ala Gly Gly Tyr Thr Asp
1               5                   10

<210> SEQ ID NO 52
<211> LENGTH: 14
<212> TYPE: PRT
<213> ORGANISM: Artificial Sequence
<220> FEATURE:
<223> OTHER INFORMATION: synthetic

<400> SEQUENCE: 52

Ala Arg Glu Ser Arg Val Ser Tyr Glu Ala Ala Met Asp Tyr
1               5                   10

<210> SEQ ID NO 53
<211> LENGTH: 14
<212> TYPE: PRT
```

-continued

```
<213> ORGANISM: Artificial Sequence
<220> FEATURE:
<223> OTHER INFORMATION: synthetic

<400> SEQUENCE: 53

Ala Arg Glu Ser Arg Val Ser Phe Glu Ala Ala Met Asp Tyr
1               5                   10

<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Asp Leu Ala Thr Asp Val Ala
1               5

<210> SEQ ID NO 55
<211> LENGTH: 7
<212> TYPE: PRT
<213> ORGANISM: Artificial Sequence
<220> FEATURE:
<223> OTHER INFORMATION: synthetic

<400> SEQUENCE: 55

Asn Ile Ala Thr Asp Val Ala
1               5

<210> SEQ ID NO 56
<211> LENGTH: 4
<212> TYPE: PRT
<213> ORGANISM: Artificial Sequence
<220> FEATURE:
<223> OTHER INFORMATION: synthetic

<400> SEQUENCE: 56

Ser Ala Ser Phe
1

<210> SEQ ID NO 57
<211> LENGTH: 7
<212> TYPE: PRT
<213> ORGANISM: Artificial Sequence
<220> FEATURE:
<223> OTHER INFORMATION: synthetic

<400> SEQUENCE: 57

Ser Glu Pro Glu Pro Tyr Thr
1               5

<210> SEQ ID NO 58
<211> LENGTH: 108
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 59
<211> LENGTH: 7
<212> TYPE: PRT
<213> ORGANISM: Artificial Sequence
<220> FEATURE:
<223> OTHER INFORMATION: synthetic

<400> SEQUENCE: 59

Phe Ser Gly Asp Trp Ile His
1               5

<210> SEQ ID NO 60
<211> LENGTH: 12
<212> TYPE: PRT
<213> ORGANISM: Artificial Sequence
<220> FEATURE:
<223> OTHER INFORMATION: synthetic

<400> SEQUENCE: 60

Val Gly Glu Ile Ser Pro Ala Gly Ala Tyr Thr Asp
1               5                   10

<210> SEQ ID NO 61
<211> LENGTH: 14
<212> TYPE: PRT
<213> ORGANISM: Artificial Sequence
<220> FEATURE:
<223> OTHER INFORMATION: synthetic

<400> SEQUENCE: 61

Ala Arg Glu Ala Lys Val Ser Phe Glu Ala Ala Met Asp Tyr
1               5                   10

<210> SEQ ID NO 62
<211> LENGTH: 7
<212> TYPE: PRT
<213> ORGANISM: Artificial Sequence
<220> FEATURE:
<223> OTHER INFORMATION: synthetic

<400> SEQUENCE: 62

Phe Thr Gly Asp Trp Ile His
1               5

<210> SEQ ID NO 63
<211> LENGTH: 121
<212> TYPE: PRT
<213> ORGANISM: Artificial Sequence
<220> FEATURE:
<223> OTHER INFORMATION: synthetic

<400> SEQUENCE: 63

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Gly Asp
```

```
                     20                  25                  30

Trp Ile His Trp Val Arg Gln Ala Pro Gly Lys Gly Leu Glu Trp Val
            35                  40                  45

Gly Glu Ile Ser Pro Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Arg Val Ser Phe Glu Ala Ala Met Asp Tyr Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial Sequence
<220> FEATURE:
<223> OTHER INFORMATION: synthetic

<400> SEQUENCE: 64

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
            35                  40                  45

Gly Glu Ile Ser Ala Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Arg Val Ser Tyr Glu Ala Ala Met Asp Tyr Trp Gly
            100                 105                 110

Gln Gly Thr Leu Val Thr Val Ser Ser
        115                 120

<210> SEQ ID NO 65
<211> LENGTH: 121
<212> TYPE: PRT
<213> ORGANISM: Artificial Sequence
<220> FEATURE:
<223> OTHER INFORMATION: synthetic

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
            35                  40                  45

Gly Glu Ile Ser Pro Ala Gly Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80
```

-continued

```
Leu Gln Met Asn Ser Leu Arg Ala Glu Asp Thr Ala Val Tyr Tyr Cys
                 85                  90                  95

Ala Arg Glu Ser Arg Val Ser Phe Glu Ala Ala Met Asp Tyr Trp Gly
            100                 105                 110

Gln Gly Thr Leu Val Thr Val Ser Ser
        115                 120

<210> SEQ ID NO 66
<211> LENGTH: 121
<212> TYPE: PRT
<213> ORGANISM: Artificial Sequence
<220> FEATURE:
<223> OTHER INFORMATION: synthetic

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Asn
            20                  25                  30

Trp Ile His Trp Val Arg Gln Ala Pro Gly Lys Gly Leu Glu Trp Val
        35                  40                  45

Gly Glu Ile Ser Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                 85                  90                  95

Ala Arg Glu Ala Arg Val Ser Tyr Glu Ala Ala Met Asp Tyr Trp Gly
            100                 105                 110

Gln Gly Thr Leu Val Thr Val Ser Ser
        115                 120

<210> SEQ ID NO 67
<211> LENGTH: 121
<212> TYPE: PRT
<213> ORGANISM: Artificial Sequence
<220> FEATURE:
<223> OTHER INFORMATION: synthetic

<400> SEQUENCE: 67

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45

Gly Glu Ile Ser Ala Ala Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                 85                  90                  95

Ala Arg Glu Ala Arg Val Ser Tyr Glu Ala Ala Met Asp Tyr Trp Gly
            100                 105                 110

Gln Gly Thr Leu Val Thr Val Ser Ser
        115                 120

<210> SEQ ID NO 68
```

```
<211> LENGTH: 121
<212> TYPE: PRT
<213> ORGANISM: Artificial Sequence
<220> FEATURE:
<223> OTHER INFORMATION: synthetic

<400> SEQUENCE: 68
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Ile His Trp Val Arg Gln Ala Pro Gly Lys Gly Leu Glu Trp Val
        35                  40                  45

Gly Glu Ile Ser Ala Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Arg Val Ser Phe Glu Ala Ala Met Asp Tyr Trp Gly
            100                 105                 110

Gln Gly Thr Leu Val Thr Val Ser Ser
        115                 120

```
<210> SEQ ID NO 69
<211> LENGTH: 121
<212> TYPE: PRT
<213> ORGANISM: Artificial Sequence
<220> FEATURE:
<223> OTHER INFORMATION: synthetic

<400> SEQUENCE: 69
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Thr Gly Asp
            20                  25                  30

Trp Ile His Trp Val Arg Gln Ala Pro Gly Lys Gly Leu Glu Trp Val
        35                  40                  45

Gly Glu Ile Ser Pro Ala Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Arg Val Ser Tyr Glu Ala Ala Met Asp Tyr Trp Gly
            100                 105                 110

Gln Gly Thr Leu Val Thr Val Ser Ser
        115                 120

```
<210> SEQ ID NO 70
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(23)
<223> OTHER INFORMATION: n is A, C, G, or T
<220> FEATURE:
<221> NAME/KEY: misc_feature
```

```
<222> LOCATION: (24)..(24)
<223> OTHER INFORMATION: N is G or T
<220> FEATURE:
<221> NAME/KEY: misc_feature
<222> LOCATION: (25)..(27)
<223> OTHER INFORMATION: n is A, C, G, or T
<220> FEATURE:
<221> NAME/KEY: misc_feature
<222> LOCATION: (28)..(28)
<223> OTHER INFORMATION: N is A or G
<220> FEATURE:
<221> NAME/KEY: misc_feature
<222> LOCATION: (28)..(28)
<223> OTHER INFORMATION: n is A or G

<400> SEQUENCE: 70
acttattact gtcagcaann nnnnnnnnst ccttacacgt tcgga          45

<210> SEQ ID NO 71
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(21)
<223> OTHER INFORMATION: n is A, C, G, or T
<220> FEATURE:
<221> NAME/KEY: misc_feature
<222> LOCATION: (25)..(27)
<223> OTHER INFORMATION: n is A, C, G, or T
<220> FEATURE:
<221> NAME/KEY: misc_feature
<222> LOCATION: (28)..(28)
<223> OTHER INFORMATION: n is A or G
<220> FEATURE:
<221> NAME/KEY: misc_feature
<222> LOCATION: (29)..(29)
<223> OTHER INFORMATION: n is G or C

<400> SEQUENCE: 71
acttattact gtcagcaann ntacnnnnnt ccttacacgt tcgga          45

<210> SEQ ID NO 72
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(19)
<223> OTHER INFORMATION: n is A, G, or T
<220> FEATURE:
<221> NAME/KEY: misc_feature
<222> LOCATION: (22)..(30)
<223> OTHER INFORMATION: n is A, C, G, or T

<400> SEQUENCE: 72
acttattact gtcagcaang gnnnnnnnnn ccttacacgt tcgga          45

<210> SEQ ID NO 73
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(19)
<223> OTHER INFORMATION: n is G or T
<220> FEATURE:
```

```
<221> NAME/KEY: misc_feature
<222> LOCATION: (20)..(20)
<223> OTHER INFORMATION: n is A or C
<220> FEATURE:
<221> NAME/KEY: misc_feature
<222> LOCATION: (22)..(23)
<223> OTHER INFORMATION: n is A, C, G, or T
<220> FEATURE:
<221> NAME/KEY: misc_feature
<222> LOCATION: (24)..(24)
<223> OTHER INFORMATION: n is G or T
<220> FEATURE:
<221> NAME/KEY: misc_feature
<222> LOCATION: (25)..(39)
<223> OTHER INFORMATION: n is A, C, G, or T

<400> SEQUENCE: 73
acttattact gtcagcaann tnnnnnnnnn ccttacacgt tcgga            45

<210> SEQ ID NO 74
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(23)
<223> OTHER INFORMATION: n is A, C, G or T
<220> FEATURE:
<221> NAME/KEY: misc_feature
<222> LOCATION: (24)..(24)
<223> OTHER INFORMATION: n is G or T
<220> FEATURE:
<221> NAME/KEY: misc_feature
<222> LOCATION: (25)..(29)
<223> OTHER INFORMATION: n is A, C, G or T
<220> FEATURE:
<221> NAME/KEY: misc_feature
<222> LOCATION: (30)..(30)
<223> OTHER INFORMATION: n is G or T

<400> SEQUENCE: 74
acttattact gtcagcaann nnnnnnnnnn ccttacacgt tcgga            45

<210> SEQ ID NO 75
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(19)
<223> OTHER INFORMATION: n is A, G, or T
<220> FEATURE:
<221> NAME/KEY: misc_feature
<222> LOCATION: (22)..(26)
<223> OTHER INFORMATION: n is A, C, G, or T
<220> FEATURE:
<221> NAME/KEY: misc_feature
<222> LOCATION: (27)..(27)
<223> OTHER INFORMATION: n is G, or T
<220> FEATURE:
<221> NAME/KEY: misc_feature
<222> LOCATION: (28)..(28)
<223> OTHER INFORMATION: n is A or G
<220> FEATURE:
<221> NAME/KEY: misc_feature
<222> LOCATION: (29)..(29)
<223> OTHER INFORMATION: n is G or C

<400> SEQUENCE: 75
acttattact gtcagcaang gnnnnnnnnt ccttacacgt tcgga            45
```

```
<210> SEQ ID NO 76
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (19)..(19)
<223> OTHER INFORMATION: n is G or T
<220> FEATURE:
<221> NAME/KEY: misc_feature
<222> LOCATION: (20)..(20)
<223> OTHER INFORMATION: n is A or C
<220> FEATURE:
<221> NAME/KEY: misc_feature
<222> LOCATION: (22)..(23)
<223> OTHER INFORMATION: n is A, C, G, or T
<220> FEATURE:
<221> NAME/KEY: misc_feature
<222> LOCATION: (24)..(24)
<223> OTHER INFORMATION: n is G or T
<220> FEATURE:
<221> NAME/KEY: misc_feature
<222> LOCATION: (25)..(26)
<223> OTHER INFORMATION: n is A, C, G or T
<220> FEATURE:
<221> NAME/KEY: misc_feature
<222> LOCATION: (27)..(27)
<223> OTHER INFORMATION: n is G or T
<220> FEATURE:
<221> NAME/KEY: misc_feature
<222> LOCATION: (28)..(28)
<223> OTHER INFORMATION: n is A or G
<220> FEATURE:
<221> NAME/KEY: misc_feature
<222> LOCATION: (29)..(29)
<223> OTHER INFORMATION: n is G or C

<400> SEQUENCE: 76
acttattact gtcagcaann tnnnnnnnnt ccttacacgt tcgga                45

<210> SEQ ID NO 77
<211> LENGTH: 36
<212> TYPE: DNA
<213> ORGANISM: Artificial Sequence
<220> FEATURE:
<223> OTHER INFORMATION: synthetic

<400> SEQUENCE: 77
tcttgtgaca aaactcacag tggcggtggc tctggt                          36

<210> SEQ ID NO 78
<211> LENGTH: 7
<212> TYPE: PRT
<213> ORGANISM: Artificial sequence
<220> FEATURE:
<223> OTHER INFORMATION: synthetic

<400> SEQUENCE: 78

Asp Val Ser Thr Ala Val Ala
1               5

<210> SEQ ID NO 79
<211> LENGTH: 7
<212> TYPE: PRT
<213> ORGANISM: Artificial sequence
<220> FEATURE:
<223> OTHER INFORMATION: synthetic
```

```
<400> SEQUENCE: 79

Ser Tyr Pro Thr Pro Tyr Thr
1               5
```